United States Patent
Nishimura et al.

(10) Patent No.: US 10,206,989 B2
(45) Date of Patent: Feb. 19, 2019

(54) CDCA1 EPITOPE PEPTIDES FOR TH1 CELLS AND VACCINES CONTAINING THE SAME

(71) Applicant: OncoTherapy Science, Inc., Kanagawa (JP)

(72) Inventors: Yasuharu Nishimura, Kumamoto (JP); Yusuke Tomita, Kumamoto (JP); Ryuji Osawa, Kawasaki (JP)

(73) Assignee: OncoTherapy Science, Inc., Kanagawa (JP)

( * ) Notice: Subject to any disclaimer, the term of this patent is extended or adjusted under 35 U.S.C. 154(b) by 20 days.

(21) Appl. No.: 15/411,115

(22) Filed: Jan. 20, 2017

(65) Prior Publication Data
US 2017/0224795 A1 Aug. 10, 2017
US 2018/0117135 A9 May 3, 2018

Related U.S. Application Data

(62) Division of application No. 14/413,413, filed as application No. PCT/JP2013/004244 on Jul. 9, 2013, now Pat. No. 9,687,538.

(60) Provisional application No. 61/669,971, filed on Jul. 10, 2012.

(51) Int. Cl.
| | |
|---|---|
| A61K 38/00 | (2006.01) |
| A61K 39/00 | (2006.01) |
| C07K 14/47 | (2006.01) |
| C12N 5/0783 | (2010.01) |
| C07K 16/28 | (2006.01) |
| C07K 7/06 | (2006.01) |
| C07K 7/08 | (2006.01) |
| C07K 14/00 | (2006.01) |
| C07K 16/30 | (2006.01) |
| C12N 5/078 | (2010.01) |

(52) U.S. Cl.
CPC ......... *A61K 39/0011* (2013.01); *A61K 38/00* (2013.01); *C07K 7/06* (2013.01); *C07K 7/08* (2013.01); *C07K 14/00* (2013.01); *C07K 14/47* (2013.01); *C07K 14/4702* (2013.01); *C07K 16/2833* (2013.01); *C07K 16/30* (2013.01); *C12N 5/0634* (2013.01); *C12N 5/0636* (2013.01); *C12N 5/0637* (2013.01); *C12N 5/0638* (2013.01); *A61K 2039/5154* (2013.01); *A61K 2039/57* (2013.01); *A61K 2039/70* (2013.01); *C07K 2317/76* (2013.01); *C12N 2501/405* (2013.01); *C12N 2502/11* (2013.01)

(58) Field of Classification Search
None
See application file for complete search history.

(56) References Cited

U.S. PATENT DOCUMENTS

| | | | |
|---|---|---|---|
| 6,699,703 B1 | 3/2004 | Doucette-Stamm et al. | |
| 6,858,204 B2 | 2/2005 | Henderson et al. | |
| 6,867,283 B2 | 3/2005 | Barnea | |
| 7,214,786 B2 | 5/2007 | Kovalic et al. | |
| 7,776,341 B2 | 8/2010 | Belisle et al. | |
| 8,598,125 B2 * | 12/2013 | Nishimura ......... | A61K 39/0011 514/19.2 |
| 9,101,585 B2 | 8/2015 | Fritsche | |
| 9,132,177 B2 | 9/2015 | Fritsche | |
| 9,387,238 B2 | 7/2016 | Tsunoda | |
| 2006/0088527 A1 | 4/2006 | Henderson et al. | |
| 2006/0216301 A1 | 9/2006 | Tahara et al. | |
| 2007/0053922 A1 | 3/2007 | Sette et al. | |
| 2007/0269432 A1 | 11/2007 | Nakamura et al. | |
| 2007/0271630 A1 | 11/2007 | Boukharov et al. | |
| 2009/0175844 A1 | 7/2009 | Nakamura et al. | |
| 2009/0208514 A1 | 8/2009 | Nakamura et al. | |
| 2009/0215683 A1 | 8/2009 | Nakamura et al. | |
| 2009/0286856 A1 | 11/2009 | Nakamura et al. | |
| 2009/0317392 A1 | 12/2009 | Nakamura et al. | |
| 2011/0152199 A1 | 6/2011 | Nishimura et al. | |
| 2011/0189214 A1 | 8/2011 | Tsunoda et al. | |
| 2011/0263012 A1 | 10/2011 | Nakamura et al. | |
| 2012/0010090 A1 | 1/2012 | Nakamura et al. | |
| 2012/0014996 A1 | 1/2012 | Nakamura et al. | |
| 2012/0021946 A1 | 1/2012 | Nakamura et al. | |
| 2013/0011933 A1 | 1/2013 | Nakamura et al. | |

FOREIGN PATENT DOCUMENTS

| | | |
|---|---|---|
| EP | 2186889 A | 5/2010 |
| WO | 98/53071 | 11/1998 |

(Continued)

OTHER PUBLICATIONS

Skolnick et al. (Trends in Biotech., 18(1):34-39, 2000) (Year: 2000).*

(Continued)

*Primary Examiner* — Sheela J. Huff
(74) *Attorney, Agent, or Firm* — Kilpatrick Townsend & Stockton LLP

(57) ABSTRACT

Isolated CDCA1-derived epitope peptides having Th1 cell inducibility are disclosed herein. Such peptides can be recognized by MHC class II molecules and induce Th1 cells. In preferred embodiments, such a peptide of the present invention can promiscuously bind to MHC class II molecules and induce CDCA1-specific cytotoxic T lymphocytes (CTLs) in addition to Th1 cells. Such peptides are thus suitable for use in enhancing immune response in a subject, and accordingly find use in cancer immunotherapy, in particular, as cancer vaccines. Also disclosed herein are polynucleotides that encode any of the aforementioned peptides, APCs and Th1 cells induced by such peptides and methods of induction associated therewith. Pharmaceutical compositions that comprise any of the aforementioned components as active ingredients find use in the treatment and/or prevention of cancers or tumors.

15 Claims, 46 Drawing Sheets

Specification includes a Sequence Listing.

(56) References Cited

FOREIGN PATENT DOCUMENTS

| WO | 00/78806 A1 | 12/2000 |
| --- | --- | --- |
| WO | 01/22920 A2 | 4/2001 |
| WO | 01/085942 A | 11/2001 |
| WO | 02/004514 | 1/2002 |
| WO | 02/094981 A2 | 11/2002 |
| WO | 03/025010 A2 | 3/2003 |
| WO | 03/037267 A2 | 5/2003 |
| WO | 2004/031413 A2 | 4/2004 |
| WO | 2004/067023 A2 | 8/2004 |
| WO | 2004/080148 A2 | 9/2004 |
| WO | 2005/028676 A2 | 3/2005 |
| WO | 2005/089735 A2 | 9/2005 |
| WO | 2006/085684 A2 | 8/2006 |
| WO | 2007/013480 A2 | 2/2007 |
| WO | 2007/013665 A2 | 2/2007 |
| WO | 2007/013671 A2 | 2/2007 |
| WO | 2009/025117 A1 | 2/2009 |
| WO | 2009/153992 A1 | 12/2009 |
| WO | WO-2013040142 A2 * | 3/2013 ............. A61K 39/12 |

OTHER PUBLICATIONS

International Search Report and Written Opinion dated Sep. 24, 2013 for PCT Application No. PCT/JP2013/004244, 4 pages.
Adams, et al., "Prediction of binding to MHC class I molecules" *J Immunol Methods*, vol. 185, No. 2, pp. 181-190 (1995).
Belli, et al., "Vaccination of Metastatic Melanoma Patients with Autologous Tumor-Derived Heat Shock Protein gp96-Peptide complexes: Clinical and Immunologic Findings", *J Clin Oncol*. vol. 20, No. 20, pp. 4169-4180 (2002).
Bevan, "Helping the CD8+ T-Cell Response", *Nat Rev Immunol*. vol. 4, No. 8, pp. 595-602 (2004).
Boon, "Tumor Antigens Recognized by Cytolytic T Lymphocytes: Present Perspectives for Specific Immunotherapy," *Int J Cancer*, vol. 54, No. 2, pp. 177-180 (1993).
Boon et al., "Human Tumor Antigens Recognized by T Lymphocytes," *J Exp Med*., vol. 183, No. 3, pp. 725-729 (1996).
Bos et al., "CD4+ T cell help in the tumor milieu is required for recruitment and cytolytic function of CD8+ T lymphocytes", *Cancer Res*, vol. 70, No. 21, pp. 8368-8377 (2010).
Butterfield, et al., "Generation of Human T-cell Responses to an HLA-A2.1—restricted Peptide Epitope Derived from α—Fetoprotein," *Cancer Res*., vol. 59, No. 13, pp. 3134-3142 (1999).
Chamoto et al., "Potentiation of Tumor Eradication by Adoptive Immunotherapy with T-cell Receptor Gene-Transduced T-Helper Type 1 Cells", *Cancer Res*, vol. 64, No. 1, pp. 386-390 (2004).
Coulie, et al., "Cytolytic T-cell Responses of cancer patients vaccinated with a MAGE antigen", *Immunol Rev*., vol. 188, pp. 33-42 (2002).
Database printout: GSP: AAG74867 (2001).
Database Geneseq, ADS11001 (2004).
Dermer, "Another Anniversary for the War on Cancer", *Bio/Technology*, vol. 12, pp. 320 (1994).
Dionne, et al., "Functional characterization of CTL against gp100 altered peptide ligands", *Cancer Immunol Immunother*. vol. 52, No. 4, pp. 199-206 (2003).
Dionne, et al., "Her-2/neu altered peptide ligand-induced CTL responses: implications for peptides with increased HLA affinity and T-cell-receptor interaction", *Cancer Immunol Immunother*. vol. 53, No. 4, pp. 307-314 (2004).
Engelhard, "Structure of peptides associated with MHC class I molecules" *Curr. Opin Immunol*., vol. 6, No. 1, pp. 13-23 (1994).
Ezzell et al., "Cancer "Vaccines": An Idea Whose Time Has Come?" *J NIH Res*., vol. 7, pp. 46-49 (1995).
Falk, et al., "Allele-specific motifs revealed by sequencing of self-peptides eluted from MHC molecules", *Nature*, vol. 351, No. 6324, pp. 290-296 (1991).
Freshney et al., Culture of Animal Cells: A Manual of Basic Technique, pp. 3-4, New York, NY, Alan R. Liss, Inc. (1983).

Fujie, et al., "A Mage-1-Encoded H:A-A24-Binding Synthetic Peptide Induces Specific Anti-tumor Cytotoxic T Lymphocytes", *Int. J. Cancer*., vol. 80, No. 2, pp. 169-172 (1999).
GenBan: AAY06266.1, "Sequence 166 from patent U.S. Pat. No. 6,867,283", (2005).
Guo et al., "Different length peptides bind to HLA-Aw68 similarly at their ends but bulge out in the middle", *Nature*, vol. 360, No. 6402, pp. 364-366 (1992).
Gura, "Systems for Identifying New Drugs are Often Faulty", *Science*, vol. 278, No. 5340, pp. 1041-1042 (1997).
Harao et al., "HLA-A2-restricted CTL epitopes of a novel lung cancer-associated cancer testis antigen, cell division cycle associated 1, can induce tumor-reactive CTL", *Int. J Cancer*, vol. 123, No. 11, pp. 2616-2625 (2008).
Harao et al., "Cell division cycle associated 1, an ideal lung cancer antigen for immunotherapy, identified using cDNA microarray analysis", Doctor's thesis, Graduate School of Medical Sciences, Kumamoto University, Kumamoto, Japan (Mar. 2008), with English translation. http://www.medic.kumamoto-u.ac.jp/dept/immunoge/frame/Thesis%20harao.pdf.
Harao et al., "Development of cancer immunotherapy targeting a novel cancer-testis antigen, CDCA1, that highly expresses in lung cancer" *Abstract of the 12th Annueal Meeting of the Society for Fundamental Cancer Immunology*, p. 34 (Jun. 2008), with English translation.
Harao et al., "Identification of a novel cancer-testis antigen, CDCA1, that is useful for immunotherapy for lung cancer", *Journal of Japan Surgical Society*, vol. 109, Suppl. 2, pp. 282 (#SF-077-1) (2008), with English translation.
Harao et al., "CDCA1, a novel cancer-testis antigen useful for immunotherapy of lung cancer", *Abstract of the 66th Annual Meeting of the Japanese Cancer Association*, pp. 163-164 (#p-294) (2007).
Harris, "Structure and Function of the p53 Tumor Suppressor Gene: Clues for Rational Cancer Therapeutic Strategies," *J Natl Cancer Inst*., vol. 88, No. 20, pp. 1442-1455 (1996).
Hayama et al., Activation of CDCA-KNTC2, Members of Centromere Protein Complex, Involved in Pulmonary Carcinogenesis, *Cancer Res*, vol. 66, No. 21, pp. 10339-10348 (2006).
Hoffmann et al., "The Ability of Variant Peptides to Reverse the Nonresponsiveness of T Lymphocytes to the Wild-Type Sequence $p53_{264-272}$ Epitope," *J Immunol*, vol. 168, No. 3, pp. 1338-1347 (2002).
Ishizaki et al., "Inhibition of Tumor Growth with Antiangiogenic Cancer Vaccine Using Epitope Peptides Derived from Human Vascular Endothelial Growth Factor Receptor 1", *Clin Cancer Res*. vol. 12, No. 19, pp. 5841-5849 (2006).
Jain, "Barriers to Drug Delivery in Solid Tumors", *Sci Am*., vol. 271, No. 1, pp. 58-65 (1994).
Johnson et al., "The clinical impact of screening and other experimental tumor studies", *Cancer Treat Rev*., vol. 2, No. 1, pp. 1-31 (1975).
Kast et al., Role of HLA-A in Identification of Potential CTL Epitopes in Human Papillomavirus Type 16 E6 and E7 Proteins, *J Immunol*, vol. 152, No. 8, pp. 3904-3912 (1994).
Kikuchi, et al., "Identification of a Sart-1-Derived Peptide Capable of Inducing HLA-A24-Restricted and Tumor-Specific Cytotoxic T Lymphocytes", *Int. J Cancer*, vol. 81, No. 3, pp. 459-466 (1999).
Kondo, et al., "Prominent Roles of Secondary Anchor Residues in Peptide Binding to Hla-A24 Human Class I Molecules", *J Immunol*. vol. 155, No. 9, pp. 4307-4312 (1995).
Kubo et al., "Definition of Specific Peptide Motifs for Four Major HLA-A Alleles," *J Immunol*, vol. 152, No. 8, pp. 3913-3924 (1994).
Liu et al., "Human NUF2 Interacts with Centromere-associated Protein E and is Essential for a Stable Spindle Microtubule-Kinetochore Attachment", *J. Biol Chem*, vol. 282, No. 29, pp. 21415-21424 (2007).
Melief et al., "Immunotherapy of established (pre)malignant disease by synthetic long peptide vaccines", *Nat Rev Cancer*, 8(5):351-360 (2008).

(56) References Cited

OTHER PUBLICATIONS

Naylor, et al., "Peptide Based Vaccine Approaches for Cancer—A Novel Approach Using a WT-1 Synthetic Long Peptide and the IRX-2 Immunomodulatory Regimen," *Cancers*, vol. 3 (4), pp. 3991-4009 (Oct. 25, 2011).

Oiso, et al., "A Newly Identified Mage-3-Derived Epitope Recognized by HLA-A24-Restricted Cytotoxic T Lymphocytes", *Int J Cancer*, vol. 81, No. 3, pp. 387-394.

Parker, et al., "Scheme for Ranking Potential HLA-A2 Binding Peptides Based on Independent Binding of Individual Peptide Side-Chains", *J Immunol.*, vol. 152, No. 1, pp. 163-175 (1994).

Rammensee, et al., "MHC ligands and peptide motifs: first listing," *Immunogenetics*, vol. 41(4), pp. 178-228 (1995).

Corresponding English document of Roitt et al., *Immunology*, 2000, pp. 159-162.

Roitt et al., *Immunology*, 2000, pp. 159-162.

Corresponding English document of Roitt et al., *Immunology*, 2000, pp. 10-13, 194, 196-199.

Roitt et al., *Immunology*, 2000, pp. 10-13, 194, 196-199.

Rosenberg, et al., "Cancer immunotherapy: moving beyond current vaccines", *Nat. Med*, vol. 10, No. 9, pp. 909-915 (2004).

Schueler-Furman, et al., "Structure-based prediction of binding peptides to MHC class I molecules: Application to a broad range of MHC alleles", *Protein Sci.*, vol. 9, No. 9, pp. 1838-1846 (2000).

Shastri et al., "Presentation of Endogenous Peptide/MHC Class I Complexes is Profoundly Influenced by Specific C-Terminal Flanking Residues", *J Immunol.*, vol. 155, No. 9, pp. 4339-4346 (1995).

Shedlock et al., "Requirement for CD4 T Cell Help in Generating Functional CD8 T Cell Memory", *Science*, vol. 300, No. 5617, pp. 337-339 (2003).

Spitler et al., "Cancer Vaccines: The Interferon Analogy", *Cancer Biother.*, vol. 10, No. 1, pp. 1-3 (1995).

Street et al., "Perforin and interferon-γ activities independently control tumor initiation, growth, and metastasis", *Blood*, vol. 97, No. 1, pp. 192-197 (2001).

Tanaka, et al., "Induction of Antitumor Cytotoxic T Lymphocytes with a MAGE-3-encoded Synthetic Peptide Presented by Human Leukocytes Antigen-A24" *Cancer Res.*, vol. 57, No. 20, pp. 4465-4468 (1997).

Tsunoda et al., U.S. Appl. No. 15/176,444, filed Jun. 8, 2016.

Tomita et al., "Identification of CDCA1-derived long peptides bearing both $CD4^+$ and $CD8^+$ T-cell epitopes: CDCA1-specific $CD4^+$ T-cell immunity in cancer patients," International Journal of Cancer, 134, 352-366 (2014).

Van Der Burg, et al., "Immunogenicity of Peptides Bound to MHC Class I Molecules Depends on the MHC-Peptide Complex Stability," *J. Immunol.*, vol. 156, No. 9, pp. 3308-3314 (1996).

Vissers, et al., "The Renal Cell Carcinoma-associated Antigen G250 Encodes a Human Leukocyte Antigen (HLA)-A2.1-restricted Epitope Recognized by Cytotoxic T Lymphocytes", *Cancer Res.*, vol. 59, No. 21, pp. 5554-5559 (1999).

Walker, "Drug Target Discovery by Gene Expression Analysis: Cell Cycle Genes", *Curr Cancer Drug Targets*, vol. 1, No. 1, pp. 73-83 (2001).

Wang et al., "A Systematic Assessment of MHC Class II Peptide Binding Predictions and Evaluation of a Consensus Approach", *PLoS Comput Biol*, vol. 4, No. 4, e1000048, 10 pages.

Wigge et al., "The Ndc80p Complex from *Saccharomyces cerevisiae* Contains Conserved Centromere Components and Has a Function in Chromosome Segregation", *J Cell Biol.*, vol. 152, No. 2, pp. 349-360 (2001).

Zaremba, et al., "Identification of an Enhancer Agonist Cytotoxic T Lymphocytes Peptide from Human Carcinoembryonic Antigen", *Cancer Res.*, vol. 57, No. 20, pp. 4570-4577 (1997).

* cited by examiner

FIG. 1B

CDCA1 (39-64): NPKPEVLHMIYMRALQ<u>*IVYGIRLEHF*</u>  (SEQ ID NO: 2)
                                   HLA-A24

CDCA1 (55-78): I<u>*VYGIRLEHFYMMPVNSEV*</u>MYPHL  (SEQ ID NO: 1)
                  HLA-A24    HLA-A2

CDCA1 (55-78)

FIG. 2B
CDCA1 (55-78)
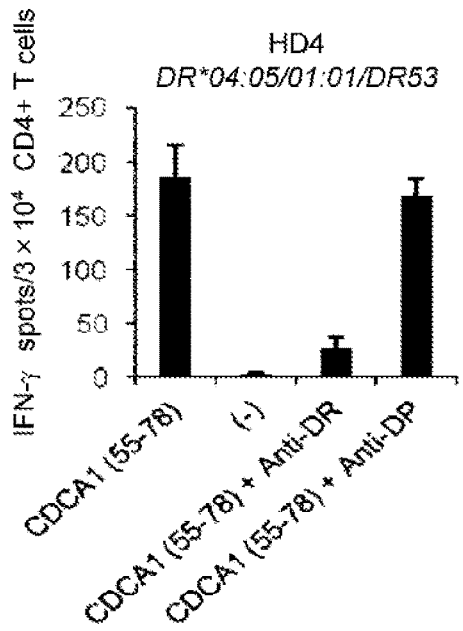
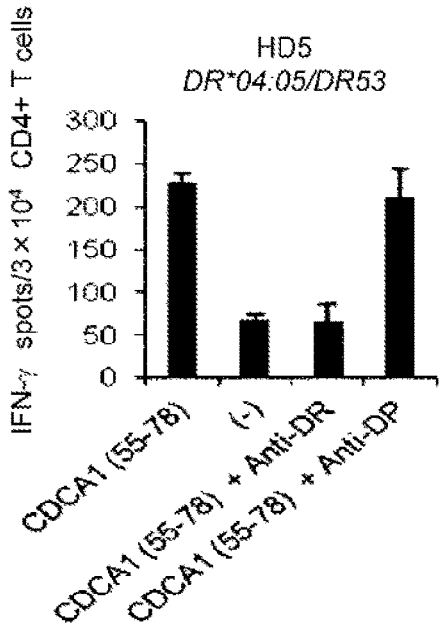
CDCA1 (39-64)
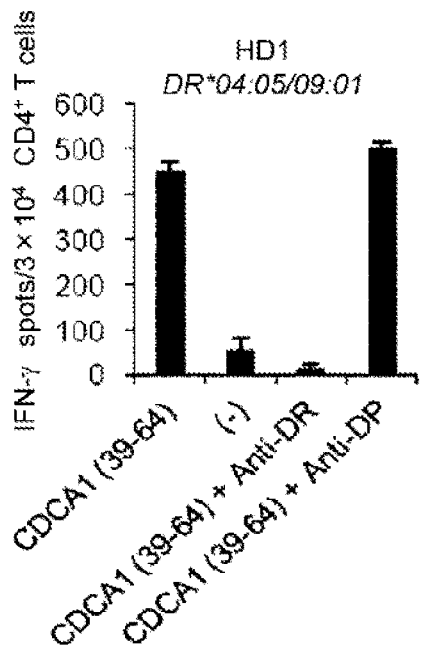
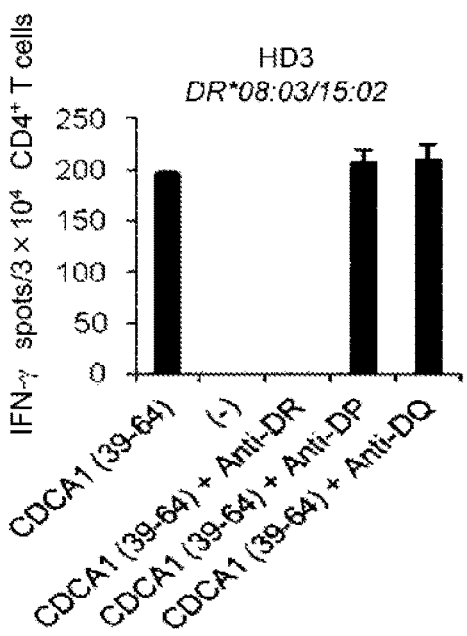
FIG. 2C FIG. 5A
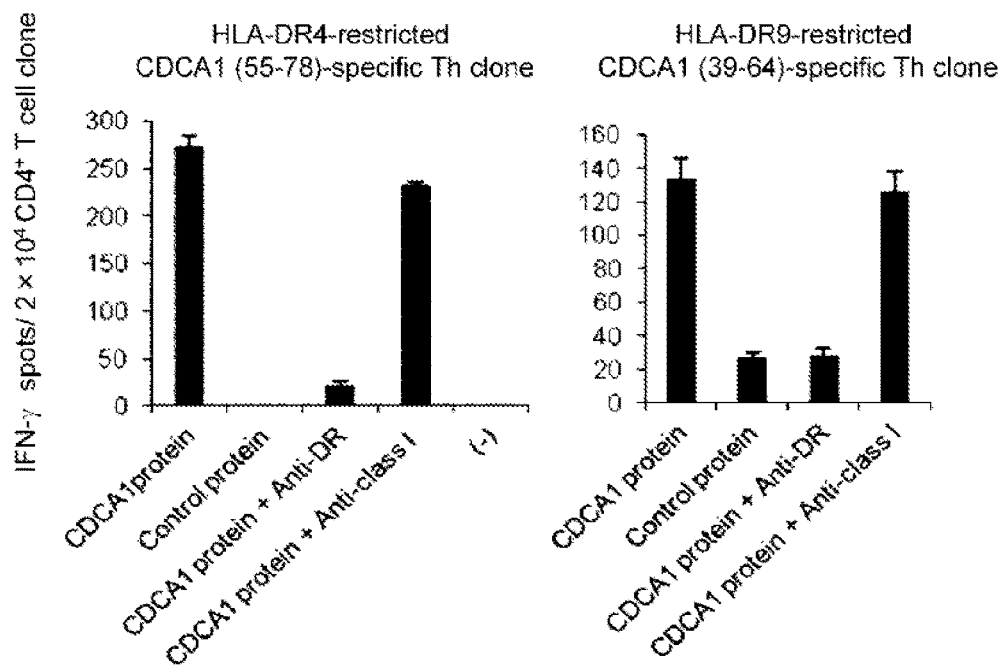
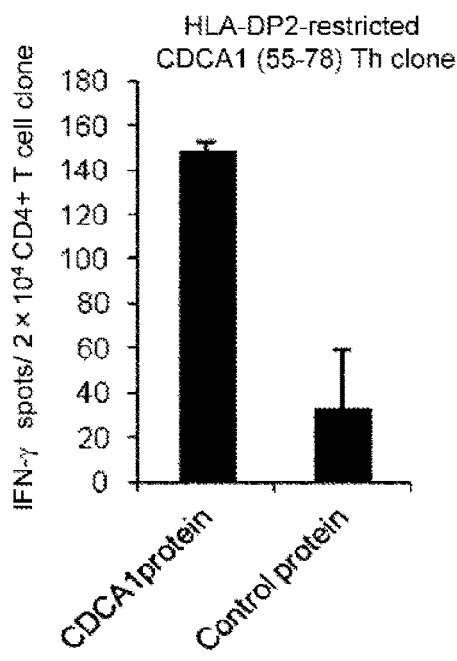
FIG. 5B FIG. 6C
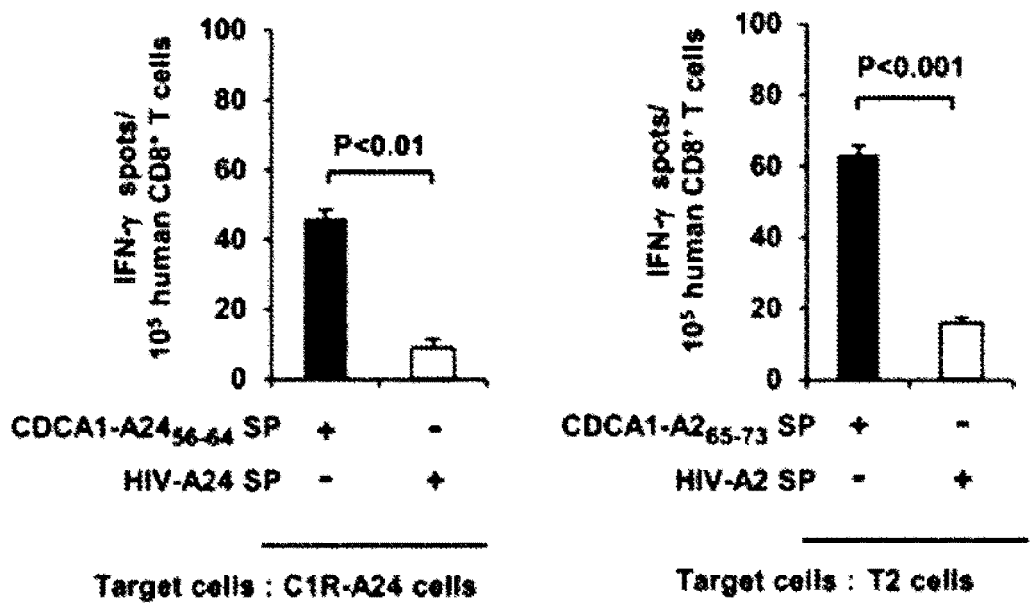
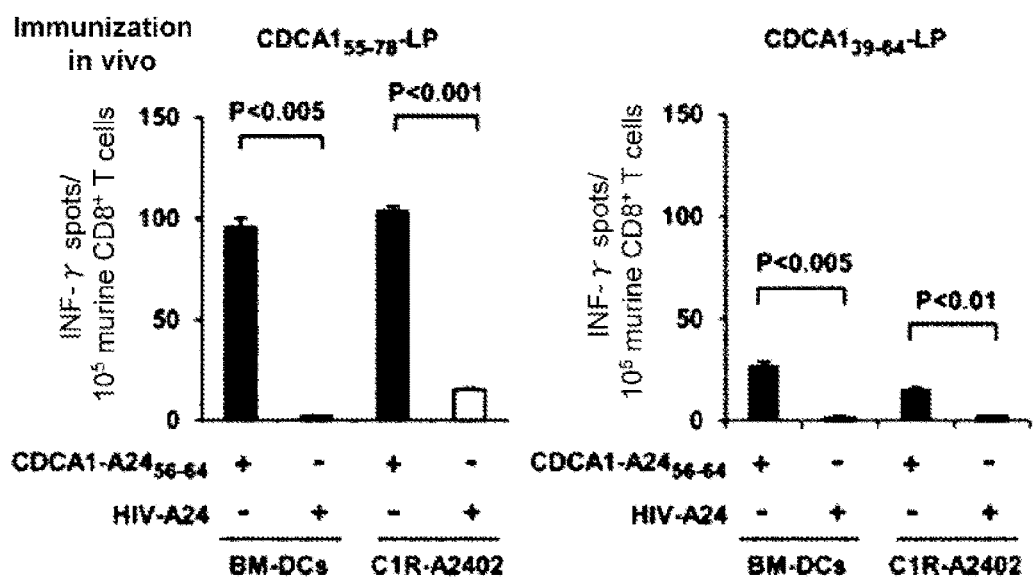
FIG. 6D

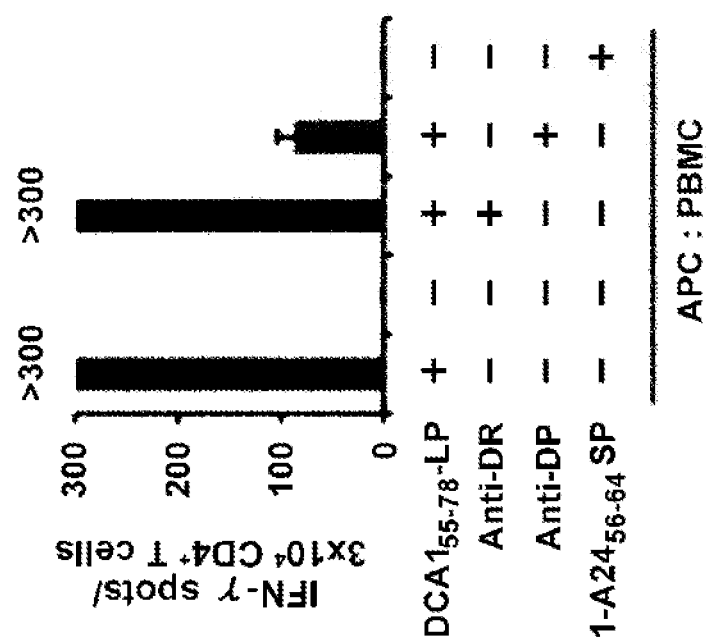
FIG. 8C1

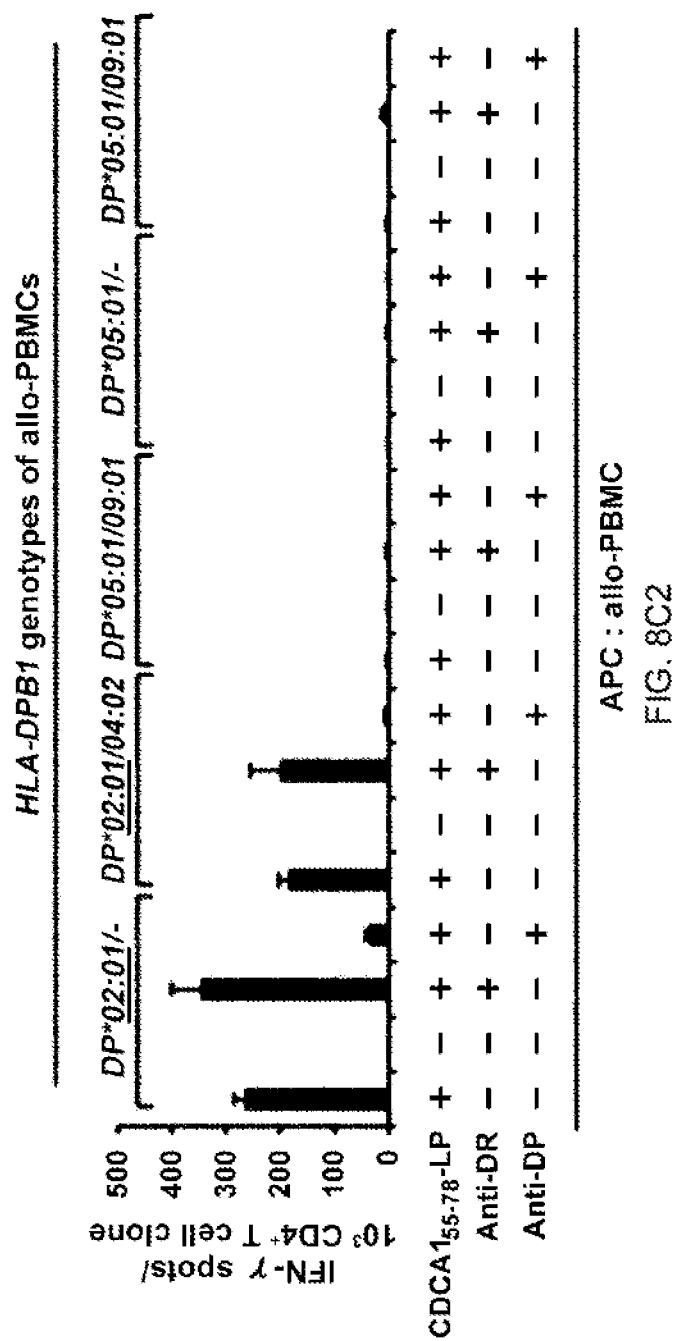
FIG. 8C2

FIG. 11A
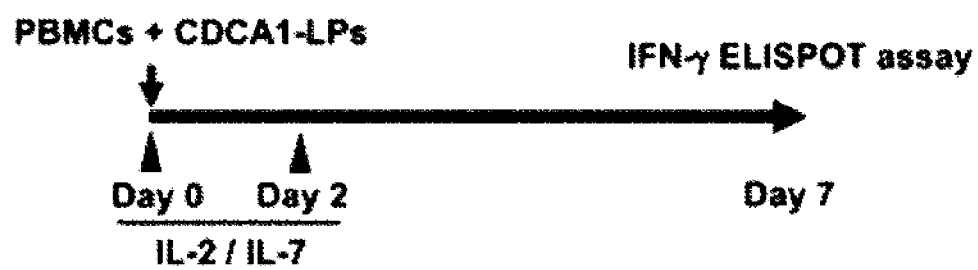
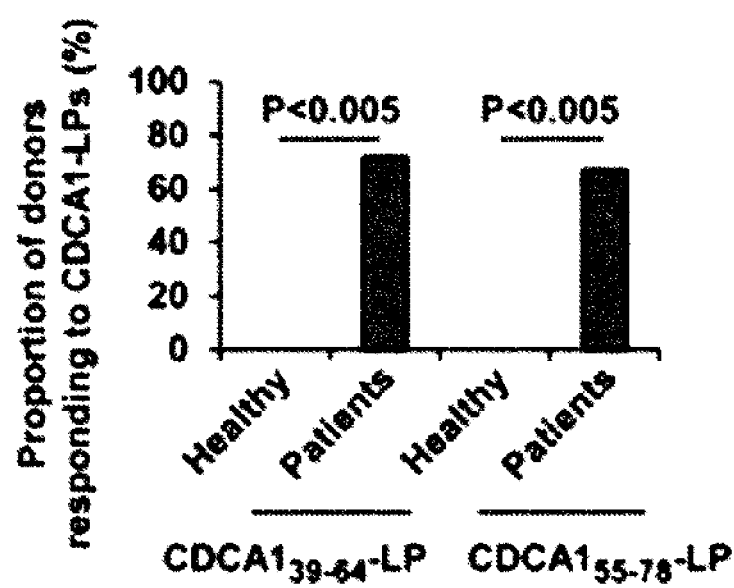
FIG. 11B

Clinical characteristics of HNC patients

| Patient ID | Age/Sex | CDCA1-specific CD4+ T-cell responses[a] | | | | No. of vaccinations | Histologic subtype | HLA-DRB1 | HLA-DPB1 |
|---|---|---|---|---|---|---|---|---|---|
| | | CDCA1₃₉₋₄₄-LP | | CDCA1₉₅₋₇₀-LP | | | | | |
| | | Pre-vac. | Post-vac. | Pre-vac. | Post-vac. | | | | |
| CTR-8379 + CTR-8380 | | | | | | | | | |
| Positive/ Total, % | | 14/19, 74% | | 13/19, 68% | | | | | |
| CTR-8379 | | Pre-vac. | Post-vac. | Pre-vac. | Post-vac. | | | | |
| Positive / Total, % | | 2/6, 33% | 7/10, 70% | 2/6, 33% | 7/10, 70% | | | | |
| HNC10 | 61/M | n.t. | + | n.t. | - | 60 | Squamous Cell Carcinoma | 01:01 / 04:05 | 06:01 / - |
| HNC20 | 57/F | n.t. | - | n.t. | - | 32 | Squamous Cell Carcinoma | 01:01 / 09:01 | 02:01 / 05:01 |
| HNC26 | 70/M | n.t. | + | n.t. | + | 24 | Basaloid Squamous Cell Carcinoma | 04:05 / 15:02 | 05:01 / 09:01 |
| HNC29 | 64/F | n.t. | + | n.t. | + | 16 | Squamous Cell Carcinoma | 09:01 / 14:54 | 03:01 / 05:01 |
| HNC31 | 69/F | n.t. | + | n.t. | + | 16 | Adenoid Cystic Carcinoma | 01:01 / 11:01 | 02:01 / 04:02 |
| HNC34 | 65/M | n.t. | + | n.t. | + | 12 | Squamous Cell Carcinoma | 08:03 / 15:02 | 02:01 / 05:01 |
| HNC35 | 85/F | n.t. | - | n.t. | + | 8 | Squamous Cell Carcinoma | 04:05 / 08:02 | 05:01 / - |
| HNC37 | 35/F | - | n.t. | - | n.t. | 0 | Adenoid Cystic Carcinoma | 04:05 / 15:02 | 02:01 / 05:01 |
| HNC38 | 56/M | - | n.t. | - | n.t. | 0 | Unknown | 09:01 / - | 02:01 / 05:01 |
| HNC39 | 77/M | - | + | - | + | 8 | Adenoid Cystic Carcinoma | 04:06 / 14:54 | 05:01 / 19:01 |
| HNC40 | 76/M | + | - | + | + | 4 | Squamous Cell Carcinoma | 01:01 / 09:01 | 04:02 / 05:01 |
| HNC41 | 51/F | + | n.t. | + | n.t. | 0 | Adenoid Cystic Carcinoma | 01:01 / 04:05 | 04:02 / 05:01 |
| HNC42 | 36/F | - | + | - | - | 4 | Unknown | 01:01 / 08:02 | 04:02 / 05:01 |
| CTR-8380 | | Pre-vac. | Post-vac. | Pre-vac. | Post-vac. | | | | |
| Positive / Total, % | | 0/1, 0% | 5/6, 83% | 0/1, 0% | 5/6, 83% | | | | |
| HNC102 | 80/F | n.t. | - | n.t. | - | 33 | Squamous Cell Carcinoma | 15:02 / - | 02:01 / 09:01 |
| HNC103 | 78/F | n.t. | + | n.t. | + | 20 | Mucinous Adenocarcinoma | 04:05 / 15:01 | 02:01 / 05:01 |
| HNC105 | 65/M | n.t. | + | n.t. | + | 20 | Angiosarcoma | 04:05 / 13:02 | 03:01 / 04:01 |
| HNC107 | 20/M | n.t. | + | n.t. | + | 20 | Osteosarcoma | 09:01 / - | 02:01 / 02:02 |
| HNC108 | 41/M | n.t. | + | n.t. | + | 8 | Osteosarcoma | 04:05 / 09:01 | 05:01 / - |
| HNC109 | 72/F | - | - | - | - | 4 | Verrucous Carcinoma | 04:10 / 15:02 | 03:01 / 09:01 |

FIG. 11F

SEQUENCE LISTING

```
<160> NUMBER OF SEQ ID NOS: 10

<210> SEQ ID NO 1
<211> LENGTH: 24
<212> TYPE: PRT
<213> ORGANISM: Artificial Sequence
<220> FEATURE:
<223> OTHER INFORMATION: An artificially synthesized peptide

<400> SEQUENCE: 1

Ile Val Tyr Gly Ile Arg Leu Glu His Phe Tyr Met Met Pro Val Asn
1               5                   10                  15

Ser Glu Val Met Tyr Pro His Leu
            20

<210> SEQ ID NO 2
<211> LENGTH: 26
<212> TYPE: PRT
<213> ORGANISM: Artificial Sequence
<220> FEATURE:
<223> OTHER INFORMATION: An artificially synthesized peptide

<400> SEQUENCE: 2

Asn Pro Lys Pro Glu Val Leu His Met Ile Tyr Met Arg Ala Leu Gln
1               5                   10                  15

Ile Val Tyr Gly Ile Arg Leu Glu His Phe
            20                  25

<210> SEQ ID NO 3
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 3

Tyr Met Met Pro Val Asn Ser Glu Val
1               5

<210> SEQ ID NO 4
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 4

Lys Leu Ala Thr Ala Gln Phe Lys Ile
1               5

<210> SEQ ID NO 5
<211> LENGTH: 9
<212> TYPE: PRT
<213> ORGANISM: Artificial Sequence
```

```
<220> FEATURE:
<223> OTHER INFORMATION: HLA-A24 epitope peptide

<400> SEQUENCE: 5

Val Tyr Gly Ile Arg Leu Glu His Phe
1               5

<210> SEQ ID NO 6
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 6

Arg Tyr Leu Arg Asp Gln Gln Leu Leu
1               5

<210> SEQ ID NO 7
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 7

Ser Leu Tyr Asn Thr Tyr Ala Thr Leu
1               5

<210> SEQ ID NO 8
<211> LENGTH: 16
<212> TYPE: PRT
<213> ORGANISM: Artificial Sequence
<220> FEATURE:
<223> OTHER INFORMATION: An artificially synthesized peptide

<400> SEQUENCE: 8

Lys Arg Tyr Phe Lys Leu Ser His Leu Gln Met His Ser Arg Lys His
1               5                   10                  15

<210> SEQ ID NO 9
<211> LENGTH: 1989
<212> TYPE: DNA
<213> ORGANISM: Homo sapiens
<220> FEATURE:
<221> NAME/KEY: CDS
<222> LOCATION: (301)..(1695)

<400> SEQUENCE: 9
gcggaatggg gcgggacttc cagtaggagg cggcaagttt gaaaagtgat gacggttgac      60
gtttgctgat tttttgacttt gcttgtagct gctccccgaa ctcgccgtct tcctgtcggc     120
ggccggcact gtaggtgagc gcgagaggac ggaggaagga agcctgcaga cagacgcctt     180
ctccatccca aggcgcgggc aggtgccggg acgctgggcc tggcggtgtt ttcgtcgtgc     240
tcagcggtgg gaggaggcgg aagaaaccag agcctgggag attaacagga aacttccaag     300 atg gaa act ttg tct ttc ccc aga tat aat gta gct gag att gtg att      348
Met Glu Thr Leu Ser Phe Pro Arg Tyr Asn Val Ala Glu Ile Val Ile
1               5                   10                  15 cat att cgc aat aag atc tta aca gga gct gat ggt aaa aac ctc acc      396
His Ile Arg Asn Lys Ile Leu Thr Gly Ala Asp Gly Lys Asn Leu Thr
                20                  25                  30 aag aat gat ctt tat cca aat cca aag cct gaa gtc ttg cac atg atc      444
Lys Asn Asp Leu Tyr Pro Asn Pro Lys Pro Glu Val Leu His Met Ile
            35                  40                  45
```

| | | |
|---|---|---|
| tac atg aga gcc tta caa ata gta tat gga att cga ctg gaa cat ttt<br>Tyr Met Arg Ala Leu Gln Ile Val Tyr Gly Ile Arg Leu Glu His Phe<br>50        55                 60 | | 492 |
| tac atg atg cca gtg aac tct gaa gtc atg tat cca cat tta atg gaa<br>Tyr Met Met Pro Val Asn Ser Glu Val Met Tyr Pro His Leu Met Glu<br>65             70                 75                  80 | | 540 |
| ggc ttc tta cca ttc agc aat tta gtt act cat ctg gac tca ttt ttg<br>Gly Phe Leu Pro Phe Ser Asn Leu Val Thr His Leu Asp Ser Phe Leu<br>              85                  90                  95 | | 588 |
| cct atc tgc cgg gtg aat gac ttt gag act gct gat att cta tgt cca<br>Pro Ile Cys Arg Val Asn Asp Phe Glu Thr Ala Asp Ile Leu Cys Pro<br>         100                 105                 110 | | 636 |
| aaa gca aaa cgg aca agt cgg ttt tta agt ggc att atc aac ttt att<br>Lys Ala Lys Arg Thr Ser Arg Phe Leu Ser Gly Ile Ile Asn Phe Ile<br>     115                 120                 125 | | 684 |
| cac ttc aga gaa gca tgc cgt gaa acg tat atg gaa ttt ctt tgg caa<br>His Phe Arg Glu Ala Cys Arg Glu Thr Tyr Met Glu Phe Leu Trp Gln<br>130                 135                 140 | | 732 |
| tat aaa tcc tct gcg gac aaa atg caa cag tta aac gcc gca cac cag<br>Tyr Lys Ser Ser Ala Asp Lys Met Gln Gln Leu Asn Ala Ala His Gln<br>145                 150                 155                 160 | | 780 |
| gag gca tta atg aaa ctg gag aga ctt gat tct gtt cca gtt gaa gag<br>Glu Ala Leu Met Lys Leu Glu Arg Leu Asp Ser Val Pro Val Glu Glu<br>                165                 170                 175 | | 828 |
| caa gaa gag ttc aag cag ctt tca gat gga att cag gag cta caa caa<br>Gln Glu Glu Phe Lys Gln Leu Ser Asp Gly Ile Gln Glu Leu Gln Gln<br>            180                 185                 190 | | 876 |
| tca cta aat cag gat ttt cat caa aaa acg ata gtg ctg caa gag gga<br>Ser Leu Asn Gln Asp Phe His Gln Lys Thr Ile Val Leu Gln Glu Gly<br>        195                 200                 205 | | 924 |
| aat tcc caa aag aag tca aat att tca gag aaa acc aag cgt ttg aat<br>Asn Ser Gln Lys Lys Ser Asn Ile Ser Glu Lys Thr Lys Arg Leu Asn<br>    210                 215                 220 | | 972 |
| gaa cta aaa ttg tcg gtg gtt tct ttg aaa gaa ata caa gag agt ttg<br>Glu Leu Lys Leu Ser Val Val Ser Leu Lys Glu Ile Gln Glu Ser Leu<br>225                 230                 235                 240 | | 1020 |
| aaa aca aaa att gtg gat tct cca gag aag tta aag aat tat aaa gaa<br>Lys Thr Lys Ile Val Asp Ser Pro Glu Lys Leu Lys Asn Tyr Lys Glu<br>                245                 250                 255 | | 1068 |
| aaa atg aaa gat acg gtc cag aag ctt aaa aat gcc aga caa gaa gtg<br>Lys Met Lys Asp Thr Val Gln Lys Leu Lys Asn Ala Arg Gln Glu Val<br>            260                 265                 270 | | 1116 |
| gtg gag aaa tat gaa atc tat gga gac tca gtt gac tgc ctg cct tca<br>Val Glu Lys Tyr Glu Ile Tyr Gly Asp Ser Val Asp Cys Leu Pro Ser<br>        275                 280                 285 | | 1164 |
| tgt cag ttg gaa gtg cag tta tat caa aag aaa ata cag gac ctt tca<br>Cys Gln Leu Glu Val Gln Leu Tyr Gln Lys Lys Ile Gln Asp Leu Ser<br>    290                 295                 300 | | 1212 |
| gat aat agg gaa aaa tta gcc agt atc tta aag gag agc ctg aac ttg<br>Asp Asn Arg Glu Lys Leu Ala Ser Ile Leu Lys Glu Ser Leu Asn Leu<br>305                 310                 315                 320 | | 1260 |
| gag gac caa att gag agt gat gag tca gaa ctg aag aaa ttg aag act<br>Glu Asp Gln Ile Glu Ser Asp Glu Ser Glu Leu Lys Lys Leu Lys Thr<br>                325                 330                 335 | | 1308 |
| gaa gaa aat tcg ttc aaa aga ctg atg att gtg aag aag gaa aaa ctt<br>Glu Glu Asn Ser Phe Lys Arg Leu Met Ile Val Lys Lys Glu Lys Leu<br>            340                 345                 350 | | 1356 |
| gcc aca gca caa ttc aaa ata aat aag aag cat gaa gat gtt aag caa<br>Ala Thr Ala Gln Phe Lys Ile Asn Lys Lys His Glu Asp Val Lys Gln<br>        355                 360                 365 | | 1404 |

```
tac aaa cgc aca gta att gag gat tgc aat aaa gtt caa gaa aaa aga      1452
Tyr Lys Arg Thr Val Ile Glu Asp Cys Asn Lys Val Gln Glu Lys Arg
    370                 375                 380 ggt gct gtc tat gaa cga gta acc aca att aat caa gaa atc caa aaa      1500
Gly Ala Val Tyr Glu Arg Val Thr Thr Ile Asn Gln Glu Ile Gln Lys
385                 390                 395                 400 att aaa ctt gga att caa caa cta aaa gat gct gct gaa agg gag aaa      1548
Ile Lys Leu Gly Ile Gln Gln Leu Lys Asp Ala Ala Glu Arg Glu Lys
                405                 410                 415 ctg aag tcc cag gaa ata ttt cta aac ttg aaa act gct ttg gag aaa      1596
Leu Lys Ser Gln Glu Ile Phe Leu Asn Leu Lys Thr Ala Leu Glu Lys
            420                 425                 430 tac cac gac ggt att gaa aag gca gca gag gac tcc tat gct aag ata      1644
Tyr His Asp Gly Ile Glu Lys Ala Ala Glu Asp Ser Tyr Ala Lys Ile
        435                 440                 445 gat gag aag aca gct gaa ctg aag agg aag atg ttc aaa atg tca acc      1692
Asp Glu Lys Thr Ala Glu Leu Lys Arg Lys Met Phe Lys Met Ser Thr
    450                 455                 460 tga ttaacaaaat tacatgtctt tttgtaaatg gcttgccatc ttttaatttt           1745
ctatttagaa agaaaagttg aagcgaatgg aagtatcaga agtaccaaat aatgttggct    1805
tcatcagttt ttatacactc tcataagtag ttaataagat gaatttaatg taggctttta    1865
ttaatttata attaaaataa cttgtgcagc tattcatgtc tctactctgc cccttgttgt    1925
aaatagtttg agtaaaacaa aactagttac ctttgaaata tatatatttt tttctgttac    1985
tatc                                                                 1989

<210> SEQ ID NO 10
<211> LENGTH: 464
<212> TYPE: PRT
<213> ORGANISM: Homo sapiens

<400> SEQUENCE: 10

Met Glu Thr Leu Ser Phe Pro Arg Tyr Asn Val Ala Glu Ile Val Ile
1               5                   10                  15

His Ile Arg Asn Lys Ile Leu Thr Gly Ala Asp Gly Lys Asn Leu Thr
            20                  25                  30

Lys Asn Asp Leu Tyr Pro Asn Pro Lys Pro Glu Val Leu His Met Ile
        35                  40                  45

Tyr Met Arg Ala Leu Gln Ile Val Tyr Gly Ile Arg Leu Glu His Phe
    50                  55                  60

Tyr Met Met Pro Val Asn Ser Glu Val Met Tyr Pro His Leu Met Glu
65                  70                  75                  80

Gly Phe Leu Pro Phe Ser Asn Leu Val Thr His Leu Asp Ser Phe Leu
                85                  90                  95

Pro Ile Cys Arg Val Asn Asp Phe Glu Thr Ala Asp Ile Leu Cys Pro
            100                 105                 110

Lys Ala Lys Arg Thr Ser Arg Phe Leu Ser Gly Ile Ile Asn Phe Ile
        115                 120                 125

His Phe Arg Glu Ala Cys Arg Glu Thr Tyr Met Glu Phe Leu Trp Gln
    130                 135                 140

Tyr Lys Ser Ser Ala Asp Lys Met Gln Gln Leu Asn Ala Ala His Gln
145                 150                 155                 160

Glu Ala Leu Met Lys Leu Glu Arg Leu Asp Ser Val Pro Val Glu Glu
                165                 170                 175

Gln Glu Glu Phe Lys Gln Leu Ser Asp Gly Ile Gln Glu Leu Gln Gln
            180                 185                 190
```

-continued

```
Ser Leu Asn Gln Asp Phe His Gln Lys Thr Ile Val Leu Gln Glu Gly
        195                 200                 205

Asn Ser Gln Lys Lys Ser Asn Ile Ser Glu Lys Thr Lys Arg Leu Asn
        210                 215                 220

Glu Leu Lys Leu Ser Val Val Ser Leu Lys Glu Ile Gln Glu Ser Leu
225                 230                 235                 240

Lys Thr Lys Ile Val Asp Ser Pro Glu Lys Leu Lys Asn Tyr Lys Glu
                245                 250                 255

Lys Met Lys Asp Thr Val Gln Lys Leu Lys Asn Ala Arg Gln Glu Val
                260                 265                 270

Val Glu Lys Tyr Glu Ile Tyr Gly Asp Ser Val Asp Cys Leu Pro Ser
        275                 280                 285

Cys Gln Leu Glu Val Gln Leu Tyr Gln Lys Lys Ile Gln Asp Leu Ser
        290                 295                 300

Asp Asn Arg Glu Lys Leu Ala Ser Ile Leu Lys Glu Ser Leu Asn Leu
305                 310                 315                 320

Glu Asp Gln Ile Glu Ser Asp Glu Ser Glu Leu Lys Lys Leu Lys Thr
                325                 330                 335

Glu Glu Asn Ser Phe Lys Arg Leu Met Ile Val Lys Lys Glu Lys Leu
                340                 345                 350

Ala Thr Ala Gln Phe Lys Ile Asn Lys Lys His Glu Asp Val Lys Gln
            355                 360                 365

Tyr Lys Arg Thr Val Ile Glu Asp Cys Asn Lys Val Gln Glu Lys Arg
        370                 375                 380

Gly Ala Val Tyr Glu Arg Val Thr Thr Ile Asn Gln Glu Ile Gln Lys
385                 390                 395                 400

Ile Lys Leu Gly Ile Gln Gln Leu Lys Asp Ala Ala Glu Arg Glu Lys
                405                 410                 415

Leu Lys Ser Gln Glu Ile Phe Leu Asn Leu Lys Thr Ala Leu Glu Lys
                420                 425                 430

Tyr His Asp Gly Ile Glu Lys Ala Ala Glu Asp Ser Tyr Ala Lys Ile
        435                 440                 445

Asp Glu Lys Thr Ala Glu Leu Lys Arg Lys Met Phe Lys Met Ser Thr
450                 455                 460
```

CDCA1 EPITOPE PEPTIDES FOR TH1 CELLS AND VACCINES CONTAINING THE SAME

CROSS REFERENCE TO RELATED APPLICATIONS

The present application is a Divisional of U.S. application Ser. No. 14/413,413, filed Jan. 7, 2015, which is a 371 Application of PCT/JP2013/004244, filed Jul. 9, 2013, which claims the benefit of U.S. Provisional Application No. 61/669,971, filed on Jul. 10, 2012, the entire contents of which are incorporated by reference herein.

TECHNICAL FIELD

The present invention relates to the field of biological science, more specifically to the field of cancer therapy. In particular, the present invention relates to novel peptides that are extremely effective as cancer vaccines, and drugs for either or both of treating and preventing tumors.

REFERENCE TO SEQUENCE LISTING

This application includes a Sequence Listing as a text file named "87331-1033118-SEQLIST.txt" created Jan. 19, 2017, and containing 14,024 bytes. The material contained in this text file is incorporated by reference in its entirety for all purposes.

BACKGROUND ART

CD8 positive cytotoxic T lymphocytes (CTLs) have been shown to recognize epitope peptides derived from the tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered, primarily through immunological approaches (NPL 1, 2). Some of these TAAs are currently undergoing clinical development as immunotherapeutic targets.

TAAs which are indispensable for proliferation and survival of cancer cells are valiant as targets for immunotherapy, because the use of such TAAs may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses warrants further development. Thus, the clinical application of peptide vaccination strategies for various types of cancer is ongoing (NPL 3-10). To date, there have been several reports of clinical trials using these tumor-associated antigen derived peptides. Unfortunately, so far, these cancer vaccine trials have yielded only a low objective response rate has been observed in these cancer vaccine trials so far (NPL 11-13). Accordingly, there remains a need in the art for new TAAs suitable for use as immunotherapeutic targets.

The CDCA1 gene, also known as cell division cycle associated 1, has been identified as a member of a class of genes that are coexpressed with cell cycle genes, such as CDC2, cyclin, topoisomerase II and the others (NPL 14). CDCA1 in particular was found to be associated with centromeres of mitotic HeLa cells and was therefore considered a functional homologue of yeast Nuf2 (NPL 15).

In addition, through gene expression profile analysis using a genome-wide cDNA microarray containing 23,040 genes (NPL 16), CDCA1 has also been identified as a novel molecule up-regulated in breast cancer (PTL 1), bladder cancer (PTL 2), esophageal cancer (PTL 3), small cell lung cancer (SCLC) and non-small cell lung cancer (NSCLC) (PTL 4), the contents of such disclosure being incorporated by reference herein. Expression of CDCA1 was found to be particularly up-regulated in SCLC, NSCLC and tumor cell lines, though no expression was detected except testis among 23 normal tissues. Furthermore, down-regulation of CDCA1 expression by siRNA has been shown to cause cell growth suppression in CDCA1 expressing lung cancer cell lines (PTL 4).

Taken together, these data suggest that CDCA1 is a novel, potentially universal oncoantigen. Accordingly, epitope peptides derived from CDCA1 may be applicable as cancer immunotherapeutics for the treatment of a wide array of cancers.

Recently, highly immunogenic CDCA1-derived cytotoxic T lymphocytes (CTL)-epitopes that can induce tumor-reactive and HLA-A2 (A*02:01)-restricted CTL from PBMCs of lung cancer patients (NPL 17, PTL 6) have been identified. Furthermore, CDCA1-derived HLA-A24-restricted CTL-epitopes have been also identified (PTL 7). Therefore, CDCA1 remains an attractive target molecule applicable to cancer immunotherapy.

Tumor-specific $CD4^+$ helper T (Th) cells, especially T-helper type 1 (Th1) cells play a critical role in efficient induction of CTL-mediated antitumor immunity (NPL 18). The IFN-gamma primarily produced by Th1 cells is critical for induction and maintenance of long lived CTL responses, providing help through multiple interactions which are critical in the preservation of immunological memory (NPL 19, 20). The IFN-gamma secreted by Th1 cells also mediates direct antitumor or anti-angiogenic effect (NPL 21). Furthermore, it has been shown that Th cells must pave the way for entry of CTLs at tumor site (NPL 22). Therefore, identification of tumor-associated antigen (TAA)-derived Th cell epitopes that can activate specific Th1 cell is important for induction of an effective tumor immunity in tumor-bearing hosts; ideally, the design of effective vaccines should include multiple epitopes to stimulate both CTL and Th1 cells (NPL 23). However, no such epitope derived from CDCA1 has yet been identified.

CITATION LIST

Patent Literature

[PTL 1] WO2005/028676
[PTL 2] WO2006/085684
[PTL 3] WO2007/013671
[PTL 4] WO2007/013665
[PTL 5] WO2005/089735
[PTL 6] WO2009/025117
[PTL 7] WO2009/153992

Non Patent Literature

[NPL 1] Boon T, Int. J. Cancer 1993 May 8, 54(2): 177-80
[NPL 2] Boon T and van der Bruggen P, J. Exp. Med. 1996 Mar. 1, 183(3): 725-9
[NPL 3] Harris C C, J. Natl. Cancer Inst. 1996 Oct. 16, 88(20): 1442-55
[NPL 4] Butterfield L H et al., Cancer Res. 1999 Jul. 1, 59(13): 3134-42

[NPL 5] Vissers J L et al., Cancer Res. 1999 Nov. 1, 59(21): 5554-9
[NPL 6] van der Burg S H et al., J. Immunol. 1996 May 1, 156(9): 3308-14
[NPL 7] Tanaka F et al., Cancer Res. 1997 Oct. 15, 57(20): 4465-8
[NPL 8] Fujie T et al., Int. J. Cancer 1999 Jan. 18, 80(2): 169-72
[NPL 9] Kikuchi M et al., Int. J. Cancer 1999 May 5, 81(3): 459-66
[NPL 10] Oiso M et al., Int. J. Cancer 1999 May 5, 81(3): 387-94
[NPL 11] Belli F et al., J. Clin. Oncol. 2002 Oct. 15, 20(20): 4169-80
[NPL 12] Coulie P G et al., Immunol. Rev 2002 October, 188: 33-42
[NPL 13] Rosenberg S A et al., Nat. Med. 2004 September, 10(9): 909-15
[NPL 14] Walker et al., Curr. Cancer Drug Targets 2001 May; 1(1):73-83
[NPL 15] J. Cell. Biol. 2001 Jan. 22; 152(2):349-60
[NPL 16] Cancer Res. 2006 Nov. 1; 66(21):10339-48
[NPL 17] Harao M et al. Int. J. Cancer 2008; 123: 2616-25.
[NPL 18] Chamoto K et al. Cancer Res. 2004; 64: 386-90.
[NPL 19] Bevan M J. Nat. Rev. Immunol. 2004; 4: 595-602.
[NPL 20] Shedlock D J and Shen H. Science 2003; 300: 337-9.
[NPL 21] Street S E et al. Blood 2001; 97: 192-7.
[NPL 22] Bos R, and Sherman L A. Cancer Res. 2010; 70: 8368-77.
[NPL 23] Melief C J et al. Nat. Rev. Cancer 2008; 8: 351-60.

SUMMARY OF INVENTION

In the context of the present invention, the present inventors considered an ideal peptide vaccine for cancer immunotherapy to be one that includes a single polypeptide containing epitopes for both CTL and Th1 cell, both of which are naturally proximal to each other (Kenter G G et al. N. Engl. J. Med. 2009; 361: 1838-47.).

To that end, the present inventors designed a strategy to identify novel CDCA1-derived Th1 cell epitopes recognized in the context of promiscuous HLA class II molecules and containing CTL epitopes, working on the presumption that epitopes so characterized would induce more efficient T cell-mediated tumor immunity. A computer algorithm predicting HLA class II-binding peptides and known CTL epitope sequences recognized by HLA-A24 (A*24:02) or A2-restricted CTLs was used to select candidate promiscuous HLA-class II-restricted Th1 cell epitopes containing CTL epitopes.

The present invention is based, at least in part, on the discovery of suitable epitope peptides that serve as targets of immunotherapy for inducing Th1 cell response. Recognizing that the CDCA1 gene is up-regulated in a number of cancer types, including breast cancer, bladder cancer, non-small cell lung cancer, small cell lung cancer, esophageal cancer and head and neck cancer, the present invention targets for further analysis the gene product of cell division cycle associated 1 (CDCA1) gene, more particularly the polypeptide set forth in SEQ ID NO: 10 encoded by the gene of GenBank Accession No. NM_145697 (SEQ ID NO: 9)). CDCA1 gene products containing epitope peptides that elicit Th1 cells specific to the corresponding molecule were particularly selected for further study. For example, peripheral blood mononuclear cells (PBMCs) obtained from a healthy donor were stimulated using promiscuous HLA-DRs and/or DPs binding peptide derived from human CDCA1. Th1 cells that recognize HLA-DRs or DPs positive target cells pulsed with the respective candidate peptides were established, and HLA-DRs and/or DPs restricted epitope peptides that can induce potent and specific immune responses against CDCA1 were identified. These results demonstrate that CDCA1 is strongly immunogenic and the epitopes thereof are effective for tumor immunotherapy mediated through Th1 cell response. Additional studies revealed that the promiscuous HLA-DRs and/or DPs binding peptides containing at least one CTL epitope can also stimulate CTL response in the same donor in a CDCA1 specific manner. These results confirm that CDCA1 is strongly immunogenic and that epitopes thereof containing both Th1 cell and CTL epitopes are effective for tumor immunotherapy mediated through both Th1 cell and CTL responses.

It is therefore an object of the present invention to provide peptides having Th1 cell inducibility as well as an amino acid sequence selected from among SEQ ID NOs: 1 and 2. The present invention contemplates modified peptides, i.e., peptides having Th1 cell inducibility that are up to 30 amino acids in length and have a contiguous amino acid sequence selected from the amino acid sequence of SEQ ID NO: 10 (CDCA1), as well as functional equivalents thereof. Alternatively, the present invention also provides peptides having both Th1 cell and CTL inducibilities. In some embodiments, the peptides of the present invention correspond to the amino acid sequence of SEQ ID NO: 1 or 2 or modified versions thereof, in which one, two or several amino acids are substituted, deleted, inserted and/or added, while the ability to induce Th1 cells is maintained.

When administered to a subject, the present peptides are preferably presented on the surface of one or more antigen-presenting cells that in turn induce Th1 cells. When the peptide of the present invention further contains at least one CTL epitope, such APCs also process the peptides to present CTL epitopes generated from the present peptides, and thus induce CTLs targeting the respective peptides. Therefore, it is a further object of the present invention to provide antigen-presenting cells presenting any of the present peptides or fragments thereof, as well as methods for inducing antigen-presenting cells.

Administration of one or more peptides of the present invention or polynucleotide(s) encoding such peptides, or antigen-presenting cells which present such peptides or fragments thereof results in the induction of a strong anti-tumor immune response. Accordingly, it is yet another object of the present invention to provide pharmaceutical agents or compositions that contain as active ingredient(s) one or more of the following: (a) one or more peptides of the present invention, (b) one or more polynucleotides encoding such peptide(s), and (c) one or more antigen-presenting cells of the present invention. Such pharmaceutical agents or compositions of the present invention find particular utility as vaccines.

It is yet a further object of the present invention to provide methods for the treatment and/or prophylaxis (i.e., prevention) of cancers (i.e., tumors), and/or prevention of a post-operative recurrence thereof. Methods for inducing Th1 cells or for inducing anti-tumor immunity that include the step of administering one or more peptides, polynucleotides, antigen-presenting cells or pharmaceutical agents or compositions of the present invention are also contemplated. Furthermore, the Th1 cells of the present invention also find use as vaccines against cancer, examples of which include, but are not limited to, breast cancer, bladder cancer, esophageal cancer, small cell lung cancer (SCLC), non-small cell lung cancer (NSCLC) and head and neck cancer (HNC).

Examples of specifically contemplated objects of the present invention include the following:

[1] An isolated peptide having 10-30 amino acids in length and comprising a part of the amino acid sequence of SEQ ID NO: 10, wherein said peptide comprises an amino acid sequence selected from the group consisting of:
(a) a contiguous amino acid sequence having more than 9 amino acids in length selected from the amino acid sequence of SEQ ID NO: 1 or 2; and
(b) an amino acid sequence in which one, two or several amino acids are substituted, deleted, inserted, and/or added in the amino acid sequence of (a),
wherein said peptide has ability to induce T helper type 1 (Th1) cells.

[2] The isolated peptide of [1], wherein the peptide or fragment thereof has abilities to bind at least two kinds of MHC class II molecules.

[3] The isolated peptide of [2], wherein the MHC class II molecules are selected from the group consisting of HLA-DR4, HLA-DR9, HLA-DR15 and HLA-DP2.

[4] The isolated peptide of any one of [1] to [3], wherein said peptide comprises an amino acid sequence of a peptide having CDCA1-specific cytotoxic T lymphocyte (CTL) inducibility.

[5] The isolated peptide of [4], wherein said peptide comprises the amino acid sequence selected from the group consisting of:
(a) an amino acid sequence selected from the group consisting of SEQ ID NOs: 1 and 2; and
(b) an amino acid sequence in which one, two or several amino acids are substituted, deleted, inserted, and/or added in the amino acid sequence of (a).

[6] An isolated polynucleotide encoding the peptide of any one of [1] to [5].

[7] A composition for inducing at least one of the cells selected from the group consisting of
(i) Th1 cells,
(ii) CTLs,
(iii) antigen-presenting cells (APCs) having an ability to induce Th1 cells, and
(iv) APCs having an ability to induce CTLs,
wherein the composition comprises one or more peptide(s) of any one of [1] to [5], or one or more polynucleotide(s) encoding them, or a composition for inducing at least one type of cell selected from the group consisting of
(i) Th1 cells,
(ii) CTLs,
(iii) antigen-presenting cells (APCs) having an ability to induce Th1 cells, and
(iv) APCs having an ability to induce CTLs,
wherein the composition comprises one or more peptide(s) of any one of [1] to [5], or one or more polynucleotide(s) encoding them.

[8] A pharmaceutical composition, wherein the composition comprises at least one active ingredient selected from the group consisting of:
(a) one or more peptide(s) of any one of [1] to [5];
(b) one or more polynucleotide(s) of [6];
(c) one or more APC(s) presenting the peptide of any one of [1] to [5] or fragment thereof on their surface;
(d) one or more Th1 cells that recognize(s) an APC presenting the peptide of any one of [1] to [5] or fragment thereof on its surface; and
(e) combination of any two or more of (a) to (d) above; and is formulated for a purpose selected from the group consisting of:
(i) cancer treatment,
(ii) cancer prevention,
(iii) prevention of post-operative recurrence in cancer, and
(iv) combinations of any two or more of (i) to (iii) above.

[9] The pharmaceutical composition of [8], wherein said composition is formulated for administration to a subject that has at least one selected from the group consisting of HLA-DR4, HLA-DR9, HLA-DR15 and HLA-DP2 as a MHC class II molecule, or the pharmaceutical composition of [8], wherein said composition is formulated for administration to a subject that has at least one MHC class II molecule selected from the group consisting of HLA-DR4, HLA-DR9, HLA-DR15 and HLA-DP2.

[10] The pharmaceutical composition of [8] or [9], wherein said composition further comprises one or more peptides having CTL inducibility.

[11] A composition for enhancing an immune response mediated with an MHC class II molecule, wherein the composition comprises at least one active ingredient selected from the group consisting of:
(a) one or more peptide(s) of any one of [1] to [5];
(b) one or more polynucleotide(s) of [6];
(c) one or more APC(s) presenting the peptide of any one of [1] to [5] or fragment thereof on their surface;
(d) one or more Th1 cell(s) that recognize(s) an APC presenting the peptide of any one of [1] to [5] or fragment thereof on its surface; and
(e) combination of any two or more of (a) to (d) above.

[12] A method for inducing an APC having an ability to induce a Th1 cell, said method comprising a step of contacting an APC with the peptide of any one of [1] to [5] in vitro, ex vivo or in vivo.

[13] A method for inducing an APC having an ability to induce a CTL, said method comprising a step selected from the group consisting of:
(a) contacting an APC with the peptide of any one of [1] to [5] in vitro, ex vivo or in vivo; and
(b) introducing a polynucleotide encoding the peptide of any one of [1] to [5] into an APC.

[14] A method for inducing a Th1 cell, said method comprising a step selected from the group consisting of:
(a) co-culturing a CD4-positive T cell with an APC that presents on its surface a complex of an MHC class II molecule and the peptide of any one of [1] to [5] or fragment thereof; and
(b) introducing a polynucleotide encoding both of T cell receptor (TCR) subunits, or polynucleotides encoding each of TCR subunits into a CD4-positive T cell, wherein the TCR can bind to a complex of an MHC class II molecule and the peptide of any one of [1] to [5] or fragment thereof presented on cell surface, or a method for inducing a Th1 cell, said method comprising a step selected from the group consisting of:
(a) co-culturing a CD4-positive T cell with an APC that presents on its surface a complex of an MHC class II molecule and the peptide of any one of [1] to [5] or fragment thereof; and
(b) introducing a single polynucleotide encoding both of T cell receptor (TCR) subunits, or multiple polynucleotides each encoding a separate TCR subunit into a CD4-positive T cell, wherein the TCR can bind to a complex of an MHC class II molecule and the peptide of any one of [1] to [5] or fragment thereof presented on a cell surface of an APC.

[15] A method for inducing a CTL, said method comprising the step selected from the group consisting of:
(a) co-culturing both of a CD4-positive T cell and a CD8-positive T cell with APCs contacted with the peptide of [4] or [5]; and
(b) co-culturing a CD8-positive T cell with an APC contacted with the peptide of [4] or [5].
[16] A method for enhancing an immune response mediated by an MHC class II molecule, wherein the method comprises a step of administering to a subject at least one active ingredient selected from the group consisting of:
(a) one or more peptide(s) of any one of [1] to [5];
(b) one or more polynucleotide(s) of [6];
(c) one or more APC(s) presenting the peptide of any one of [1] to [5] or fragment thereof on their surface;
(d) one or more Th1 cell(s) that recognize(s) an APC presenting the peptide of any one of [1] to [5] or fragment thereof on its surface; and
(e) combination of any two or more of (a) to (d) above.
[17] An isolated APC that presents on its surface a complex of an MHC class II molecule and the peptide of any one of [1] to [5] or fragment thereof.
[18] The APC induced by the method of [12] or [13].
[19] An isolated Th1 cell that recognizes the peptide of any one of [1] to [5] or fragment thereof presented on a surface of an APC.
[20] The Th1 cell induced by the method of [14].
[21] A method of inducing an immune response against cancer in a subject in need thereof, said method comprising the step of administering to the subject a composition comprising at least one active ingredient selected from the group consisting of:
(a) one or more peptide(s) of any one of [1] to [5];
(b) one or more polynucleotide(s) of [6];
(c) one or more APC(s) presenting the peptide of any one of [1] to [5] or fragment thereof on their surface;
(d) one or more Th1 cell(s) that recognize(s) an APC presenting the peptide of any one of [1] to [5] or fragment thereof on its surface; and
(e) combination of any two or more of (a) to (d) above.
[22] An antibody or immunologically active fragment thereof against the peptide of any one of [1] to [5].
[23] A vector comprising a nucleotide sequence encoding the peptide of any one of [1] to [5].
[24] A host cell transformed or transfected with the expression vector of [23].
[25] A diagnostic kit comprising the peptide of any one of [1] to [5], the polynucleotide of [6] or the antibody of [22].

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

FIG. 1B. FIG. 1B depicts the two overlapping 26-mer and 24-mer long peptides (CDCA1 (39-64) and CDCA1 (55-78)) that have overlapping high consensus percentile ranks for multiple HLA-class II allelic product (DRB1*04:05, DRB1*15:02, and DPB1*02:01) and that include 9-mer peptides recognized in the context of HLA-A24 or -A2 by CTLs were selected (A, black bar), and synthesized to identify promiscuous HLA class II-restricted Th cell epitopes containing CTL epitopes.

FIG. 2A presents the induction of CDCA1-specific CD4$^+$ T cells by stimulation with long peptides and identification of restriction HLA-class II molecules. CD4$^+$ T cell lines were generated from 3 healthy donors with various HLA-class II genotypes after at least 3 rounds of stimulation with CDCA1 (55-78) or CDCA1 (39-64), and the numbers of IFN-gamma-producing CD4$^+$ T cells were analyzed by ELISPOT assay. In Part A, responses against CDCA1 (55-78) are shown for 3 healthy donors. The CD4$^+$ T cells were stimulated with autologous PBMC alone (−), PBMC pulsed with CDCA1 (55-78) (10 micro-g/ml), or PBMC pulsed with CDCA1 (55-78) in the presence of 5 micro-g/ml of mAb specific to HLA-DR, HLA-DP or HLA-DQ.

FIGS. 2B-2C. In FIG. 2B, responses against CDCA1 (55-78) are shown for 2 healthy donors. The CD4$^+$ T cells were stimulated with autologous PBMC alone (−), PBMC pulsed with CDCA1 (55-78) (10 micro-g/ml), or PBMC pulsed with CDCA1 (55-78) in presence of 5 micro-g/ml of mAb specific to HLA-DR or HLA-DP. In FIG. 2C, responses against CDCA1 (39-64) are shown for 2 healthy donors. HLA types of the donors were indicated at the top of each panel. Data are presented as the mean+/−SD of duplicate or triplicate assays. Representative data from at least three independent experiments with similar results are shown.

FIG. 3A presents the recognition of the CDCA1 (55-78) and CDCA1 (39-64) peptides by Th cells restricted by various HLA class II molecules. In FIG. 3A a CDCA1 (55-78)-specific CD4$^+$ T cell line established from a healthy donor-HD1 was co-cultured with L-DR4 pulsed or unpulsed with CDCA1 (55-78) in the presence of anti-HLA-DR or anti-HLA class I-blocking mAb, L-DR4 pulsed with WT1-peptide, or L-DR53 pulsed or unpulsed with CDCA1 (55-78). The numbers of IFN-gamma-producing Th cells were analyzed by an ELISPOT assay (upper panel). CDCA1 (55-78)-specific CD4+ T cell line from a healthy donor HD-2 was co-cultured with L-DR15 pulsed or unpulsed with CDCA1 (55-78) in the presence of anti-HLA-DR or anti-HLA class I-blocking mAb, or L-DR8 pulsed or unpulsed with CDCA1 (55-78) (lower panel).

In FIG. 3B, an HLA-DP-restricted and CDCA1 (55-78)-specific CD4+ T clone derived from a donor-HD3 was co-cultured with allogeneic PBMCs pulsed or unpulsed with CDCA1 (55-78) in the presence of anti-HLA-DR or anti-HLA-DP-blocking mAb from HLA-DP2-positive or negative five donors.

FIG. 3C depicts the recognition of a CDCA1 (55-78) peptide by HLA-DR4-restricted Th cells. CDCA1 (55-78)-specific CD4+ T cells derived from healthy donor-HD4 and healthy donor-HD5 were co-cultured with L-DR4 pulsed or unpulsed with CDCA1 (55-78) in the presence of anti-HLA-DR or anti-HLA class I-blocking mAb, L-DR4 pulsed with WT1-peptide, L-DR1 pulsed with CDCA1 (55-78) or L-DR53 pulsed with CDCA1 (55-78). The numbers of IFN-gamma-producing Th cells were analyzed by an ELISPOT assay. HLA types of the donors were displayed over the panels. Data are presented as the mean+/−SD of duplicate or triplicate assays. Representative data from at least three independent experiments with similar results are shown.

In FIG. 3D, a CDCA1 (39-64)-specific CD4+ T cell clone derived from a donor-HD1 was co-cultured with allogeneic PBMCs pulsed or unpulsed with CDCA1 (39-64) in the presence of anti-HLA-DR or anti-HLA-DP-blocking mAb from HLA-DP9-positive or negative two donors (upper panel). A CDCA1 (39-64)-specific CD4+ T line derived from a donor-HD3 were co-cultured with L-DR15 pulsed or unpulsed with CDCA1 (39-64) in the presence of anti-HLA-DR or anti-HLA class I-blocking mAb, or L-DR8 pulsed or unpulsed with CDCA1 (39-64) (lower panel). HLA types of the donors were indicated at the top of each panel. Data are presented as the mean+/−SD of duplicate or triplicate assays. Representative data from at least three independent experiments with similar results are shown.

FIG. 4A presents the functional characterization of bulk CDCA1 (55-78)-specific CD4+ Th cell line. In Part A-D, after 20 h incubation period of T cell co-cultured with L-DR4 (Part A and D) or autologous PBMCs (Part B and C) pulsed with the CDCA1 (55-78) or irrelevant peptide (WT1-0405 or HIV-LP), the culture medium was collected and the concentration of cytokines (IFN-gamma, GM-CSF, TNF-alpha, MIP1-beta, IL-4, IL-7) were measured using Bio-Plex assay system. Data are presented as the mean+/−SD of triplicate assays. Part E-H depicts the detection of CD107a exposed on the cell surface of CD4+ T cells after antigenic stimulation. Events shown are gated for CD4+ T cells. Cells were restimulated with CDCA1 (55-78), or irrelevant peptide (e.g. WT1-0405). The numbers inside the plots indicate the percentage of the cell population with the quadrant characteristic (CD4+ CD107a+ T cells).

In FIG. 4B, after 20 h incubation period of T cell co-cultured with autologous PBMCs pulsed with the CDCA1 (55-78) or irrelevant peptide (WT1-0405 or HIV-LP), the culture medium was collected and the concentration of cytokines (IFN-gamma, GM-CSF, TNF-alpha, MIP1-beta, IL-4, IL-7) were measured using Bio-Plex assay system.

In FIG. 4C, after 20 h incubation period of T cell co-cultured with autologous PBMCs pulsed with the CDCA1 (55-78) or irrelevant peptide (WT1-0405 or HIV-LP), the culture medium was collected and the concentration of cytokines (IFN-gamma, GM-CSF, TNF-alpha, MIP1-beta, IL-4, IL-7) were measured using Bio-Plex assay system.

In FIG. 4D, after 20 h incubation period of T cell co-cultured with L-DR4 pulsed with the CDCA1 (55-78) or irrelevant peptide (WT1-0405 or HIV-LP), the culture medium was collected and the concentration of cytokines (IFN-gamma, GM-CSF, TNF-alpha, MIP1-beta, IL-4, IL-7) were measured using Bio-Plex assay system.

FIG. 4E depicts the detection of CD107a exposed on the cell surface of CD4+ T cells after antigenic stimulation.

FIG. 4F depicts the detection of CD107a exposed on the cell surface of CD4+ T cells after antigenic stimulation.

FIG. 4G depicts the detection of CD107a exposed on the cell surface of CD4+ T cells after antigenic stimulation.

FIG. 4H depicts the detection of CD107a exposed on the cell surface of CD4+ T cells after antigenic stimulation.

FIGS. 5A-5B. FIG. 5A presents CDCA1 (55-78) and CDCA1 (39-64)-specific Th clones established from donor-HD1 recognizing autologous DCs loaded with the CDCA1 protein. In FIG. 5A, the HLA-DR4-restricted CDCA1 (55-78)-specific Th clone or the HLA-DR9-restricted CDCA1 (39-64)-specific Th clone ($2 \times 10^4$/well) were co-cultured with autologous DCs ($5 \times 10^3$/well) loaded with the recombinant CDCA1 protein (50 micro-g/ml) in the presence of anti-HLA-DR or anti-HLA class I-blocking mAb, control protein, or unloaded DCs. The numbers of IFN-gamma-producing Th clone were analyzed by an ELISPOT assay. In FIG. 5B, an HLA-DP2-restricted CDCA1 (55-78)-specific Th cell clone established from the donor-HD3 recognizes autologous DCs loaded with the CDCA1 protein. An HLA-DP2-restricted CDCA1 (55-78)-specific Th cell clone was co-cultured with autologous DCs loaded with the CDCA1 protein, and the numbers of IFN-gamma-producing Th cell clone were analyzed by an ELISPOT assay. Data are presented as the mean+/−SD of duplicate assays. Representative data from at least three independent experiments with similar results are shown.

FIG. 6A presents CDCA1-LPs inducing an efficient cross-priming of CTLs in vitro and in vivo. In Part A, CD8+ T cell isolated from HLA-2-positive and HLA-DR4-positive donor-HD1 was stimulated with DC loaded with the CDCA1 (55-78) LP. After three times stimulations, the generated CTL lines were co-cultured with T2 cells pulsed with CDCA1-A2 (65-73) SP in the presence of anti-HLA class I or anti-HLA-DR-blocking mAb or irrelevant peptide (HIV-A2), and the numbers of IFN-gamma-producing CTL were analyzed by an ELISPOT assay. Representative data from three independent experiments with similar results obtained by using two HLA-2-positive and HLA-DR4-positive healthy donors' PBMCs are shown. In FIG. 6B, expansion of CDCA1 (65-73) SP-specific CTLs in mice immunized with CDCA1 (55-78) LP emulsified in IFA. HLA-A2 Tgm were immunized at the base of the tail with CDCA1 (55-78) LP emulsified in IFA. Seven days after the second or third vaccinations with CDCA1 (55-78) LP, CD8+ T cells in inguinal lymph nodes were positively isolated and co-cultured with BM-DC pulsed with CDCA1-A2 (65-73) SP or irrelevant peptide, and the number of IFN-gamma-producing CD8+ T cells was analyzed by an ex vivo ELISPOT assay. Representative data from 7 independent experiments with similar results are shown.

FIGS. 6C-6D. In FIG. 6C, CDCA1 (55-78) LP induce efficient cross-priming of CDCA1-specific CTLs in HLA-A24+/A2+/DR4+ HD5. Purified CD8+ T-cells isolated from HD5 were stimulated with autologous DCs loaded with CDCA1 (55-78) LP. After three rounds of stimulation, the generated CTLs were restimulated with T2-cells pulsed with CDCA1-A2 (65-73) SP, C1R-A2402-cells pulsed with CDCA1-A24 (56-64) SP, or control SP-pulsed target cells. The numbers of IFN-gamma-producing CTLs were analyzed by ELISPOT assay. A representative data from 3 independent experiments with similar results is shown.

In FIG. 6D, HLA-A24 Tgm were immunized with CDCA1 (55-78) LP (left panel) or CDCA1 (39-64) LP (right panel). After the second vaccination with CDCA1-LPs, murine CD8+ T-cells in the inguinal lymph nodes were stimulated with BM-DC or C1R-A2402 pulsed with CDCA1-A24 (56-64) SP or HIV-A24 SP.

In FIG. 6E, Superior induction of CDCA1-specific CTLs by CDCA1-LPs vaccines. HLA-A24 Tgm were immunized with CDCA1 (55-78) LP, CDCA1 (39-64) LP, or CDCA1-A24 (56-64)(300 nmol/mouse). After the second vaccination with CDCA1-derived peptides, murine CD8+ T-cells in inguinal lymph nodes were stimulated with BM-DCs pulsed with CDCA1-A24 (56-64) SP or HIV-A24 SP (background). The results represent specific IFN-gamma spots after background subtraction. Data are presented as the mean+/−SD of triplicate assays. A representative of 3 independent experiments with similar results is shown.

In FIG. 7A, the PBMCs from an HLA-A2 and DR4 positive-healthy donor-HD1 from which an HLA-DR4-restricted CDCA1 (55-78)-specific CD4+ Th cell clone was generated, were cultured for 11 days with a mixture of CDCA1-A2 (65-73) and CDCA1-A2 (351-359) (Mixed SP, 20 micro g/ml respectively), Mixed SP+CDCA1 (55-78) (LP, 20 micro-g/ml), Mixed SP+CDCA1 (55-78)-specific CD4+ T cell clone (Th clone, 5×10$^5$/well), or Mixed SP+LP+ Th clone. After the culture for 7 days, these peptides (the same concentration as indicated above) and IL-2 (20 U/ml) were added (second stimulation), then IL-15 (5 ng/ml) was added on day 9. On day 11 of the culture, the cells were stained with PE-labeled tetramers of the HLA-A*02:01/CDCA1-A2 (65-73) peptide complex or HLA-A*02:01/CDCA1-A2 (351-359) peptide complex in combination with a FITC-labeled anti-human CD8 mAb, and analyzed by flow-cytometry. Dots in the upper right quadrant represent CD8+ tetramer+ T cells. Events shown are gated for CD8+ T cells. The numbers inside the plots indicate the percentage of the cell population with the upper right quadrant characteristic (CD8+ tetramer+ T cells). Data are representative of three independent experiments with similar results.

In FIG. 7B, the values of increase (fold increase) in CD8+ tetramer+ cells were shown.

In FIG. 7C, on day 14 of the culture, these peptides (the same concentration as indicated above) and IL-2 (20 U/ml) were added (third stimulation), then IL-15 (5 ng/ml) was added on day 16. On day 18 of the culture, the cells were stained with the PE-labeled tetramers in combination with a FITC-labeled anti-human CD8 mAb (upper panel). IFN-gamma-ELISPOT assay of CDCA1-A2-reactive T cells on day 18. Bars indicate the number of IFN-gamma spots when the generated lines were re-stimulated with T2 cells loaded with CDCA1-A2 (65-73), CDCA1-A2 (351-359) or irrelevant HIV-A2 peptides (closed bars). Data are presented as the mean+/−SD of triplicate assays. Statistically significant differences (p<0.05) are indicated with asterisks (lower panel).

In FIG. 7D, detection of CD107a exposed on the cell surface of CD8+ T cells after antigenic stimulation. Events shown are gated for CD8+ T cells. Cells were restimulated with CDCA1-A2 (65-73), CDCA1-A2 (351-359) or irrelevant HIV-A2 peptide. The numbers inside the plots indicate the percentage of the cell population with the quadrant characteristic (CD8+ CD107a+ T cells).

In FIG. 7E, Enhanced induction of CDCA1-A24 (56-64) SP-specific CTL by activated CDCA1 (55-78) LP-specific CD4+ T-cells. CDCA1 (55-78) LP-specific bulk CD4+ T-cells and CDCA1-A24 (56-64) SP-specific bulk CD8+ T cells derived from HLA-A24+/DR15+ HD2 were cultured with autologous DCs in the presence of CDCA1-A24 (56-64) SP (SP alone), CDCA1-A24 (56-64) SP+control LP (Control+LP) or CDCA1-A24 (56-64) SP+CDCA1 (55-78) LP (CDCA1 (55-78) LP+SP) without addition of any cytokine. After 1-week in vitro culture with peptides, the cultured cells were stained with PE-labeled tetramer of the HLA-A*24:02/CDCA1-A24 (56-64) complex and FITC-labeled anti-human CD8 mAb. The results of cells cultured without any peptide were also shown (No peptide). The column of pre-stimulation indicate the absolute number of tetramer+CD8+ T-cells/well of CDCA1-A24 (56-64) SP-specific bulk CD8+ T cells line used in this experiment. Representative CDCA1-A24 (56-64) SP-specific tetramer staining is shown (gated on CD8+ T cells, dot plots). Data are presented as the mean+/−SD of triplicate assays. Representative data from 3 independent experiments with similar results are shown.

FIG. 8A presents the induction of CDCA1-specific Th cells from healthy donors. In Part A, CDCA1-specific Th cells were generated from a DR4+ healthy donor (HD1) by stimulation with CDCA1 (55-78) LP. The generated Th cells were re-stimulated with autologous PBMCs or L-cells pulsed with CDCA1 (55-78) LP. A WT1-peptide was used as a control peptide. The number of IFN-gamma-producing Th cells was analyzed by ELISPOT assay. Representative data from at least three independent experiments with similar results obtained from HD1 are shown. The similar results were obtained from other two DR4+ donors (Table 1; HD4 and HD5). The HLA class-II genotype of donor HD1 is indicated above the panels. The underlined HLA-class II alleles encode HLA-class II-molecule presenting the peptides to Th cells. Blocking effect by HLA-DQ mAb was not tested in HD1.

In FIG. 8B, CDCA1-specific Th cells were generated from a DR4-negative, DR15-positive healthy donor (HD2) by stimulation with CDCA1 (55-78) LP. Representative data from at least 5 independent experiments with similar results are shown.

FIG. 8C1. In FIG. 8C1, the HLA-DP2-restricted and CDCA1 (55-78) LP-specific bulk Th cell line (C-1) or Th cell clones (C-2) were established from HD3. HLA-DP-restricted Th clones were co-cultured with allogeneic PBMCs derived from HLA-DP2-positive or negative donors pulsed/unpulsed with CDCA1 (55-78) LP.

FIG. 8C2. In FIG. 8C2, the HLA-DP2-restricted and CDCA1 (55-78) LP-specific bulk Th cell clones were established from HD3.

In FIG. 8D, CDCA1 (39-64) LP-specific Th cells were generated from a DR15+ healthy donor (HD3) by stimulation with CDCA1 (39-64) LP.

In FIG. 8E, the HLA-DR9-restricted CDCA1 (39-64) LP-specific bulk Th cells (left panel) or Th cell clone (right panel) were established from HD1. HLA-DR-restricted Th-clone was co-cultured with allogeneic PBMCs pulsed or unpulsed with CDCA1 (39-64) LP from HLA-DR9-positive or negative donors. This HLA-DR-restricted Th cell clone generated from HD1 did not show response to CDCA1 (39-64) LP-pulsed L-DR4 cells (data not shown). The number of IFN-gamma-producing Th cells was analyzed by ELISPOT assay. Data are presented as the mean+/−SD of triplicate assays. Representative data from at least 3 independent experiments with similar results are shown. HLA class-II genotypes of donors were indicated above the panels. The underlined HLA-class II alleles encode HLA-class II-molecule presenting the peptides to Th cells.

FIG. 9A presents CDCA1-LPs induce efficient expansion of CDCA1-A24 (56-64) SP-specific CD8+ T-cells in vitro. In Part A, CDCA1-A24 (56-64)-specific bulk CTLs established from HD2 (HLA-A24+ and DR15+) were stimulated with CDCA1 (55-78) LP (closed circle) or irrelevant LP (open circle)-pulsed autologous DCs in vitro. Before LP-stimulation (day 0) and on days 5, 7, 8, and 10 after stimulation, an aliquot of cultured cells ($1 \times 10^5$ cells) CD8+ T-cells was stained with a CDCA1-A24 (56-64)-specific tetramer in combination with an anti-human CD8 mAb. Representative data on day 0 and day 10 from 3 independent experiments are shown (right panel). Events are gated for CD8+ T-cells. The percentage of tetramer+ cells in CD8+ T-cells is depicted with lines (left panels).

In FIG. 9B, CDCA1 (55-78) LP induce efficient expansion of CDCA1-A24 (56-64) SP-specific CD8+ T-cells in vitro. CDCA1-A24 (56-64) SP-specific bulk CTLs established from HD5 (HLA-A24+ and DR4+) were stimulated with CDCA1 (55-78) LP (right bar) or control LP (middle bar)-pulsed autologous DCs in vitro. Before LP-stimulation (Pre-LP stimulation, day 0; left bar) and on day 7 after stimulation (middle and right bar), the number of IFN-gamma producing CD8+ T-cells ($1 \times 10^5$/well) upon stimulation with CDCA1-A24 (56-64) SP-pulsed or HIV-A24 SP (background)-pulsed C1R-A2402 cells ($2 \times 10^4$/well) was counted by ELISPOT assay. A representative data from 3 independent experiments is shown. Data are presented as the mean+/−SD of triplicate assays.

In FIG. 9C, PBMCs from the HNC patient (HNC29) vaccinated with CDCA1-A24 (56-64) SP were cultured with a mixture of CDCA1 (55-78) LP and CDCA1 (39-64) LP. On day 0 (ex vivo) and day 7 (after in vitro stimulation with CDCA1-LPs), the PBMCs were stained with a tetramer HLA-A*24:02/CDCA1-A24 (56-64) complex or control tetramer. (gated on CD8+ T-cells). On day 7, the frequency of CDCA1-A24 (56-64)-SP-specific CTLs was also detected by IFN-gamma ELISPOT assay (right panel, bar graph). Data are presented as the mean+/−SD of triplicate assays.

In FIGS. 9D-9G, PBMCs from the HNC patient (HNC26, 31, 39, and 109) vaccinated with CDCA1-A24 (56-64) SP were cultured with a mixture of CDCA1 (55-78) LP and CDCA1 (39-64) LP. On day 0 (ex vivo) and day 7 (after in vitro stimulation with CDCA1-LPs), the cells were stained with a tetramer HLA-A*24:02/CDCA1-A24 (56-64) complex or control tetramer (gated on CD8+ T-cells).

FIG. 9E. In FIG. 9E, PBMCs from the HNC patient (HNC31) vaccinated with CDCA1-A24 (56-64) SP were cultured with a mixture of CDCA1 (55-78) LP and CDCA1 (39-64) LP.

FIG. 9F. In FIG. 9F, PBMCs from the HNC patient (HNC39) vaccinated with CDCA1-A24 (56-64) SP were cultured with a mixture of CDCA1 (55-78) LP and CDCA1 (39-64) LP.

FIG. 9G. In FIG. 9G, PBMCs from the HNC patient (HNC109) vaccinated with CDCA1-A24 (56-64) SP were cultured with a mixture of CDCA1 (55-78) LP and CDCA1 (39-64) LP.

FIG. 10A presents cross-presentation of CDCA1-LP by DCs. In FIG. 10A, Uptake and cross-presentation of CDCA1 (55-78) LP by DCs. Unfixed or fixed DCs were pulsed for 3 h with CDCA1 (55-78) LP or CDCA1-A24 (56-64) SP. The bulk CDCA1-A24 (56-64)-specific CTLs were co-cultured for 6 h and responses were measured by IFN-gamma labeling. Events were gated for CD8+ tetramer+ T-cells and the numbers inside the plots indicate the percentage of IFN-gamma+ T-cells.

In FIG. 10B, Cross-presentation of CDCA1 (39-64) LP by DCs. Unfixed or fixed DCs were pulsed for 3 h with CDCA1 (39-64) LP or CDCA1-A24 (56-64) SP. The bulk CDCA1-A24 (56-64) SP-specific CTLs were co-cultured for 6 h and responses were measured by IFN-gamma labeling. Events were gated for CD8+ tetramer+ T-cells and the numbers inside the plots indicate the percentage of IFN-g+ T-cells.

FIGS. 11A-11B. FIGS. 11A-11B presents the presence of CDCA1-LPs-specific Th cells in PBMCs isolated from HNC patients vaccinated with CDCA1-A24 (56-64) SP. In FIG. 11A, After 1-week in vitro stimulation of PBMCs with a mixture of CDCA1 (39-64) LP and CDCA1 (55-78) LP, the frequency of individual CDCA1-LPs-specific T-cells was detected by IFN-gamma ELISPOT assay. In FIG. 11B, HNC patients demonstrate elevated CDCA1-specific CD4+ T-cell immunity compared to normal healthy individuals. Column graph showing proportion of healthy donors (control) and HNC patients responding to CDCA1-LPs. p values represent statistical results from Fisher's exact test.

In FIG. 11C, CDCA1-specific-Th cell responses were assessed in 16 HNC patients vaccinated with CDCA1-A24 (56-64) SP (After Vac.), 7 non-vaccinated patients (Before Vac.), and 10 healthy donors. The results represent specific IFN-gamma spots after background subtraction. Each dot represents an individual donor. Horizontal lines denote median values, and p values represent statistical results from a nonparametric Mann-Whitney U test. The experiments in 7 of 19 HNC patients (HNC10, 26, 34, 37, 38, 40, and 103) were performed in single well.

In FIG. 11D, HLA class II-restriction of the IFN-gamma-producing T-cells. PBMCs stimulated with LPs for 1 week were re-stimulated with each CDCA1-LP in the presence of mAb specific to HLA-DR, -DP, -DQ, or HLA-class I. Six of 20 bar graph obtained from 12 HNC patients with similar results (HNC26, 29, 31, 34, 35, 39, 40, 42, 103, 105, 107, and 108) are shown. The experiments in 6 of 12 HNC patients (HNC26, 34, 40, 103, and 107) were performed in single well. $CDCA1_{39-64}$-LP; representative 3 bar graphs from 10 HNC patients (HNC26, 29, 31, 34, 39, 40, 42, 103, 107, and 108). CDCA1 (55-78) LP; representative 3 bar graphs from 10 HNC patients (HNC26, 29, 31, 34, 35, 39, 40, 103, 105, and 108).

In FIG. 11E, The repeated CTL-epitope vaccinations induce (HNC39, 40, 42, and 109) or enhance (HNC107 and 108) CDCA1-specific Th cell responses (CDCA1 (39-64) LP, white bars; CDCA1 (55-78)-LP, black bars). The experiments in 3 of 6 HNC patients (HNC40, 108, and 109) were performed in single well.

FIG. 11F. In FIG. 11F, clinical characteristics of HNC patients are shown. CDCA1-specific T-cell responses measured by IFN-gamma ELISPOT assay as detailed in the Materials and Methods. The experiments in 7 of 19 HNC patients (HNC10, 26, 34, 37, 38, 40, and 103) were performed in single wells. Number of vaccinations "0" indicates a patient before vaccination. The (+) and (−) indicate positive and negative responses. The underlined HLA-class II alleles encode HLA-class II-molecule presenting CDCA1-LP to Th cells in healthy donors (FIGS. 8A-8F; HLA-DRB1*04:05, DRB1*09:01, DRB1*15:02, and DPB1*02:01). No., Number; CTR, Clinical Trials Registry; vac., vaccination; HNC, Head-and-neck cancer; M/F, male/female; LP, long peptide; n.t., not tested

DESCRIPTION OF EMBODIMENTS

Figure 1A:
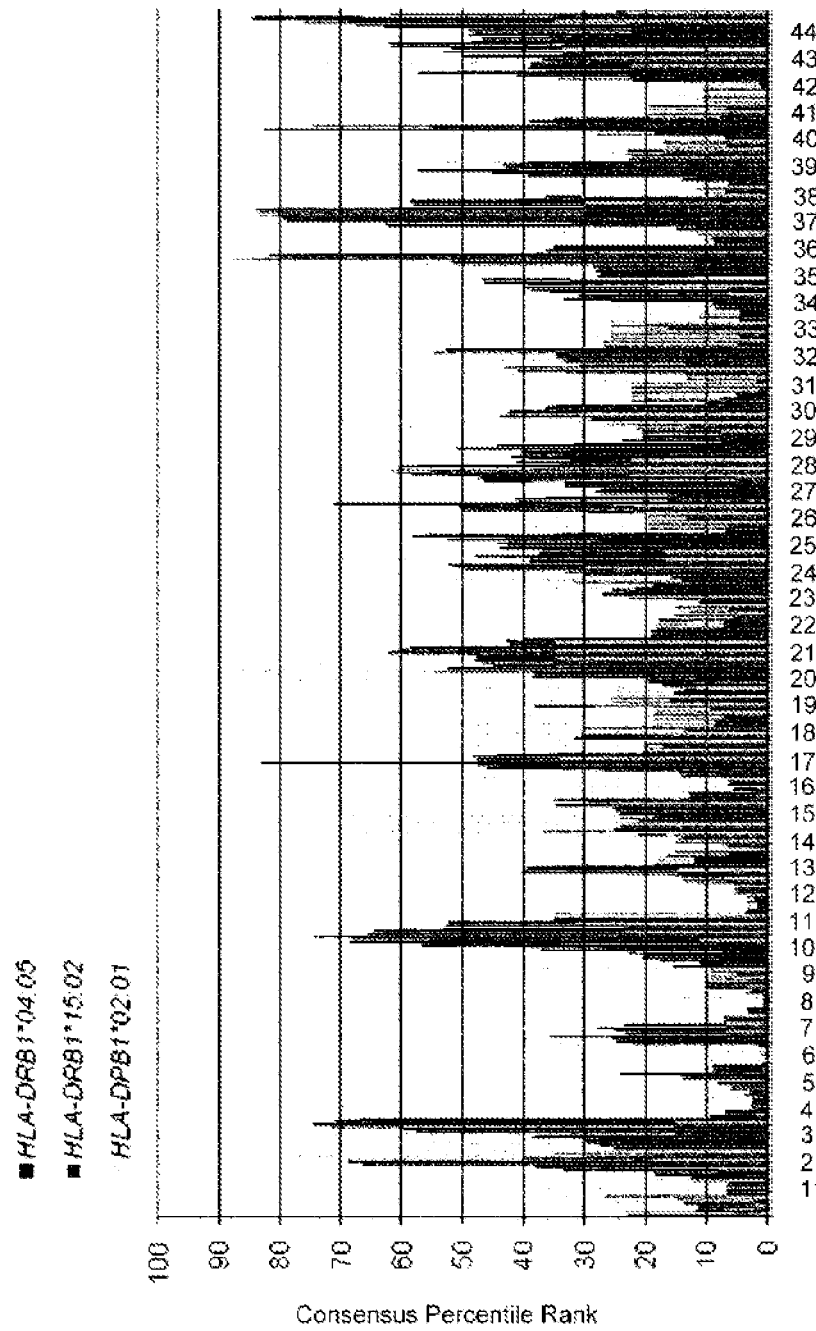
FIG. 1A presents promiscuous HLA class II-binding CDCA1 derived peptides including CTL epitopes predicted by the computer algorithm (consensus method). Part A depicts the results of the analysis of the amino acid sequence of the human CDCA1 protein using a computer algorithm (IEBD analysis resource, consensus method, tools.immuneepitope.org/analyze/html/mhc_II_binding.html). The numbers of horizontal axis indicate the amino acid residue positions of N-terminus of CDCA1-derived 15-mer peptides. Higher consensus percentile rank indicates stronger binding affinity to HLA class II molecules.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

I. Definitions

Unless otherwise defined, all technical and scientific terms used herein have the same meaning as commonly understood by one of ordinary skill in the art to which the present invention belongs. However, in case of conflict, the present specification, including definitions, will control.

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to peptide that are substantially free of cellular material such as carbohydrate, lipid, or other contaminating proteins from the cell or tissue source from which the peptide is derived, or substantially free of chemical precursors or other chemicals when chemically synthesized.

The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide" and "nucleic acid" are used interchangeably herein and, unless otherwise specifically indicated, are referred to by their commonly accepted single-letter codes.

The terms "agent" and "composition" are used interchangeably herein to refer to a product that includes specified ingredients in specified amounts, as well as any product that results, directly or indirectly, from combination of the specified ingredients in the specified amounts. Such term in relation to pharmaceutical composition, is intended to encompass a product including the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically or physiologically acceptable carrier.

The term "active ingredient" herein refers to a substance in a composition that is biologically or physiologically active. Particularly, in the context of a pharmaceutical composition, the term "active ingredient" refers to a component substance that shows an objective pharmacological effect. For example, in case of pharmaceutical compositions for use in the treatment or prevention of cancer, active ingredients in the compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effect of active ingredients is inductions of immune responses mediated by MHC Class II molecules. Before being formulated, the "active ingredient" may also be referred to as "bulk", "drug substance" or "technical product".

The phrase "pharmaceutically acceptable carrier" or "physiologically acceptable carrier", as used herein, means a pharmaceutically or physiologically acceptable material, composition, substance or vehicle, including, but are not limited to, a liquid or solid filler, diluent, excipient, solvent or encapsulating material.

Unless otherwise defined, the term "cancer" refers to cancers overexpressing CDCA1 gene, including, for example, breast cancer, bladder cancer, esophageal cancer, small cell lung cancer (SCLC), non-small cell lung cancer (NSCLC) and head-and-neck cancer (HNC).

Unless otherwise defined, the terms "T lymphocyte" and "T cell" are used interchangeably herein.

Unless otherwise defined, the term "cytotoxic T lymphocyte", "cytotoxic T cell" and "CTL" are used interchangeably herein and, otherwise specifically indicated, refer to a sub-group of T lymphocytes that are capable of recognizing non-self cells (e.g., tumor cells, virus-infected cells) and inducing the death of such cells. CTLs are differentiated from $CD8^+$ T lymphocytes and can recognize peptides presented by MHC class I molecules.

Unless otherwise defined, the terms "HLA-A24" refers to the HLA-A24 type containing the subtypes, examples of which include, but are not limited to, HLA-A*2401, HLA-A*2402, HLA-A*2403, HLA-A*2404, HLA-A*2407, HLA-A*2408, HLA-A*2420, HLA-A*2425 and HLA-A*2488.

Unless otherwise defined, "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the terms "T helper type 1 cell" and "Th1 cell" are used interchangeably herein and, otherwise specifically indicated, refer to a sub-group of $CD4^+$ T lymphocytes that are capable of recognizing peptides presented by an MHC class II molecules, and associated with cellular immunity. Unless otherwise defined, the terms "Th cell", "$CD4^+$ T cell" and "$CD4^+$ helper T cell" are also used interchangeably herein. Th1 cells secrete a variety of cytokines (such as IFN-gamma, IL-2, TNF-beta, GM-CSF, TNF-alpha, and so on) to help activation and/or stimulation of other immune cells relating to cellular immunity (e.g., CTL, macrophage).

Unless otherwise defined, the terms "HLA-DR4" refers to the subtypes, examples of which include, but are not limited to, HLA-DRB1*04:01, HLA-DRB1*04:02, HLA-DRB1*04:03, LA-DRB1*04:04, HLA-DRB1*04:05, HLA-DRB1*04:06, HLA-DRB1*04:07, HLA-DRB1*04:08, HLA-DRB1*04:09, HLA-DRB1*04:10 and HLA-DRB1*04:11.

Unless otherwise defined, the term "HLA-DR9" refers to the subtypes, examples of which include, but are not limited to, HLA-DRB1*09:01, HLA-DRB1*09:02, HLA-DRB1*09:03, LA-DRB1*09:04, HLA-DRB1*09:05, HLA-DRB1*09:06, HLA-DRB1*09:07, HLA-DRB1*09:08 and HLA-DRB1*09:09.

Unless otherwise defined, the term "HLA-DR15" refers to the subtypes, examples of which include, but are not limited to, HLA-DRB1*15:01, HLA-DRB1*15:02, HLA-DRB1*15:03, HLA-DRB1*15:04, HLA-DRB1*15:05, HLA-DRB1*15:06, HLA-DRB1*15:07, HLA-DRB1*15:08, HLA-DRB1*15:09, HLA-DRB1*15:10 and HLA-DRB1*15:11.

Unless otherwise defined, the term "HLA-DP2" refers to the subtypes, examples of which include, but are not limited to, HLA-DPB1*0201 and HLA-DPB1*02:02. Unless otherwise defined, the phrase "immune response mediated with an MHC class II molecule" refers to immune responses induced by presentation of peptide by MHC class II molecule. Herein, "immune response mediated with an MHC class II antigen" includes immune responses induced by $CD4^+$ T cells, in particular, Th1 cells. Examples of such immune responses include, but not limited to, production of cytokines (such as IFN-gamma, IL-2, TNF-beta, GM-CSF, TNF-alpha, and so on) and activation and/or stimulation of other immune cells (such as CTL, macrophage, and so on).

Unless otherwise defined, the phrase "Th1 cell specific to CDCA1" refers to a Th1 cell that is specifically activated with an antigen presenting cell presenting a peptide derived from CDCA1, but not with other antigen presenting cells.

Unless otherwise defined, the phrase "CDCA1-specific CTL" refers to a CTL that specifically shows cytotoxicity against a target cell expressing CDCA1.

Unless otherwise defined, when used in the context of peptides, the phrase "CTL inducibility" refers to an ability of a peptide to induce a CTL when presented on an antigen-presenting cell.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multi specific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which this invention belongs.

II. Peptides

Peptides of the present invention described in detail below may be referred to as "CDCA1 peptide(s)" or "CDCA1 polypeptide(s)".

To demonstrate that peptides derived from CDCA1 function as an antigen recognized by T helper type 1 (Th1) cells, peptides derived from CDCA1 (SEQ ID NO: 10) were analyzed to determine whether they were antigen epitopes promiscuously restricted by MHC class II molecules.

Candidates of promiscuous MHC class II binding peptides derived from CDCA1 were identified based on their binding affinities to HLA-DR4, HLA-DR15 and HLA-DP2. After in vitro stimulation of CD 4+ T-cells by dendritic cells (DCs) loaded with these peptides, Th1 cells were successfully established using each of the following peptides:

```
CDCA1/
IVYGIRLEHFYMIVIPVNSEVMYPHL (55-78; SEQ ID NO: 1),
and

CDCA1/
NPKPEVLHMIYIVIRALQIVYGIRLEHF (39-64; SEQ ID NO:
2).
```

These established Th1 cells noted above showed potent specific Th1 cell activity in response to stimulation of antigen presenting cells pulsed with respective peptides. Furthermore, the aforementioned peptides could stimulate Th1 cells restricted by several HLA-DR and HLA-DP molecules (e.g., HLA-DR4, HL-DR15, HLA-DR9 and HLA-DP2) which are frequently observed in the Japanese population. These results demonstrate that CDCA1 is an antigen recognized by Th1 cells and that the peptides are epitope peptides of CDCA1 promiscuously restricted by several HLA-class II molecules (such as HLA-DR4, HLA-DR9, HLA-DR15, and HLA-DP2); accordingly, such peptides may be effective as target antigens for cytotoxicity by CTLs.

The above-identified peptides additionally contained an amino acid sequence of a CTL epitope having an ability to induce a CTL specific to CDCA1 and, as demonstrated herein, such peptides can induce CTLs specific to CDCA1 as well as Th1 cells. Accordingly, those peptides may be suitable peptides for induction of immune responses against cancer expressing CDCA1. Since the CDCA1 gene is over-expressed in most cancer tissues, including, for example, breast cancer, bladder cancer, esophageal cancer, small cell lung cancer (SCLC), non-small cell lung cancer (NSCLC) and head-and-neck cancer (HNC), it represents a good target for immunotherapy.

Accordingly, the present invention provides peptides having ability induce Th1 cells specific to CDCA1.

The peptides of the present invention can bind at least one MHC class II molecule and be presented on antigen presenting cells. Alternatively, the fragment of the peptides of the present invention may bind at least one MHC class II molecule and be presented on antigen presenting cells. Those fragments of the peptides may be produced by processing within antigen presenting cells. In preferred embodiments, the peptides of the present invention or fragment thereof have abilities to bind two or more kinds of MHC class II molecules (e.g., HLA-DR9 and HLA-DR15, HLA-DR4 and HLA-DR15, HLA-DR4 and HLA-DP2, HLA-DR15 and HLA-DP2, or HLA-DR4, HLA-DR15 and HLA-DP2). In other words, the peptides of the present invention may have an ability to induce Th1 cells that are restricted by two or more kinds of MHC class II molecules. In another embodiment, the peptides of the present invention include an amino acid sequence of a peptide having CDCA1-specific CTL inducibility. The typical examples of such peptides having CDCA1-specific CTL inducibility include peptides having an amino acid sequence of SEQ ID NO: 3 or 5.

Since the binding groove in an MHC class II molecule is open at both ends, MHC class II binding peptides are allowed to have flexibility in their length. The core binding motif for MHC class II molecule is composed of 9 amino acid residues, and MHC class II binding peptides generally have other amino acid residues flanking with the core binding motif. The number of flanking amino acid residues is not restricted. Thus, all amino acid residues of SEQ ID NO: 1 or 2 are not indispensable for binding an MHC class II molecule.

Accordingly, the peptide of the present invention can be a peptide having ability to induce a Th1 cell, such peptide including an amino acid sequence selected from the group consisting of:
(a) an amino acid sequence having more than 9 contiguous amino acids from the amino acid sequence of SEQ ID NO: 1 or 2; and
(b) an amino acid sequence of (a) in which one, two or several amino acids are substituted, deleted, inserted, and/or added.

The length of an MHC class II binding peptides is generally 10-30 amino acids. In that the amino acid sequences of SEQ ID NO: 1 and 2 are composed of a part of the amino acid sequence of CDCA1 (SEQ ID NO: 10), the peptides of the present invention can be a following peptide of [1] to [5]:

[1] An isolated peptide having 10-30 amino acids in length and including a part of the amino acid sequence of SEQ ID NO: 10, wherein such peptide comprises an amino acid sequence selected from the group consisting of:
(a) a contiguous amino acid sequence having more than 9 amino acids in length selected from the amino acid sequence of SEQ ID NO: 1 or 2; and
(b) an amino acid sequence of (a) in which one, two or several amino acids are substituted, deleted, inserted, and/or added,
wherein such peptide has ability to induce Th1 cell(s);
[2] The isolated peptide of [1], wherein the peptide or fragment thereof has abilities to bind at least two kinds of MHC class II molecules;
[3] The isolated peptide of [2], wherein the MHC class II molecules are selected from the group consisting of HLA-DR4, DR9, DR15 and DP2;
[4] The isolated peptide of any one of [1] to [3], wherein said peptide comprises an amino acid sequence of a peptide having CDCA1-specific cytotoxic T lymphocyte (CTL) inducibility; and
[5] The isolated peptide of [4], wherein said peptide comprises the amino acid sequence selected from the group consisting of:
(a) an amino acid sequence selected from the group consisting of SEQ ID NOs: 1 and 2; and
(b) an amino acid sequence of (a) in which one, two or several amino acids are substituted, deleted, inserted, and/or added.

Th1 cells induced by the peptide of the present invention are specific to CDCA1.

Therefore, in some embodiments, the present invention provides peptides of less than 30 amino acid residues consisting of a partial amino acid sequence of the amino acid sequence of SEQ ID NO: 10, wherein the peptides comprise the amino acid sequence of SEQ ID NO: 1 or 2.

Generally, software programs presently available on the Internet, such as those described in Wang P et al. 2008. PLoS Comput. Biol. 4(4):e1000048. 11:568; and Wang P et al. 2010. BMC Bioinformatics. can be used to calculate the binding affinities between various peptides and HLA antigens in silico. Binding affinity with HLA antigens can be measured as described, for example, in Nielsen M and Lund O. 2009. BMC Bioinformatics. 10:296.; Nielsen M et al. 2007. BMC Bioinformatics. 8:238. Bui H H, et al. 2005. Immunogenetics. 57:304-314. Sturniolo T et al. 1999. Nat. Biotechnol. 17(6):555-561 and Nielsen M et al. 2008. PLoS Comput. Biol. 4(7)e1000107. Thus, the present invention encompasses peptides of CDCA1 which are determined to bind with HLA antigens identified using such known programs.

As described above, since MHC class II binding peptides have flexibility in their length, the amino acid sequence of SEQ ID NO: 1 or 2 can be optionally flanked with additional amino acid residues so long as the resulting peptide retains the requisite Th1 cell inducibility. Such peptides having Th1 cell inducibility are typically less than about 30 amino acids, often less than about 29 amino acids, and usually less than about 28 or 27 amino acids. The particular amino acid sequence(s) flanking the amino acid sequence selected from among SEQ ID NOs: 1 and 2 are not limited and can be composed of any kind of amino acids, so long as such flanking amino acid sequences do not impair the Th1 cell inducibility of the original peptide. In typical embodiments, such flanking amino acid sequence(s) may be selected from among the amino acid sequence of SEQ ID NO: 10 adjacent to the amino acid sequence of SEQ ID NO: 1 or 2; however, the present invention is not limited thereto. As such, the present invention also provides peptides having Th1 cell inducibility and an amino acid sequence selected from among SEQ ID NOs: 1 and 2.

On the other hand, since a core binding motif for an MHC class II molecule is composed of 9 amino acid residues, the full length of the amino acid sequence of SEQ ID NO: 1 or 2 is not indispensible for binding an MHC class II molecule and induction of Th1 cells. Thus, a peptide of the present invention can take the form of an amino acid having more than 9 contiguous amino acids of SEQ ID NO: 1 or 2, provided said peptide retains the requisite Th1 cell inducibility. Peptides having Th1 cell inducibility are typically, more than about 10 amino acids, often more than 11 or 12 amino acids, and usually more than 13 or 14 amino acids. Accordingly, the peptides of the present invention can be peptides having Th1 cell inducibility and an amino acid sequence having more than 9, 10, 11, 12, 13 or 14 contiguous amino acids from the amino acid sequence of SEQ ID NO: 1 or 2.

It is generally known that the modification of one, two, or more amino acids in a protein will not influence the function of the protein, and in some cases will even enhance the desired function of the original protein. In fact, modified peptides (i.e., peptides composed of an amino acid sequence in which one, two or several amino acid residues have been modified (i.e., substituted, added, deleted or inserted) as compared to an original reference sequence) have been known to retain the biological activity of the original peptide (Mark et al., Proc. Natl. Acad. Sci. USA 1984, 81: 5662-6; Zoller and Smith, Nucleic Acids Res. 1982, 10: 6487-500; Dalbadie-McFarland et al., Proc. Natl. Acad. Sci. USA 1982, 79: 6409-13). Thus, in one embodiment, the peptides of the present invention may have both Th1 cell inducibility and an amino acid sequence selected from among SEQ ID NO: 1 and 2, wherein one, two or even more amino acids are added, inserted, deleted and/or substituted. Alternatively, the peptides of the present invention may have both of Th1 cell inducibility and an amino acid sequence in which one, two or several amino acids are added, inserted, deleted and/or substituted in the amino acid sequence of SEQ ID NO: 1 or 2.

Those of skilled in the art recognize that individual additions or substitutions to an amino acid sequence which alter a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be the peptides of the present invention. However, the peptides of the present invention are not restricted thereto and can include non-conservative modifications, so long as the modified peptide retains the Th1 cell inducibility of the original peptide. Furthermore, modified peptides should not exclude Th1 cell inducible peptides of polymorphic variants, interspecies homologues, and alleles of CDCA1.

To retain the requisite Th1 cell inducibility, one can modify (insert, add, deletion and/or substitute) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably, 15% of less, even more preferably 10% or 8%, less or 1 to 5%.

Homology analysis of preferred peptides of the present invention, namely SEQ ID NOs: 1 and 2 (CDCA1 55-78, 39-64), confirm that these peptides do not have significant homology with peptides derived from any other known human gene products. Thus, the possibility of these peptides generating unknown or undesired immune responses when used for immunotherapy is significantly lowered. Accordingly, these peptides are expected to be highly useful for eliciting immunity in cancer patients against CDCA1.

When used in the context of immunotherapy, the peptides of the present invention or fragment thereof should be presented on the surface of an antigen presenting cell, preferably as a complex with an HLA class II antigen. Therefore, it is preferable to select peptides that not only induce Th1 cells but also possess high binding affinity to the HLA class II antigen. To that end, the peptides can be modified by substitution, insertion, deletion and/or addition of the amino acid residues to yield a modified peptide having improved binding affinity.

The present invention also contemplates the addition of one to two amino acids to the N and/or C-terminus of the described peptides. Such modified peptides having high HLA antigen-binding affinity and retained Th1 cell inducibility are also included in the present invention.

For example, the present invention provides an isolated peptide of less than 31, 30, 29, 28, 27, or 26 amino acids in length which binds an HLA class II antigen, has Th1 cell inducibility, and comprises the amino acid sequence in which one, two or several amino acid(s) are modified in the amino acid sequence selected from the group consisting of SEQ ID NOs: 1 and 2.

These peptides may also be processed in an APC to present a processed fragment thereon, when these peptides are contacted with, or introduced into APC. For example, the peptide of the present invention may be processed into a fragment composed of usually 11-26 (typically 15-25) amino acid residues to be presented on a surface of an APC.

However, when the peptide sequence is identical to a portion of the amino acid sequence of an endogenous or exogenous protein having a different function, negative side effects such as autoimmune disorders and/or allergic symptoms against specific substances may be induced. Therefore, it may be desirable to first perform homology searches using available databases to avoid situations in which the sequence of the peptide matches the amino acid sequence of another protein. When it becomes clear from the homology searches that no peptide identical to or having 1 or 2 amino acid differences as compared to the objective peptide exists in nature, the objective peptide can be modified in order to increase its binding affinity with HLA antigens, and/or increase its Th1 cell and/or CTL inducibility without any danger of such side effects.

Although peptides having high binding affinity to the HLA class II antigens as described above are expected to be highly effective, the candidate peptides, which are selected according to the presence of high binding affinity as an indicator, are further examined for the presence of Th1 cell inducibility. Herein, the phrase "Th1 cell inducibility" indicates an ability of a peptide to confer an ability to induce a Th1 cell on an APC when contacted with the APC. Further, "Th1 cell inducibility" includes the ability of the peptide to induce Th1 cell activation and/or Th1 cell proliferation, promote Th1 cell mediated-cytokines production including IFN-gamma production to help and/or stimulate other cells (e.g. CTL, macrophage).

Confirmation of Th1 cell inducibility is accomplished by inducing antigen-presenting cells carrying human MHC antigens (for example, B-lymphocytes, macrophages, and dendritic cells (DCs)), or more specifically DCs derived from human peripheral blood mononuclear leukocytes, and after stimulation with the peptides, mixing with CD4-positive T cells (CD4$^+$ T cells), and then measuring the IFN-gamma produced and released by CD4$^+$ T cells. Alternatively, Th1 cell inducibility of the peptide can be assessed based on CTL activation by Th1 cells. For example, CD4$^+$ T cells are co-cultured with DCs stimulated with a test peptide, and then mixing with CTLs and target cells for CTLs. The target cells can be radiolabeled with $^{51}$Cr and such, and cytotoxic activity of CTLs activated by the cytokines secreted from Th1 cells can be calculated from radioactivity released from the target cells. Alternatively, Th1 cells inducibility can be assessed by measuring IFN-gamma produced and released by Th1 cells in the presence of antigen-presenting cells (APCs) stimulated with a test peptide, and visualizing the inhibition zone on the media using anti-IFN-gamma monoclonal antibodies.

In addition to the above-described modifications, the peptides of the present invention can also be linked to other substances, so long as the resulting linked peptide retains the Th1 cell inducibility of the original peptide. Examples of suitable substances include, for example: peptides, lipids, sugar and sugar chains, acetyl groups, natural and synthetic polymers, etc. The peptides of the present invention can contain modifications such as glycosylation, side chain oxidation, or phosphorylation, etc., provided the modifications do not destroy the biological activity of the original peptide. These kinds of modifications can be performed to confer additional functions (e.g., targeting function, and delivery function) or to stabilize the peptide.

For example, to increase the in vivo stability of a peptide, it is known in the art to introduce D-amino acids, amino acid mimetics or unnatural amino acids; this concept can also be adapted to the peptides of the present invention. The stability of a peptide can be assayed in a number of ways. For instance, peptidases and various biological media, such as human plasma and serum, can be used to test stability (see, e.g., Verhoef et al., Eur. J. Drug Metab. Pharmacokin 1986, 11: 291-302).

The peptides of the present invention may be presented on the surface of an APC as complexes in combination with HLA class II antigens and then induce Th1 cells. Therefore, the peptides forming complexes with HLA class II antigens on the surface of an APC are also included in the present invention. The APCs presenting the peptides of the present invention can be inoculated as vaccines.

The type of HLA antigens contained in the above complexes must match that of the subject requiring treatment and/or prevention. For example, in the Japanese population, HLA-DR4, DR9, DR15, and DP2 are prevalent and therefore would be appropriate for treatment of a Japanese patient. Typically, in the clinic, the type of HLA antigen of the patient requiring treatment is investigated in advance, which enables the appropriate selection of peptides having binding ability to the particular HLA class II antigen. In preferred embodiments, the peptides of the present invention can induce Th1 cells in a promiscuous manner. Herein, when a peptide can induce Th1 cells restricted by at least two different kinds of MHC class II molecules, the Th1 cell inducibility of the peptide is "promiscuous". In other word, when a peptide is recognized by at least two different kinds of MHC class II molecules, such antigen recognition is deemed "promiscuous". When used in the context of peptides, the phrase "recognized by at least two different kinds of MHC class II molecules" indicates that the peptide or fragment thereof can bind at least two different kinds of MHC class II molecules. For example, CDCA1 peptide (55-78; SEQ ID NO: 1), and CDCA1 peptide (39-64; SEQ ID NO: 2) are recognized by HLA-DR4, DR15 and DP2, and HLA-DR9 and DR15, respectively. Therefore, these peptides are typical examples of "promiscuous" epitope.

When using HLA-DR4, HLA-DR15 or HLA-ADP2 positive APCs, the peptides having the amino acid sequence of SEQ ID NO: 1 are preferably used. On the other hand, when using HLA-DR9 or DR15 positive APCs, preferred peptides are peptides having the amino acid sequence of SEQ ID NO: 2.

Accordingly, in preferred embodiments, peptides having the amino acid sequence of SEQ ID NO: 1 may be used for the induction of Th1 cells in a subject that has been identified as having HLA-DR4, HLA-DR15 or HLA-DP2 prior to the induction. Likewise, peptides having the amino acid sequence of SEQ ID NO: 2 may be used for the induction of Th1 cells in a subject that has been identified as having HLA-DR9 or DR15 prior to the induction.

III. Preparation of CDCA1 Peptides

The peptides of the present invention can be prepared using well known techniques. For example, the peptides of the present invention can be prepared synthetically, using recombinant DNA technology or chemical synthesis. The peptide of the present invention can be synthesized individually or as longer polypeptides composed of two or more peptides. The peptides of the present invention can be then be isolated, i.e., purified, so as to be substantially free of other naturally occurring host cell proteins and fragments thereof, or any other chemical substances.

The peptides of the present invention may contain modifications, such as glycosylation, side chain oxidation, or phosphorylation; provided the modifications do not destroy the biological activity of the original reference peptides. Other illustrative modifications include incorporation of D-amino acids or other amino acid mimetics that can be used, for example, to increase the serum half life of the peptides.

Peptides of the present invention can be obtained through chemical synthesis based on the selected amino acid sequence. Examples of conventional peptide synthesis methods that can be adapted for the synthesis include:
(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the peptides of the present invention can be obtained adapting any known genetic engineering method for producing peptides (e.g., Morrison J, J. Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide of the present invention can also be produced in vitro adopting an in vitro translation system.

IV. Polynucleotides

The present invention also provides a polynucleotide which encodes any of the aforementioned peptides of the present invention. These include polynucleotides derived from the natural occurring CDCA1 gene (GenBank Accession No. NM_145697 (SEQ ID NO: 9)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. As is well known in the art, a DNA is suitably composed of bases such as A, T, C, and G, and T is replaced by U in an RNA. One of skill will recognize that non-naturally occurring bases may be included in polynucleotides, as well.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J. 1984, 3: 801-5.

V. Antigen-Presenting Cells (APCs)

The present invention also provides antigen-presenting cells (APCs) that present complexes formed between HLA class II antigens and the peptides of the present invention or fragment thereof on its surface. The APCs that are obtained by contacting the peptides of the present invention can be derived from patients who are subject to treatment and/or prevention, and can be administered as vaccines by themselves or in combination with other drugs including the peptides of the present invention, Th1 cells or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since a DC is a representative APC having the strongest Th1 cell-inducing activity among APCs, DCs find use as the APCs of the present invention.

Moreover, in preferred embodiments, the peptides of the present invention can also induce CTL response mediated with the MHC class I antigen, as well as Th1 (class-II). In general, it is well known that the length of epitope recognized by the MHC-class I antigen is shorter (e.g. 8-10 amino acid residues) than that of MHC-class II (15 or more). Therefore, a processed product of the peptide of the present invention leads to induce CTL. In fact, CTL induced from CDCA1 peptide (55-78; SEQ ID NO: 1) recognizes the fragment (YMMPVNSEV; SEQ ID NO: 3) which has already been identified as a CTL recognition epitope. Likewise, CDCA1 peptide (39-64; SEQ ID NO: 2) also comprises the CTL recognition epitope sequence VYGIRLEHF (SEQ ID NO: 5) in the amino acid sequence. Accordingly, peptides of the present invention induce not only Th1 but also CTL after processing of them in APCs. In other words, APCs contacted with the peptides of the present invention process them to present fragments thereof with MHC-class I antigens, as well as the whole of them presented with MHC-class-II antigens. Consequently, both of Th1 which recognizes the peptides of the present invention presented on APCs with the MHC class II antigen, and CTL induced via processed fragments of the peptide can be induced using the peptides present invention.

For example, an APC can be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention or fragments thereof are induced in the body of the subject. Herein, the phrase "inducing an APC" includes contacting (stimulating) an APC with the peptides of the present invention to present complexes formed between HLA class II antigens and the peptides of the present invention or fragments thereof on their surface. Alternatively, after introducing the peptides of the present invention to APCs to allow the APCs to present the peptides or fragments thereof, the APCs can be administered to the subject as a vaccine. For example, the ex vivo administration can include steps of:

a: collecting APCs from a first subject,
b: contacting the APCs of step a, with the peptide of the present invention and
c: administering the peptide-loaded APCs to a second subject.

The first subject and the second subject may be the same individual, or can be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells, wherein the method comprises the step for admixing or formulating the peptide of the present invention with a pharmaceutically acceptable carrier. Further, the present invention also provides the peptides of the present invention for inducing antigen-presenting cells. The APCs obtained by step (b) can be administered to the subject as a vaccine.

In one aspect of the present invention, the APCs of the present invention have a high level of Th1 cell inducibility. Herein, in the phrase "high level of Th1 cell inducibility", the high level is relative to the level of that by APCs contacting with no peptide or peptides which can not induce Th1 cells. Herein, when used in the context of APCs, the phrase "Th1 cell inducibility" indicates an ability of an APC to induce a Th1 cell when contacted with a CD4$^+$ T cell. Such APCs having a high level of Th1 cell inducibility can be prepared by a method which includes the step of transferring genes containing polynucleotides that encode the peptides of the present invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res. 1996, 56: 5672-7; J. Immunol. 1998, 161: 5607-13; J. Exp. Med. 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides. Alternatively, the APCs of the present invention can be prepared by a method which induces the step of contacting APCs with the peptide of the present invention.

In preferred embodiments, the APCs of the present invention can be APCs that present complexes of an MHC class II molecule selected from the group among HLA-DR4, HLA-DR15 and HLA-DP2 and the peptide of the present invention (including an amino acid sequence selected from SEQ ID NO: 1) on their surface. In another embodiment, the APCs of the present invention can be APCs that present complexes of an MHC class II molecule selected from the group among HLA-DR9 and HLA-DR15 and the peptide of the present invention (including an amino acid sequence selected from SEQ ID NO: 2) on their surface. Preferably, HLA-DR4, HLA-DR9, HLA-DR15 and HLA-DP2 may be HLA-DRB1*04:05, HLA-DRB1*09:01, HLA-DRB1*15:02 and HLA-DPB1*02:01, respectively.

VI. T Helper-Type 1 Cells (Th1 Cells)

A Th1 cell induced against any of the peptides of the present invention strengthens immune responses of any of effector cells including CTLs targeting cancer cells in vivo, and thus serve as vaccines, in a fashion similar to the peptides per se. Thus, the present invention also provides isolated Th1 cells that are specifically induced or activated by any of the peptides of the present invention.

Such Th1 cells can be obtained by (1) administering one or more peptides of the present invention to a subject, collecting Th1 cells from the subject, (2) contacting (stimulating) APCs and CD4$^+$ T cells, or peripheral blood mononuclear leukocytes in vitro with the peptides of the present invention, and then isolating Th1 cells, (3) contacting CD4$^+$ T cells or peripheral blood mononuclear leukocytes in vitro with the APCs of the present invention, or (4) introducing a polynucleotide encoding both of T cell receptor (TCR) subunits or polynucleotides encoding each of TCR subunits into a CD4$^+$ T cell, wherein the TCR can bind to a complex of a MHC class II molecule and the peptide of the present invention. Such APCs for the method of (3) can be prepared by the methods described above. Details of the method of (4) is described bellow in section "VII. T cell receptor (TCR)".

Th1 cells that have been induced by stimulation with APCs of the present invention can be derived from patients who are subject to treatment and/or prevention, and can be administered by themselves or in combination with other drugs including the peptides of the present invention for the purpose of regulating effects. The obtained Th1 cells can activate and/or stimulate immune cells responsible for cellular immunity (e.g., CTL, macrophage). Such immune cells that can be activated by the Th1 cells of the present invention include CTLs that show cytotoxicity against target cells such as cancer cells. For example, target cells for such CTLs may be cells that endogenously express CDCA1 (e.g., cancer cells), or cells that are transfected with the CDCA1 gene. In preferred embodiments, the peptides of the present invention can contain at least one amino acid sequence of a CTL epitope peptide and also induce CTLs against CDCA1 expressing cells such as cancer cells, in addition to Th1 cells. In this case, the peptide of the present invention can induce Th1 cells and CTLs simultaneously or sequentially in vivo, and the induced Th1 cells can effectively activate the induced CTLs. Accordingly, such peptides containing at least one amino acid sequence of a CTL epitope peptide are suitable peptides for cancer immunotherapy.

Furthermore, the Th1 cells of the present invention secrete various cytokines (e.g. IFN-gamma) which activate and/or stimulate any CTLs against other target cells in an antigen independent manner. Accordingly, the Th1 cells of the present invention can also contribute to enhance CTL activity targeting cells expressing a tumor associated antigen (TAA) other than CDCA1. Thus, the Th1 cells of the present invention are useful for immunotherapy for not only tumor expressing CDCA1, but also tumor expressing other TAAs, as well as the peptides and APCs of the present invention.

In some embodiments, the Th1 cells of the present invention are Th1 cells that recognize cells presenting complexes of an HLA-DR or HLA-DP antigen and the peptide of the present invention. In the context of Th1 cells, the phrase "recognize a cell" refers to binding of a complex of an MHC class II molecule and the peptide of the present invention on the cell surface via its TCR and being activated in an antigen specific manner. Herein, the phrase "activated in antigen specific manner" refers to being activated in response to a particular MHC class II molecule and peptide and cytokine production from the activated Th1 cells are induced. In preferred embodiments, HLA-DR may be selected from the group consisting of HLA-DR4, HLA-DR9 and HLA-DR15. Preferably, HLA-DR4, HLA-DR9 and HLA-DR15 may be HLA-DRB1*04:05, HLA-DRB1*09:01 and HLA-DRB1*15:02, respectively. On the other hand, HLA-DP2 is a preferable example of the HLA-DP antigens. More preferably, HLA-DP2 may be HLA-DPB1*02:01.

VII. Cytotoxic T Cells (Cytotoxic T Lymphocytes or CTLs)

A cytotoxic T cell induced against any of fragments of the peptides of the present invention strengthens the immune response targeting cancer cells in vivo and thus can be used as vaccines, in a fashion similar to the peptides per se. Thus, the present invention also provides isolated cytotoxic T cells that are specifically induced or activated by any of the present peptides.

Such cytotoxic T cells can be obtained by (1) administering one or more peptides of the present invention to a subject, collecting cytotoxic T cells from the subject or (2) contacting (stimulating) subject-derived APCs and CD8-positive cells, or peripheral blood mononuclear leukocytes in vitro with the peptides of the present invention and then isolating cytotoxic T cells.

Cytotoxic T cells that have been induced by stimulation with APCs that present the peptides of the present invention, can be derived from patients who are subject to treatment and/or prevention and can be administered by themselves or in combination with other drugs including the peptides of this invention for the purpose of regulating effects. The obtained cytotoxic T cells act specifically against target cells presenting the peptides of the present invention, for example, the same peptides used for induction. The target cells can be cells that endogenously express CDCA1, or cells that are transfected with the CDCA1 gene; and cells that present a peptide of the present invention on the cell surface due to stimulation by the peptide can also serve as targets of activated CTL attack.

In some embodiments, the CTLs of the present invention are CTLs that recognize cells presenting complexes of HLA-A2 or A24 antigen and the peptide of the present invention. In the context of the CTL, the phrase "recognize a cell" refers to binding a complex of HLA-A2 or A24 antigen and the peptide of the present invention on the cell surface via its TCR and showing specific cytotoxic activity against the cell. Herein, "specific cytotoxic activity" refers to showing cytotoxic activity against the cell presenting a complex of HLA-A2 or A24 antigen and the peptide of the present invention but not other cells. For example, SEQ ID NOs:1 and 2 comprise an amino acid sequence of HLA-A2 recognition epitopes. Thus, from a peptide comprising SEQ ID NOs:1 or 2, a fragment preferred for HLA-A2 would be generated.

VIII. T Cell Receptor (TCR)

The present invention also provides a composition containing one or more polynucleotides encoding one or more polypeptides that are capable of forming a subunit of a T cell receptor (TCR), and methods of using the same. Such TCR subunits have the ability to form TCRs that confer specificity to CD4$^+$ T cells against APCs presenting CDCA1 peptides. By using the known methods in the art, the nucleic acids of alpha- and beta-chains as the TCR subunits of Th1 cells induced by the peptides of the present invention can be identified (WO2007/032255 and Morgan et al., J. Immunol., 171, 3288 (2003)). The derivative TCRs can bind APCs displaying CDCA1 peptides with high avidity, and optionally mediate efficient cytokine productions.

The polynucleotide/polynucleotides encoding the TCR subunits (i.e., a single polynucleotide encoding both of the TCR subunits or multiple polynucleotides each encoding a separate TCR subunits) can be incorporated into suitable vectors e.g. retroviral vectors. These vectors are well known in the art. The polynucleotides or the vectors containing them usefully can be transferred into a CD4$^+$ T cell, for example, a CD4$^+$ T cell from a patient. Advantageously, the present invention provides an off-the-shelf composition allowing rapid modification of a patient's own T cells (or those of another mammal) to rapidly and easily produce modified T cells having excellent cancer cell killing properties.

The present invention further provides Th1 cells which are prepared by transduction with the polynucleotide encoding both of the TCR subunits or polynucleotides encoding each of TCR subunits, wherein the TCR subunit can bind to the CDCA1 peptide (e.g. SEQ ID NO: 1 in the context of HLA-DR4, HLA-DR15 or HLA-DP2, and or SEQ ID NO: 2 in the context of HLA-DR9 or HLA-DR15). The transduced Th1 cells are capable of homing to cancer cells in vivo, and can be expanded by well known culturing methods in vitro (e.g., Kawakami et al., J. Immunol., 142, 3452-3461 (1989)). The Th1 cells prepared as described above can be used to form an immunogenic composition useful in treating or the prevention of cancer in a patient in need of therapy or protection.

IX. Pharmaceutical Agents or Compositions

To the extent that the methods and compositions of the present invention find utility in the context of the "treatment" of cancer, a treatment is deemed "efficacious" if it leads to clinical benefit such as, reduction in expression of CDAC1 gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors, reducing angiogenesis.

In the context of the present invention, the treatment and/or prophylaxis of cancer and/or the prevention of postoperative recurrence thereof include any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

As described above, the Th1 cells induced by the peptides of the present invention can help immune cells responsible for cellular immunity. Such immune cells include CTLs against not only cancer cells expressing CDCA1, but also cancer cells expressing other TAAs, since cytokines secreted by Th1 cells can affect CTLs in antigen independent manner. Accordingly, the present invention provides a pharmaceutical agent or composition comprising at least one peptide of the present invention. In the pharmaceutical agent or composition, such peptide is present in a therapeutically or pharmaceutically effective amount.

A pharmaceutical agent or composition of the present invention is useful for helping, stimulating and/or enhancing any immune cells responsible for cellular immunity (e.g., CTLs, macrophage), since Th1 cells induced by the agent or composition of the present invention can secrete cytokines that affects any immune cells responsible for cellular immunity. Therefore, the agent or composition of the present invention is useful for any purposes of enhancing or promoting immune responses mediated with such immune cells including CTLs. For example, the present invention provides agent or compositions comprising at least one of the peptide of the present invention, for use in treatment and/or prevention of cancer since the agent or composition of the present invention can enhance or promote immune responses against cancer or tumor mediated with such immune cells. The amount of the peptide in such agent or composition may be an amount that is effective in significantly enhancing or stimulating immunological response in a subject carrying a cancer expressing CDCA1.

Furthermore, as shown in FIG. 6, CDCA1 derived peptides identified in the course of the present invention have been confirmed to enhance CTL induction compared with stimulation with a CTL epitope only. Therefore, the present invention also provides an agent or composition for enhancing or stimulating immunological responses mediated with an MHC class I antigen, such as HLA-A2 and HLA-A24. In another embodiment, the present invention further provides a use of the peptide of the present invention for manufacturing an agent or composition for enhancing or stimulating an immunological response mediated with an MHC class I antigen.

In preferred embodiments, CDCA1 derived peptides identified in the course of the present invention can induce Th1 cells, as well as CTLs against CDCA1-expressing cells. Accordingly, the present invention also provides agents or compositions comprising at least one of the peptide of the present invention, for use in the induction of CTLs against cancer or tumor expressing CDCA1.

Moreover, the agent or composition comprising at least one of the peptides of the present invention can be used in enhancing or promoting immune responses mediated by MHC class II molecules.

Since CDCA1 expression is specifically elevated in several cancer types, including breast cancer, bladder cancer, esophageal cancer, small cell lung cancer (SCLC) and non-small cell lung cancer (NSCLC) as compared with normal tissue (Cancer Res. 2006 Nov. 1; 66(21):10339-48, WO2005/028676, WO2005/089735, WO2006/085684, WO2007/013665, WO2007/013671), the peptides of the present invention or polynucleotides encoding the peptides can be used for the treatment and/or prophylaxis of cancer or tumor, and/or for the prevention of postoperative recurrence thereof. Thus, the present invention provides a pharmaceutical agent or a composition for treating and/or for the prophylaxis of cancer or tumor, and/or prevention of postoperative recurrence thereof, which comprises one or more of the peptides of the present invention, or polynucleotides encoding the peptides as an active ingredient. Alternatively, the present peptides can be expressed on the surface of any of the foregoing cells, such as APCs for the use as pharmaceutical agents or compositions. In addition, the aforementioned Th1 cells can also be used as active ingredients of the present pharmaceutical agents or compositions.

In another embodiment, the present invention also provides the use of an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention in manufacturing a pharmaceutical composition or agent for treating cancer or tumor.

Alternatively, the present invention further provides an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
for use in treating cancer or tumor.

Alternatively, the present invention further provides a method or process for manufacturing a pharmaceutical composition or agent for treating cancer or tumor, wherein the method or process includes the step of formulating a pharmaceutically or physiologically acceptable carrier with an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
as active ingredients.

In another embodiment, the present invention also provides a method or process for manufacturing a pharmaceutical composition or agent for treating cancer or tumor, wherein the method or process includes the step of admixing an active ingredient with a pharmaceutically or physiologically acceptable carrier, wherein the active ingredient is selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention.

Alternatively, the pharmaceutical composition or agent of the present invention may be used for either or both of the prophylaxis of cancer or tumor and prevention of postoperative recurrence thereof.

The present pharmaceutical agents or compositions find use as a vaccine. In the context of the present invention, the phrase "vaccine" (also referred to as an immunogenic composition) refers to a composition that has the function to induce anti-tumor immunity upon inoculation into animals.

The pharmaceutical agents or compositions of the present invention can be used to treat and/or prevent cancers or tumors, and/or prevent postoperative or metastatic recurrence thereof in subjects or patients. Examples of such subjects include humans as well as other mammals including, but not limited to, mouse, rat, guinea-pig, rabbit, cat, dog, sheep, goat, pig, cattle, horse, monkey, baboon, and chimpanzee, particularly a commercially important animal or a domesticated animal.

In the course of the present invention, the peptides having an amino acid sequence selected from among SEQ ID NOs: 1 and 2 have been found to be promiscuous Th1 cell epitopes restricted by several HLA-DR and/or HLA-DP molecules (i.e., HLA-DR4, HLA-DR9, HLA-DR15, HLA-DP2) and can be candidates that can induce potent and specific immune response against cancer due to immune responses mediated with MHC class II molecules. Therefore, the present pharmaceutical agents or compositions which include any of these peptides having the amino acid sequences of SEQ ID NOs: 1 or 2 are particularly suited for the administration to subjects that have at least one selected from among HLA-DR4, HLA-DR9, HLA-DR15 and HLA-DP2 as an MHC class II molecule. The same applies to pharmaceutical agents or compositions which contain polynucleotides encoding any of these peptides.

Alternatively, in preferred embodiments, a peptide identified in the course of the present invention can also induce CTLs specific to CDCA1, when the peptide is applied to a subject having HLA-A2 or HLA-A24. Accordingly, through the administration of the peptide of the present invention, it is further expected that CTL response against cancer expressing CDCA1 can be induced in addition to Th1 cell induction. Moreover, the peptide of the present invention can not only induce CTL response against CDCA1-expressing cells via processing thereof, but also enhance it by Th1 cell induction mediated thereby. Accordingly, in order to achieve inductions of both of Th1 cells and CDCA1-specific CTLs in the same subject, for example, the subject to be treated preferably has at least one selected from among HLA-DR4, HLA-DR15 and HLA-DP2 as a MHC class II molecule and HLA-A2 or HLA-A24 as an MHC class I molecule, when administering peptides having the amino acid sequence of SEQ ID NO: 1. Likewise, by administration of a peptide having the amino acid sequence of SEQ ID NO: 2 to a subject having HLA-DR9 and/or DR15 as a MHC class II molecule and HLA-A24 as an MHC class I molecule, inductions of both of Th1 cells and CDCA1-specific CTLs can be achieved in the subject.

In another embodiment, the present invention provides an immunological cancer therapy dependent on Th1 cell induction. The therapeutic strategy provided by the present invention is applicable to and effective for any cancers independent of CDCA1 expression, as long as immune cells activated by cytokines secreted from Th1 cells target objective cancer cells.

Cancers or tumors to be treated by the pharmaceutical agents or compositions of the present invention include, but are not limited and preferred examples of such cancers include any kinds of cancers or tumors expressing CDCA1, including for example, breast cancer, bladder cancer, esophageal cancer, small cell lung cancer (SCLC), non-small cell lung cancer (NSCLC) and head-and-neck cancer (HNC).

The present pharmaceutical agents or compositions can contain in addition to the aforementioned active ingredients, other peptides that have the ability to induce Th1 cells or CTLs, other polynucleotides encoding the other peptides, other cells that present the other peptides or fragment thereof, and the like. Examples of such "other" peptides having the ability to induce Th1 cells or CTLs include, but are not limited to, peptides derived from cancer specific antigens (e.g., identified TAAs), but are not limited thereto.

If necessary, the pharmaceutical agents or compositions of the present invention can optionally include other therapeutic substances as an additional active ingredient, so long as the substance does not inhibit the antitumoral effect of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

Those of skill in the art will recognize that, in addition to the ingredients particularly mentioned herein, the pharmaceutical agents or compositions of the present invention can include other agents conventional in the art having regard to the type of formulation in question (e.g., fillers, binders, diluents, excipients, etc.).

In one embodiment of the present invention, the present pharmaceutical agents or compositions can be included in articles of manufacture and kits containing materials useful for treating the pathological conditions of the disease to be treated, e.g., cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents or compositions can, if desired, be packaged in a pack or dispenser device that can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient:

The peptide of the present invention can be administered directly as a pharmaceutical agent or composition, or if necessary, that has been formulated by conventional formulation methods. In the latter case, in addition to the peptides of the present invention, carriers, excipients, and such that are ordinarily used for drugs can be included as appropriate without particular limitations. Examples of such carriers include, but are not limited to, sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of the present invention can be used for anticancer purposes.

The peptides of the present invention can be prepared in a combination, composed of two or more of peptides of the present invention to induce Th1 cells in vivo. The peptide combination can take the form of a cocktail or can be conjugated to each other using standard techniques. For example, the peptides can be chemically linked or expressed as a single fusion polypeptide sequence. The peptides in the combination can be the same or different.

By administering the peptides of the present invention, the peptides or fragments thereof are presented at a high density by the HLA class II antigens on APCs, then Th1 cells that specifically react toward the complex formed between the displayed peptide and the HLA class II antigen are induced. Alternatively, APCs (e.g., DCs) are removed from subjects and then stimulated by the peptides of the present invention to obtain APCs that present any of the peptides of this invention or fragments thereof on their surface. These APCs can be readministered to the subjects to induce Th1 cells in the subjects, and as a result, aggressiveness towards the tumor-associated endothelium can be increased.

The pharmaceutical agents or compositions for the treatment and/or prevention of cancer or tumor that include a peptide of the present invention as the active ingredient can also include an adjuvant known to effectively establish cellular immunity. Alternatively, the pharmaceutical agents or compositions can be administered with other active ingredients or can be administered by formulation into granules. An adjuvant refers to a compound that enhances the immune response against the protein when administered together (or successively) with the protein having immunological activity. Adjuvants contemplated herein include those described in the literature (Clin. Microbiol. Rev. 1994, 7: 277-89). Examples of suitable adjuvants include, but are not limited to, aluminum phosphate, aluminum hydroxide, alum, cholera toxin, salmonella toxin, Incomplete Freund's adjuvant (IFA), Complete Freund's adjuvant (CFA), ISCO-Matrix, GM-CSF, CpG, O/W emulsion, and the like.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Examples of preferred salts include salts with an alkali metal, salts with a metal, salts with an organic base, salts with an organic acid (e.g., acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (e.g., hydrochloric acid, phosphoric acid, hydrobromic acid, sulfuric acid and so on). As used herein, the phrase "pharmaceutically acceptable salt" refers to those salts that retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical agents or compositions of the present invention may further include a component which primes Th1 cells and optionally CTLs. Lipids have been identified as agents capable of priming Th1 cells and optionally CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of Th1 cell and optionally CTL responses, E. coli lipoproteins, such as tripalmitoyl-S-glycerylcysteinlyseryl-serine (P3CSS) can be used to prime Th1 cells and optionally CTLs when covalently attached to an appropriate peptide (see, e.g., Deres et al., Nature 1989, 342: 561-4).

Examples of suitable methods of administration include, but are not limited to, oral, intradermal, subcutaneous, intramuscular, intraosseous, peritoneal, and intravenous injection, or such, and systemic administration or local administration to the vicinity of the targeted sites (i.e., direct injection). The administration can be performed by single administration or boosted by multiple administrations. A pharmaceutically or therapeutically effective amount of the peptide can be administered to a subject in need of treatment of cancer expressing CDCA1. Alternatively, an amount of the peptide of the present invention sufficient to enhance or stimulate immunological response mediated with Th1 cells, and/or to induce CTLs against cancer or tumor expressing CDCA1 can be administered to a subject carrying a cancer expressing CDCA1.

The dose of the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once in a few days to few months. One skilled in the art can readily determine suitable and optimal dosages.

(2) Pharmaceutical Agents or Compositions Containing Polynucleotides as the Active Ingredient:

The pharmaceutical agents or compositions of the present invention can also contain polynucleotides encoding the peptides disclosed herein in an expressible form. Herein, the phrase "in an expressible form" means that the polynucleotide, when introduced into a cell, will be expressed in vivo as a polypeptide that induces anti-tumor immunity. In an illustrative embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, Salmonella typhi vectors, detoxified anthrax toxin vectors, and the like, will be apparent. See, e.g., Shata et al., Mol. Med. Today 2000, 6: 66-71; Shedlock et al., J. Leukoc. Biol. 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann. Rev. Pharmacol. Toxicol. 1993, 33: 573-96; Mulligan, Science 1993, 260: 926-32; Morgan & Anderson, Ann. Rev. Biochem. 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

Like administration of peptides, administration of polynucleotides may be performed by oral, intradermal, subcutaneous, intravenous, intramuscular, intraosseous, and/or peritoneal injection, or such, and via systemic administration or local administration to the vicinity of the targeted sites finds use. The administration can be performed by single administration or boosted by multiple administrations. A pharmaceutically or therapeutically effective amount of the polynucleotide can be administered to a subject in need of treatment of cancer expressing CDCA1. Alternatively, an amount of the polynucleotide of the present invention sufficient to enhance or stimulate immunological response mediated with Th1 cells, and/or to induce CTLs against cancer or tumor expressing CDCA1 can be administered to a subject carrying a cancer expressing CDCA1. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once every a few days to once every few months. One skilled in the art can readily determine suitable and optimal dosages.

X. Methods Using the Peptides, APCs or Th1 Cells

The peptides of the present invention and polynucleotides encoding such peptides can be used for inducing APCs and Th1 cells of the present invention. The APCs of the present invention can be also used for inducing Th1 cells of the present invention. The peptides, polynucleotides, and APCs can be used in combination with any other compounds so long as the compounds do not inhibit their Th1 cell inducibility. Thus, any of the aforementioned pharmaceutical agents or compositions of the present invention can be used for inducing Th1 cells, and in addition thereto, those including the peptides and polynucleotides can be also used for inducing APCs as discussed below.

(1) Method of Inducing Antigen-Presenting Cells (APCs):

The present invention provides methods of inducing APCs using the peptides of the present invention or polynucleotides encoding the peptides. The induction of APCs can be performed as described above in section "VI. Antigen-presenting cells". The present invention also provides a method for inducing APCs having Th1 cell inducibility, the induction of which has been also mentioned under the item of "VI. Antigen-presenting cells", supra.

Alternatively, the present invention provides a method for preparing an antigen-presenting cell (APC) which has ability to induce a Th1 cell, wherein the method can include one of the following steps:
(a) contacting an APC with a peptide of the present invention in vitro, ex vivo or in vivo; and
(b) introducing a polynucleotide encoding a peptide of the present invention into an APC.

Alternatively, the present invention provides methods for inducing an APC having Th1 cell inducibility, wherein the methods include the step selected from the group consisting of:

(a) contacting an APC with the peptide of the present invention, and
(b) introducing the polynucleotide encoding the peptide of the present invention into an APC.

The methods of the present invention can be carried out in vitro, ex vivo or in vivo. Preferably, the methods of the present invention can be carried out in vitro or ex vivo. In preferred embodiment, APCs used for induction of APCs having Th1 cell inducibility can be preferably APCs expressing at least one selected from among HLA-DR4, HLA-DR9, HLA-DR15 and HLA-DP2 as an MHC class II molecule. Such APCs can be prepared by the methods well-known in the arts from peripheral blood mononuclear cells (PBMCs) obtained from a subject having at least one selected from among HLA-DR4, HLA-DR9, HLA-DR15 and HLA-DP2 as an MHC class II molecule. The APCs induced by the method of the present invention can be APCs that present a complex of the peptide of the present invention or fragment thereof and HLA class II antigen (e.g., HLA-DR4, HLA-DR9, HLA-DR15, HLA-DP2) on their surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor.

In another embodiment, the present invention provide agents or compositions for use in inducing an APC having Th1 cell inducibility, and such agents or compositions include one or more peptides or polynucleotides of the present invention.

In another embodiment, the present invention provides the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having Th1 cell inducibility.

In preferred embodiments, the peptides of the present invention can induce not only Th1 response but also CTL response after processing them. Accordingly, in preferred embodiments, APCs prepared by the method of the present invention can be also useful for inducing CTLs against CDCA1 expressing cells, including cancer cells. For example, when induced by the peptides containing the amino acid sequence of SEQ ID NO: 3, APCs expressing HLA-A2 are suitable for inducing CDCA1-specific CTLs. Alternatively, when induced by the peptides containing the amino acid sequence of SEQ ID NO: 5, APCs expressing HLA-A24 are suitable for inducing CDCA1-specific CTLs.

(2) Method of Inducing Th1 Cells:

Furthermore, the present invention provides methods for inducing Th1 cells using the peptides of the present invention, polynucleotides encoding the peptides or APCs presenting the peptides of the present invention or fragments thereof. The present invention also provides methods for inducing Th1 cells using a polynucleotide encoding a polypeptide that is capable of forming a T cell receptor (TCR) subunit recognizing a complex of the peptides of the present invention and HLA class II antigens. Preferably, the methods for inducing Th1 cells comprise at least one step selected from the group consisting of:

a: contacting a CD4-positive T cell with an antigen-presenting cell that presents on its surface a complex of an HLA class II antigen and the peptide of the present invention or fragment thereof, and
b: introducing a polynucleotide encoding both of TCR subunits or polynucleotides encoding each of TCR subunits, wherein the TCR can recognize or bind to a complex of the peptide of the present invention or fragment thereof and an HLA class II antigen, into a CD4-positive T cell.

When the peptides of the present invention are administered to a subject, Th1 cells are induced in the body of the subject, and immune responses mediated by MHC class II molecules (e.g., immune responses targeting cancer cells) are enhanced. Alternatively, the peptides and polynucleotides encoding the peptides can be used for an ex vivo therapeutic method, in which subject-derived APCs and CD4-positive cells, or peripheral blood mononuclear leukocytes are contacted (stimulated) with the peptides of the present invention in vitro, and after inducing Th1 cells, the activated Th1 cells are returned to the subject. For example, the method can include the steps of:

a: collecting APCs from subject,
b: contacting the APCs of step a, with the peptide of the present invention,
c: mixing the APCs of step b with $CD4^+$ T cells, and co-culturing for inducing Th1 cells: and
d: collecting $CD4^+$ T cells from the co-culture of step c.

Furthermore, Th1 cells can be induced by introducing a polynucleotide encoding both of TCR subunits or polynucleotides encoding each of TCR subunits, wherein the TCR can bind to a complex of the peptide of the present invention or fragment thereof and an HLA class II antigen, into CD4-positive T cells. Such transduction can be performed as described above in section "VIII. T cell receptor (TCR)".

The methods of the present invention can be carried out in vitro, ex vivo or in vivo. Preferably, the methods of the present invention can be carried out in vitro or ex vivo. CD4 positive T cells used for induction of Th1 cells can be prepared by well-known methods in the art from PBMCs obtained from a subject. In preferred embodiments, the donor for CD4-positive T cells can be a subject having at least one selected from among HLA-DR4, HLA-DR9, HLA-DR15 and HLA-DP2 as an MHC class II molecule. The Th1 cells induced by the methods of the present invention can be Th1 cells that can recognize APCs presenting a complex of the peptide of the present invention or fragment thereof and HLA class II antigen on its surface. When Th1 cells induced by the method of the present invention are administered to a subject in order to induce immune responses against cancer in the subject (or immune responses mediated by MHC class I molecules), the subject is preferably the same one from whom CD4-positive T cells are derived. However, the subject may be a different one from the CD4-positive T cell donor so long as the subject has the same HLA type with the CD4-positive T cell donor.

In preferred embodiments, the peptides of the present invention can induce CTLs against CDCA1 expressing cells, as well as Th1 cells. Therefore, the present invention further provides a method for inducing a CTL, which comprises at least one step selected from the group consisting of:

a: co-culturing both of a CD4-positive T cell and a CD8-positive T cell with APCs contacted with the peptide of the present invention; and
b: co-culturing a CD8-positive T cell with an APC contacted with the peptide of the present invention.

In such methods of inducing CTLs, the peptides of the present invention are processed in APCs to produce CTL epitope peptides, and produced CTL epitope peptides are presented on APC's surface.

Alternatively, according to the present invention, use of the peptides of the present invention for manufacturing a pharmaceutical agent or composition inducing Th1 cells is provided. In addition, the present invention provides a method or process for manufacturing a pharmaceutical agent or composition inducing Th1 cells, wherein the method comprises the step for admixing or formulating the peptide of the present invention with a pharmaceutically acceptable carrier. Further, the present invention also provides the peptide of the present invention for inducing Th1 cells.

The $CD4^+$ T cells induced by the method of the present invention can be administered to a subject as a vaccine.

In the context of the present invention, cancer overexpressing CDCA1 can be treated with these active ingredients. Examples of such cancers include, but are not limited to, breast cancer, bladder cancer, esophageal cancer, small cell lung cancer (SCLC), non-small cell lung cancer (NSCLC) and head-and-neck cancer (HNC). Accordingly, prior to the administration of the vaccines or pharmaceutical compositions comprising the active ingredients, it is preferable to confirm whether the expression level of CDCA1 in the cancer cells or tissues to be treated is enhanced as compared with normal cells of the same organ. Thus, in one embodiment, the present invention provides a method for treating cancer (over)expressing CDCA1, which method may include the steps of:
i) determining the expression level of CDCA1 in cancer cells or tissue(s) obtained from a subject with the cancer to be treated;
ii) comparing the expression level of CDCA1 with normal control; and
iii) administrating at least one component selected from the group consisting of (a) to (d) described above to a subject with cancer overexpressing CDCA1 compared with normal control.

Alternatively, the present invention may provide a vaccine or pharmaceutical composition that includes at least one component selected from the group consisting of (a) to (d) described above, for use in administrating to a subject having cancer overexpressing CDCA1. In other words, the present invention further provides a method for identifying a subject to be treated with a CDCA1 polypeptide of the present invention, such method including the step of determining an expression level of CDCA1 in subject-derived cancer cells or tissue(s), wherein an increase of the level compared to a normal control level of the gene indicates that the subject has cancer which may be treated with the CDCA1 polypeptide of the present invention. Methods of treating cancer of the present invention are described in more detail below.

Further, in preferred embodiments, the HLA type of a subject may be identified before administering the peptides of the present invention. For example, peptides having the amino acid sequence of SEQ ID NO: 1 are preferably administered to a subject identified as having HLA-DR4, HLA-DR15, or HLA-DP2. Alternatively, peptides having the amino acid sequence of SEQ ID NO: 2 are preferably administered to a subject identified as having HLA-DR9 or HLA-DR15.

Any subject-derived cell or tissue can be used for the determination of CDCA1-expression so long as it includes the objective transcription or translation product of CDCA1. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Exemplary mammals include, but are not limited to, e.g., human, non-human primate, mouse, rat, dog, cat, horse, and cow.

According to the present invention, the expression level of CDCA1 in cancer cells or tissues obtained from a subject is determined. The expression level can be determined at the transcription (nucleic acid) product level, using methods known in the art. For example, the mRNA of CDCA1 may be quantified using probes by hybridization methods (e.g., Northern hybridization). The detection may be carried out on a chip or an array. The use of an array is preferable for detecting the expression level of CDCA1. Those skilled in the art can prepare such probes utilizing the sequence information of CDCA1. For example, the cDNA of CDCA1 may be used as the probes. If necessary, the probes may be labeled with a suitable label, such as dyes, fluorescent substances and isotopes, and the expression level of the gene may be detected as the intensity of the hybridized labels.

Furthermore, the transcription product of CDCA1 (e.g., SEQ ID NO: 9) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of CDCA1. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing agents, such as formamide.

Alternatively, the translation product may be detected for the diagnosis of the present invention. For example, the quantity of CDCA1 protein (SEQ ID NO: 10) may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, $F(ab')_2$, Fv, etc.) of the antibody may be used for the detection, so long as the fragment or modified antibody retains the binding ability to the CDCA1 protein. Methods to prepare these kinds of antibodies for the detection of proteins are well known in the art, and any method may be employed in the present invention to prepare such antibodies and equivalents thereof.

As another method to detect the expression level of CDCA1 gene based on its translation product, the intensity of staining may be measured via immunohistochemical analysis using an antibody against the CDCA1 protein. Namely, in this measurement, strong staining indicates increased presence/level of the protein and, at the same time, high expression level of CDCA1 gene.

The expression level of a target gene, e.g., the CDCA1 gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells, by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of CDCA1 gene in samples from subjects whose disease states are known. Furthermore, the control level can be derived from a database of expression patterns from previously tested cells. Moreover, according to an aspect of the present invention, the expression level of CDCA1 gene in a biological sample may be compared to multiple control levels determined from multiple reference samples. It is preferred to use a control level determined from a reference sample derived from a tissue type similar to that of the subject-derived biological sample. Moreover, it is preferred to use the standard value of the expression levels of CDCA1 gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of CDCA1 gene is increased as compared to the normal control level, or is similar/equivalent to the cancerous control level, the subject may be diagnosed with cancer to be treated.

More specifically, the present invention provides a method of (i) diagnosing whether a subject has the cancer to be treated, and/or (ii) selecting a subject for cancer treatment, which method includes the steps of:

a) determining the expression level of CDCA1 in cancer cells or tissue(s) obtained from a subject who is suspected to have the cancer to be treated;
b) comparing the expression level of CDCA1 with a normal control level;
c) diagnosing the subject as having the cancer to be treated, if the expression level of CDCA1 is increased as compared to the normal control level; and
d) selecting the subject for cancer treatment, if the subject is diagnosed as having the cancer to be treated, in step c).

Alternatively, such a method includes the steps of:
a) determining the expression level of CDCA1 in cancer cells or tissue(s) obtained from a subject who is suspected to have the cancer to be treated;
b) comparing the expression level of CDCA1 with a cancerous control level;
c) diagnosing the subject as having the cancer to be treated, if the expression level of CDCA1 is similar or equivalent to the cancerous control level; and
d) selecting the subject for cancer treatment, if the subject is diagnosed as having the cancer to be treated, in step c).

In some embodiments, such a method may further comprise the step of identifying, after or before the steps a)-d) defined above, a subject having an HLA selected from the group consisting of HLA-DR4, HLA-DR9, HLA-DR15 and HLA-DP2. Cancer therapy according to the present invention is preferable for a subject that suffers from cancer overexpressing CDCA1 and has any one of HLA-DR4, HLA-DR9, HLA-DR15 and HLA-DP2. Methods for HLA typing are well known in the art. For example, PCR-based methods for typing HLA alleles are well known. Antibodies specific for each HLA molecule are also appropriate tools for identifying HLA types of a subject.

The present invention also provides a kit for determining a subject suffering from cancer that can be treated with the CDCA1 polypeptide of the present invention, which may also be useful in assessing and/or monitoring the efficacy of a particular cancer therapy, more particularly a cancer immunotherapy. Illustrative examples of suitable cancers include, but are not limited to, breast cancer, bladder cancer, esophageal cancer, small cell lung cancer (SCLC), non-small cell lung cancer (NSCLC) and head-and-neck cancer (HNC). More particularly, the kit preferably includes at least one reagent for detecting the expression of the CDCA1 gene in a subject-derived cancer cell, such reagent being selected from the group of:
(a) a reagent for detecting an mRNA of the CDCA1 gene;
(b) a reagent for detecting the CDCA1 protein; and
(c) a reagent for detecting the biological activity of the CDCA1 protein.

Examples of reagents suitable for detecting an mRNA of the CDCA1 gene include nucleic acids that specifically bind to or identify the CDCA1 mRNA, such as oligonucleotides that have a complementary sequence to a portion of the CDCA1 mRNA. These kinds of oligonucleotides are exemplified by primers and probes that are specific to the CDCA1 mRNA. These kinds of oligonucleotides may be prepared based on methods well known in the art. If needed, the reagent for detecting the CDCA1 mRNA may be immobilized on a solid matrix. Moreover, more than one reagent for detecting the CDCA1 mRNA may be included in the kit.

On the other hand, examples of reagents suitable for detecting the CDCA1 protein include antibodies to the CDCA1 protein. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the CDCA1 protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the CDCA1 protein may be included in the kit.

The kit may contain more than one of the aforementioned reagents. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

As an embodiment of the present invention, when the reagent is a probe against the CDCA1 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of CDCA1 mRNA present in the sample. The detection sites may be configured in any suitably detectable shape and are typically in the shape of a bar or dot spanning the width of a test strip.

The kit of the present invention may further include a positive control sample or CDCA1 standard sample. The positive control sample of the present invention may be prepared by collecting CDCA1 positive samples and then assaying their CDCA1 levels. Alternatively, a purified CDCA1 protein or polynucleotide may be added to cells that do not express CDCA1 to form the positive sample or the CDCA1 standard sample. In the present invention, purified CDCA1 may be a recombinant protein. The CDCA1 level of the positive control sample is, for example, more than the cut off value.

XI. Antibodies

The present invention further provides antibodies that bind to the peptide of the present invention. Preferred antibodies specifically bind to the peptide of the present invention and will not bind (or will bind weakly) to other peptides. Alternatively, antibodies bind to the peptide of the invention as well as the homologs thereof. Antibodies against the peptide of the invention can find use in cancer diagnostic and prognostic assays, as well as imaging methodologies. Similarly, such antibodies can find use in the treatment, diagnosis, and/or prognosis of other cancers, to the extent CDCA1 is also expressed or over-expressed in a cancer patient. Moreover, intracellularly expressed antibodies (e.g., single chain antibodies) may therapeutically find use in treating cancers in which the expression of CDCA1 is involved, examples of which include, but are not limited to, breast cancer, bladder cancer, esophageal cancer, small cell lung cancer (SCLC), non-small cell lung cancer (NSCLC) and head-and-neck cancer (HNC).

The present invention also provides various immunological assay for the detection and/or quantification of CDCA1 protein (SEQ ID NO: 10) or fragments thereof including a polypeptide composed of amino acid sequences selected from among SEQ ID NOs: 1 and 2. Such assays may include one or more anti-CDCA1 antibodies capable of recognizing and binding a CDCA1 protein or fragments thereof, as appropriate. In the present invention, anti-CDCA1 antibodies binding to CDCA1 polypeptide preferably recognize a polypeptide composed of amino acid sequences selected from among SEQ ID NOs: 1 and 2, preferably to the exclusion of other peptides. The binding specificity of antibody can be confirmed with inhibition test. That is, when the binding between an antibody to be analyzed and full-length of CDCA1 polypeptide is inhibited under presence of any fragment polypeptides having an amino acid sequence selected from among SEQ ID NOs: 1 and 2, the antibody is deemed to "specifically bind" the fragment. In the context of the present invention, such immunological assays are performed within various immunological assay formats well known in the art, including but not limited to, various types of radio-immunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing CDCA1 are also provided by the invention, including, but not limited to, radioscintigraphic imaging methods using labeled antibodies of the present invention. Such assays can clinically find use in the detection, monitoring, and prognosis of CDCA1 expressing cancers, examples of which include, but are not limited to, breast cancer, bladder cancer, esophageal cancer, small cell lung cancer (SCLC), non-small cell lung cancer (NSCLC) and head-and-neck cancer (HNC).

The present invention also provides antibodies that bind to a peptide of the invention. An antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, complete and partial peptides of polypeptide of the present invention may serve as immunization antigens. Examples of suitable partial peptide include, for example, the amino (N)-terminal or carboxy (C)-terminal fragment of a peptide of the present invention.

Herein, an antibody is defined as a protein that reacts with either the full length or a fragment of a CDCA1 peptide. In a preferred embodiment, antibody of the present invention can recognize fragment peptides of CDCA1 having an amino acid sequence selected from among SEQ ID NOs: 1 and 2. Methods for synthesizing oligopeptide are well known in the arts. After the synthesis, peptides may be optionally purified prior to use as immunogen. In the present invention, the oligopeptide (e.g., 24- or 26 mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, though preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies for use in the context of the present invention, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, wherein a non-human animal is immunized with an antigen for preparing hybridoma, human lymphocytes such as those infected by EB virus may be immunized with a peptide, peptide expressing cells or their lysates in vitro. Then, the immunized lymphocytes may be fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas may then be subsequently transplanted into the abdominal cavity of a mouse and the ascites extracted. The obtained monoclonal antibodies can be purified by, for example, ammonium sulfate precipitation, a protein A or protein G column, DEAE ion exchange chromatography or an affinity column to which the peptide of the present invention is coupled. An antibody of the present invention can be used not only for purification and detection of a peptide of the present invention, but also as a candidate for agonists and antagonists of a peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides for recombinant antibodies prepared as described above.

An antibody of the present invention may be a fragment of an antibody or modified antibody, so long as it binds to one or more of the peptides of the invention. For instance, the antibody fragment may be Fab, F(ab')$_2$, Fv or single chain Fv (scFv), in which Fv fragments from H and L chains are ligated by an appropriate linker (Huston et al., Proc. Natl. Acad. Sci. USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J. Immunol. 152: 2968-76 (1994); Better and Horwitz, Methods Enzymol 178: 476-96 (1989); Pluckthun and Skerra, Methods Enzymol 178: 497-515 (1989); Lamoyi, Methods Enzymol. 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Examples of suitable chromatography techniques, with the exception of affinity chromatography, include, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XII. Vectors and Host Cells

The present invention also provides for vectors and host cells into which a nucleotide encoding the peptide of a present invention is introduced. A vector of the present invention finds utility as a carrier of nucleotides, especially a DNA, of the present invention in host cell, to express the peptide of the present invention, or to administer the nucleotide of the present invention for gene therapy.

When E. coli is selected as the host cell and the vector is amplified and produced in a large amount in E. coli (e.g., JM109, DH5 alpha, HB101 or XL1Blue), the vector should have an "ori" suitable for amplification in E. coli and a marker gene suited for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J. Bacteriol. 169: 4379 (1987)). Means for introducing of the vectors into the target host cells include, for example, the calcium chloride method, and the electroporation method.

In addition to *E. coli*, for example, expression vectors derived from mammals (for example, pcDNA3 (Invitrogen) and pEGF-BOS (Nucleic Acids Res. 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should carry a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res. 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Hereinafter, the present invention is described in more detail with reference to specific Examples. However, while the following materials, methods and examples may serve to assist one of ordinary skill in making and using certain embodiments of the present invention, there are only intended to illustrate aspects of the present invention and thus in no way to limit the scope of the present invention. As one of ordinary skill in the art will readily recognize, methods and materials similar or equivalent to those described herein can be used in the practice or testing of the present invention.

EXAMPLES

Materials and Methods
Cell Lines and Antibodies

The TAP-deficient and HLA-A2-positive cell line T2 were purchased from Riken Cell Bank. As antigen presenting cells (APCs), a mouse fibroblast cell line, L-cell, which have genetically been engineered to express either DR1 (DRB1*01:01); L-DR1, DR4 (DRB1*04:05); L-DR4, DR8 (DRB1*08:03); L-DR8, DR15 (DRB1*15:02); L-DR15 or DR53 (DRB4*01:03); L-DR53 were used. The C1R-A2402 cells, an HLA-A24 transfectant of human B lymphoblastoid cell line C1R expressing a trace amount of intrinsic HLA class I molecule were a gift from Dr. Masafumi Takiguchi (Kumamoto University, Kumamoto, Japan). T2 cells and C1R-A2402 cells were used as target cells. These cells were maintained in vitro in DMEM (L-cells) or RPMI 1640 (T2 and C1R-A24 cells) supplemented with 10 percent FCS in a 5 percent $CO_2$ atmosphere at 37 degrees C.

Patients

Blood samples were collected from 19 HNC patients enrolled in two peptide vaccine trials, and the immune responses of Th cells reactive to CDCA1-LPs were investigated. These phase I/II clinical trials of cancer immunotherapy using three HLA-A24-binding SPs, (clinical-grade 9-10 amino acids long peptides) derived from cancer testis antigens, CDCA1 (CDCA1-A24 (56-64), reported in this study, FIG. 1), IMP-3 (IMP-3-A24 (508-516)), and LY6K (LY6K-A24 (177-186)) (Suda T, et al. Cancer Sci. 2007; 10:1803-8.) were reviewed and approved by the Institutional Review Board of Kumamoto University, Kumamoto, Japan. Peptides (1 mg each antigen) are emulsified in 500 micro L Montanide ISA51 and injected subcutaneously (s.c.) on days 0, 7, 14, 28, 42, 56, 63, and 70, then monthly until tumor progression or toxicity are observed. All HNC patients were selected based on HLA-A24 possession after providing written informed consent. The patients suffered from inoperable advanced HNC with recurrent or metastatic tumors and were resistant to standard therapy; they were enrolled in the trial under University Hospital Medical Information Network Clinical Trials Registry (UMIN-CTR) number 000008379 (CTR-8379). HNC patients with radical resection were enrolled in the trial under UMIN-CTR number 000008380 (CTR-8380). In the latter trial, HNC patients were treated with postoperative peptide vaccine immunotherapy combined with S-1, ifosfamide, or doxorubicin. These clinical trials and analyses are ongoing.

Prediction by an [algorithm] of HLA Class II-Binding Peptides

To predict potential promiscuous HLA-DR or -DP binding human CDCA1-derived peptides, the amino acid sequence of the human CDCA1 protein was analyzed using a computer algorithm (IEBD analysis resource, consensus method, tools.immuneepitope.org/analyze/html/mhc_II_binding.html) (Wang P et al. BMC Bioinformatics; 11: 568., Wang P et al. PLoS Comput Biol 2008; 4: e1000048.). The program analyzed 15 amino acid-long sequences offset encompassing the entire protein. The 24 and 26 amino acids-long peptides that have overlapping high consensus percentile ranks for multiple HLA-class II molecules encoded for by DRB1*04:05, DRB1*15:02, or DPB1*02:01 alleles, and that naturally include CDCA1-derived 9-mer CTL epitopes were selected and synthesized to identify promiscuous helper T cell epitopes containing CTL epitopes (Harao M, et al. Int J Cancer 2008; 123: 2616-25.).

Synthetic Peptides and Recombinant Proteins

Three human CDCA1-derived short peptides (SP) that bind to HLA-A2, CDCA1-A2 (65-73), YMMPVNSEV (SEQ ID NO: 3); CDCA1-A2 (351-359), KLATAQFKI (SEQ ID NO: 4), and bind to HLA-A24, CDCA1-A24 (56-64), VYGIRLEHF (SEQ ID NO: 5) were synthesized (purity>95%, Biomatik, Canada). Two overlapping long peptides (LPs), CDCA1 (55-78), IVYGIRLEHFYMMPVNSEVMYPHL (SEQ ID NO: 1); CDCA1 (39-64) NPKPEVLHMIYMRALQIVYGIRLEHF (SEQ ID NO: 2), were synthesized (purity>90%) and tested for their capacity to stimulate CDCA1-specific human CD4$^+$ T cells in vitro. Two HIV peptides that bind to HLA-A24 (HIV-A24, RYLRDQQLL (SEQ ID NO: 6)) and HLA-A2 (HIV-A2, SLYNTYATL (SEQ ID NO: 7)), were used as negative control SP (Tomita Y, et al. Cancer Sci.; 102: 697-705., Tomita Y et al. Cancer Sci.; 102: 71-8.). A LP, a WT1-derived peptide that bind to DR4, WT1-peptide (KRYFKLSHLQMHSRKH (SEQ ID NO: 8)), was used as a negative control LP (Fujiki F et al. J. Immunother. 2007; 30: 282-93.). Peptides were dissolved in dimethylsulfoxide at the concentration of 10 micro g/micro L or 20 micro g/micro L, and stored at −80 degrees C.

The 6His-tagged recombinant whole CDCA1 proteins and truncated CDCA1 proteins that lack both CDCA1-derived Th epitopes recognized by CDCA1 (55-78) and CDCA1 (39-64)-specific Th cells were expressed by *E. coli* BL21 strains with a pET28a vector (Novagen) that has respective cDNA fragments. The truncated CDCA1 protein was used as control protein. Each recombinant protein was purified using a HisTrap FF column (GE Healthcare) according to the manufacturer's instruction. The purity of the proteins was verified by SDS-PAGE.

Generation of TAAs-Specific CD4+ T Cell Lines and Clones

The research protocol for collecting and using peripheral blood mononuclear cells (PBMC) from healthy donors was approved by the Institutional Review Board of Kumamoto University. The present inventors obtained blood samples from 12 healthy donors after receiving their written informed consents. The HLA-A, DRB1 and DPB1 alleles of the healthy donors investigated in this study are determined by DNA typing of HLA genetic variations with polymerase chain reaction and allele-specific probe hybridization, and described in Table 1. PBMCs from healthy volunteers were isolated as described previously (Inoue M, et al. Int. J. Cancer; 127: 1393-403.). CD4+ T cells were purified from PBMC by positive selection using magnetic microbeads coupled with anti-CD4 monoclonal antibody (Miltenyi Biotec, Auburn, Calif., USA). Monocyte-derived dendritic cell (DC) was generated from CD14+ cells by in vitro culture as described previously (Harao M, et al. Int. J. Cancer 2008; 123: 2616-25.) and used as antigen-presenting cell (APC) to induce TAA-specific CD4+ T cells. DCs ($1 \times 10^4$/well) were pulsed with 10 micro g/ml LP for 3 h and irradiated (45 Gy), and then mixed with autologous CD4+ T cells ($3 \times 10^4$/well) in 200 micro l of AIM-V supplemented with 5% human decomplemented plasma in each well of a 96-well, flat-bottomed culture plates. After 7 days, half of the medium was removed from each culture, and then the culture was added fresh medium (100 micro l/well) containing irradiated (50 Gy) autologous PBMCs ($1 \times 10^5$) pulsed with peptide (10 micro g/ml) and 5 ng/ml human recombinant (hr) IL-7. Two days after the second stimulation with peptide, hr IL-2 was added to each well at final concentration of 10 IU/ml. One week later, the stimulated CD4+ T cells in each well were analyzed for specificity in enzyme-linked immunospot (ELISPOT) assays. The T cells showing a specific response to the cognate peptide were transferred to 24-well plate and restimulated at weekly intervals with irradiated autologous PBMCs ($1 \times 10^6$/well) pulsed with the peptide (10 micro g/ml) in medium supplemented with 10 IU/ml hr IL-2 and 5 ng/ml hr IL-7. In some instances, T cells were cloned by limiting dilution for further studies as described previously (Tabata H et al. Hum. Immunol. 1998; 59: 549-60.).

Assessment of T Cell Responses to Peptides and Proteins

The immune response of Th cells to APCs pulsed with peptides and proteins were assessed by IFN-gamma ELISPOT assays (Human IFN-gamma ELISPOT kit, BD Biosciences) as described previously (Tomita Y et al. Cancer Sci.; 102: 697-705.). Briefly, the frequency of peptide-specific CD4+ T cells producing interferon (IFN)-gamma per $3 \times 10^4$ bulk CD4+ T cells upon stimulation with peptide-pulsed PBMCs ($3 \times 10^4$/well), or $1 \times 10^4$ bulk CD4+ T cells upon stimulation with peptide-pulsed HLA-DR-expressing L-cells ($5 \times 10^4$/well) was analyzed. The frequency of cells producing interferon (IFN)-gamma per $1 \times 10^5$ CTLs upon stimulation with peptide-pulsed T2 cells ($2 \times 10^4$/well) was also analyzed. Alternatively, $5 \times 10^3$ protein-loaded DCs were co-cultured with $2 \times 10^4$ CD4+ T cell clones/well. The protein-loaded mature DCs were prepared from positively isolated CD14+ cells (day 0) as described previously (Harao M, et al. Int. J. Cancer 2008; 123: 2616-25.). On day 5, the DCs were cultured in the presence of the recombinant CDCA1 (50 micro g/ml) and OK432. The protein-loaded mature DCs were harvested on day 7, washed and used as stimulator in IFN-gamma ELISPOT assays. To determine restriction HLA molecules involved in antigen presentation, blocking of antigen-induced IFN-gamma production was investigated by adding anti-HLA-DR mAb (L243, Biolegend), anti-HLA-DP mAb, (B7/21, abcam), anti-human HLA-DQ mAb (SPV-L3, abcam), or anti-HLA class I mAb, (W6/32, abcam). All mAbs were used at a final concentration of 5 micro g/ml. All assessments of IFN-gamma ELISPOT assays were carried out in duplicate or triplicate, and results corresponded to mean values.

The immune responses of T-cells to PBMC, L-cells, and murine BM-DC pulsed with peptides (10 micro g/mL) or CDCA1 proteins-loaded human DCs (50 micro g/mL) were assessed by IFN-gamma ELISPOT assays (BD Biosciences, San Jose, Calif.) according to manufacturer's instructions and described previously (Zarour H M et al., Cancer Res. 2000; 60:4946-52.). In briefly, peptide-pulsed PBMCs ($3 \times 10^4$/well), L-cells ($5 \times 10^4$/well), T2 cells ($2 \times 10^4$/well), C1R-A24 cells ($2 \times 10^4$/well), bone marrow-derived DCs (BM-DCs, $2 \times 10^4$/well), or protein-loaded DCs ($5 \times 10^3$/well) were seeded in triplicate or duplicate in the ELISPOT plates as APCs or target cells. To determine the HLA molecules involved in antigen presentation, antigen-induced IFN-gamma production was blocked by adding anti-HLA-DR monoclonal antibody (mAb) (L243, BioLegend), anti-HLA-DP mAb (B7/21, Abcam), anti-human HLA-DQ mAb (SPV-L3, Abcam), or anti-HLA class I mAb (W6/32, Abcam) after seeding APCs or target cells. All mAbs were used at a final concentration of 5 micro g/mL. The APCs or target cells were incubated with mAbs for 1 h at room temperature.

TABLE 1

HLA-A, DR and DP genotypes of healthy donors

| | HLA-A genotype | HLA-DRB1 genotype | HLA-DPB1 genotype |
|---|---|---|---|
| Donor HD1 | A*02:01/02:06 | DRB1*04:05/09:01/DR53 | DPB1*02:01/DPB1*04:02 |
| Donor HD2 | A*24:02/— | DRB1*08:02/15:02 | DPB1*05:01/09:01 |
| Donor HD3 | A*11:01/A31:01 | DRB1*08:03/15:02 | DPB1*02:01/09:01 |
| Donor HD4 | n.t. | DRB1*01:01/04:05/DR53 | DPB1*05:01/09:01 |
| Donor HD5 | A*24:02/A02:01 | DRB1*04:05/DR53 | DPB1*05:01/— |
| Donor HD6 | A*02:06/A31:01 | DRB1*04:01/09:01/DR53 | DPB1*02:01/— |
| Donor HD7 | n.t. | DRB1*04:06/DR*08:03 | DPB1*02:01/04:02 |
| Donor HD8 | A*24:02/31:01 | DRB1*08:03/14:05 | DPB1*02:02/05:01 |
| Donor HD9 | A*26:01/33:03 | DRB1*04:05/13:02 | DPB1*04:01/09:01 |
| Donor HD10 | A*26:01/— | DRB1*04:10/08:02 | DPB1*02:01/05:01 |
| Donor HD11 | A*31:01/33:03 | DRB1*09:01/13:02 | DPB1*03:01/04:01 |
| Donor HD12 | A*01:01/68:01 | DRB1*07:01/13:02 | DPB1*02:01/04:01 |

HLA, human leukocyte antigen;
n.t., not tested

Then, the responder T-cells were harvested, washed, and transferred to the ELISPOT plate in the indicated number of the figures. After incubation for 18 h, spot numbers were counted. HIV-A2, HIV-A24, or WT1-derived LP were used as negative control peptides. In some experiments, unpulsed PBMCs or L-cells were used as negative controls. Cells cultured with PMA (100 ng/ml; Sigma-Aldrich) and ionomycin (500 ng/ml; Sigma-Aldrich) were used as positive controls in all assessments of IFN-gamma ELISPOT assays. Results are presented as means+/−SD.

In the ELISPOT assays for HNC patients, after 1 week of cell culture with CDCA1-LPs, the cells were collected, washed, and cultured in ELISPOT plates ($1\times10^5$/well) with CDCA1 (55-78)-LP, CDCA1 (39-64)-LP, or control LP (HIV-LP) for 18 h. The number of CDCA1-LP-specific Th cells expressed as spot-forming cells/$10^5$ cells was calculated after subtracting control values (background). Responses were scored as positive when the mean number of IFN-gamma spots numbered more than 15 and more than 2-fold over background. The ELISPOT assays on HNC patients' cells were conducted in single, duplicate, or triplicate wells because of the limited number of available cells.

Propagation of CDCA1-A24 (56-64) SP-Specific CTLs by Stimulation with CDCA1 (55-78)-LP in Healthy Donor A: Induction of CDCA1-A24 (56-64) SP-reactive CTLs by stimulation of purified CD8$^+$ T-cells with CDCA1-A24 (56-64) SP was performed as described previously. (Tomita Y, et al. Cancer Sci. 2011; 102:71-8., Imai K, et al. Clin. Cancer Res. 2008; 14:6487-95.) To assess the expansion capacity of CDCA1-A24 (56-64) SP-specific CTLs by stimulation with CDCA1 (55-78)-LP-pulsed DCs, the CDCA1-A24 (56-64) SP-specific bulk CTLs obtained from an HLA-A24$^+$ donor (HD2; $2\times10^6$/well, 24-well plates, HD5; $2\times10^5$/well, 48-well plates) were stimulated with 16 micro M CDCA1 (55-78)-LP or control-LP-pulsed autologous DCs (HD2; $2\times10^5$/well, HD5; $5\times10^4$/well). The LP-pulsed mature DCs (3 h) were irradiated and washed, then used as antigen-presenting cells (APCs). On days 1 and 7, rh IL2 (20 IU/mL) and rhIL-7 (5 ng/mL) were added. After CTLs were established from HD2 and HD5, their recognition specificity and cytotoxic activity were evaluated by the following protocols (B) and (C), respectively.

B(HD2); Before LP stimulation (day 0) and on days 5, 7, 8, and 10 after stimulation, an aliquot of cultured cells ($1\times10^5$ cells) was stained with a PE-labeled tetramer of the HLA-A*24:02/CDCA1-A24 (56-64)-complex (MBL, Nagoya, Japan) with an FITC-labeled anti-human CD8 mAb (clone T8, Beckman Coulter, Brea, Calif.). A PE-labeled tetramer of the HLA-A24 (A*24:02)/HIV-A24 (RYLRDQQLL; SEQ ID NO: 6) complex was used as negative control.

C(HD5); After 1 week of cell culture, the cells were collected, washed, and cultured in ELISPOT plates ($1\times10^5$/well) for 18 h. The number of IFN-gamma producing CD8$^+$ T-cells upon stimulation with CDCA1-A24$_{56-64}$SP-pulsed or HIV-A24 SP (background)-pulsed C1R-A2402 cells ($2\times10^4$/well) was counted by ELISPOT assay. (Dobrzanski M J. et al. Frontiers in oncology 2013; 3:63) The number of CDCA1-A24$_{56-64}$SP-specific CD8$^+$ T-cells expressed as spot-forming cells/$10^5$ cells was calculated after subtracting control values (background). HIV-A24 SP was used as negative control SP.

Expansion of CDCA1-A24 (56-64) SP-Specific CTLs by Stimulation with CDCA1-LPs in HNC Patients Vaccinated with CDCA1-A24 (56-64) SP PBMCs from 5 HNC patients (HNC26, 29, 31, 39, 109) vaccinated with CDCA1-A24 (56-64) SP were cultured with a mixture of CDCA1 (55-78)-LP and CDCA1 (39-64)-LP (10 micro g/mL each) in a 24-well plate ($2\times10^6$/well); rhIL-2 and rhIL-7 were added on day 0 and day 2. On day 0 (ex vivo) and day 7, the PBMCs were stained with CDCA1-A24 (56-64)-specific tetramer.

Cytokine Assays

T cells ($1\times10^4$/well) were cultured with L-DR4 ($5\times10^4$/well) in the presence of CDCA1 (55-78) in 96-well culture plate. After 20 h, culture supernatants were collected and cytokine (IFN-gamma, GM-CSF, TNF-alpha, M1P1 beta, IL-4, IL-17) level was measured using the Bio-Plex system (Bio-Rad) according to manufacturers' instructions.

CD107a Mobilization Assay

To identify degranulating CD8$^+$ or CD4$^+$ T lymphocytes stimulated with the peptides, the CD107a exposed on the cell surface was analyzed by flow cytometry. (Rubio V et al. Nat. Med. 2003; 9: 1377-82., Betts M R, et al. J. Immunol. Methods 2003; 281: 65-78.) Briefly, A CD107a mobilization assay was performed as described previously. (Tomita Y et al. Cancer Sci. 2011 January; 102(1): 71-8.) The CDCA1-derived peptide or control peptide (1 micro g/ml) was added as a stimulant, and FITC-labeled anti-human CD107a mAb or FITC-labeled isotype control mouse IgG1 and monensin were added to each well. Cells were cultured for 5 h at 37 degrees C. After culture, the peptide-stimulated Th cells or CTLs were stained with PE-conjugated anti-human CD4 antibody (eBioscience, San Diego, Calif.) and PE-conjugated anti-human CD8 antibody (Biolegend), respectively, and analyzed by flow cytometry (FACScan; BD Biosciences).

In Vitro Cross-presentation Assay and Human CTL Response Analysis

An HLA-A24$^+$ donor (HD2)-derived DCs were kept alive or fixed for 3 min in 0.1% glutaraldehyde (Sigma-Aldrich), pulsed with peptides (16 micro M) for 3 h, and washed 3 times. OK432 (0.1 KE/mL, Chugai Pharmaceutical Co, Tokyo, Japan) was added to induce the maturation of DCs during and after the peptide pulse. CDCA1-A24 (56-64)-reactive bulk CTLs were added at a 2:1 ratio for 6 h in medium containing 10 micro g/mL brefeldin A (Sigma-Aldrich). The brefeldin A was added to inhibit protein secretion during the stimulation. IFN-gamma production by the CDCA1-A24 (56-64)-specific CTLs was measured by intracellular labeling. The cells were stained with a FITC-labeled anti-human IFN-gamma mAb (BioLegend) in combination with a PerCP-labeled anti-human CD8 mAb (BioLegend) and a PE-labeled CDCA1-A24 (56-64)-specific tetramer. Data acquisition was performed on a FACSCalibur (BD Biosciences) and data files were analyzed with FlowJo software (Tree Star, Ashland, Oreg.).

To assess the induction of CDCA1-A2 (65-73) SP or CDCA1-A24 (56-64) SP reactive CTLs in vitro by cross-presentation of CDCA1 (55-78) LP, CDCA1 (55-78) LP-loaded DCs isolated from a HLA-A2 or A24-positive donor were used as APCs. CD14$^+$ cells were isolated (day 0) and cultured in the presence of hr IL4 (10 ng/ml) and GM-CSF (100 ng/ml). CDCA1 (55-78) (10 micro g/ml) and OK432 were added on day 5. The LP-loaded mature DCs were harvested on day 7, washed and used as APCs. Stimulations of human CD8$^+$ T cells with the LP-loaded DCs from HLA-A2 positive healthy donors were performed as described previously (Imai K, et al. Br. J. Cancer; 104: 300-7.). After three stimulations of CD8$^+$ T cells with CDCA1 (55-78) LP-loaded-DCs, The number of IFN-gamma producing CD8$^+$ T cells upon stimulation with the CDCA1-A2 (65-73), HIV-A2 peptides-pulsed T2 or CDCA1-A24 (56-64) SP-pulsed C1R-A2402 cells was counted by an ELISPOT assay.

In Vivo Cross-Presentation Assay

HLA-A2 (HHD) and HLA-A24 (HHH) transgenic mice (Tgm) were kindly provided by Dr. F. A. Lemonnier. (Firat H, et al. Eur. J. Immunol. 1999; 29: 3112-21., Jung K O, et al. J. Virol. 2012; 86:7616-24.). Mice were intradermally injected at the base of the tail with CDCA1-LP solution (HLA-A2 Tgm, 50 micro g/mouse; HLA-A24 Tgm 100 micro g/mouse) emulsified in incomplete Freund's adjuvant (IFA) at 7-day intervals. Seven days after the second or third vaccination with CDCA1-derived LPs, CD8+ T-cells were isolated from inguinal lymph nodes by positive selection with magnetic microbeads (Miltenyi Biotec, Auburn, Calif., USA). The number of IFN-gamma producing CD8+ T-cells in response to stimulation with SP-pulsed BM-DCs or C1R-A2402 cells was counted by ex vivo ELISPOT assay.

The Synergistic Effect of CDCA1 (55-78)-LP on Induction of CDCA1-Specific CTLs

PBMCs obtained from HLA-A2+/DR4+ HD1, from whom the CDCA1 (55-78)-LP-specific Th cell clones (Th-clone) were generated, were plated in 24-well plates ($3\times10^6$/well), followed by addition of SP alone (CDCA1-A2 (351-359), 20 micro g/mL), SP+LP (CDCA1 (55-78)-LP, 20 micro g/mL), SP+Th-clone ($5\times10^5$/well), or SP+LP+Th-clone in a final volume of 2 mL. After culture for 7 days, these peptides and IL-2 (20 U/mL) were added, then IL-15 (5 ng/mL) was added on day 9. On day 11, cells were stained with a PE-labeled tetramer of the HLA-A*02:01/CDCA1-A2 (351-359)-complex with an FITC-labeled anti-human CD8 mAb. Lytic activity was tested in standard chromium release assays. (Inoue M et al., Immunol. Lett. 2009; 126:67-72., Monji M etal., Clin. Cancer Res. 2004; 10:6047-57.).

CDCA1 (55-78) LP-specific bulk CD4+ T-cells ($1\times10^5$ cells/well, 48-well plates) and CDCA1-A24 (56-64) SP-specific bulk CD8+ T-cells ($1\times10^5$ cells/well) derived from HD2 were cultured with autologous DCs ($2\times10^4$ cells/well) in the presence of CDCA1-A24 (56-64) SP alone (10 micro g/mL; SP), CDCA1-A24$_{56-64}$SP+control LP (10 micro g/mL each; Control LP+SP), or CDCA1-A24 (56-64) SP+CDCA1 (55-78) LP (10 micro g/mL each; CDCA1 (55-78) LP+SP) without addition of any cytokine. Induction of CDCA1-A24 (56-64) SP-specific bulk CTLs from an HLA-A24+/DR15+ donor (HD2) by stimulation with CDCA1-A24 (56-64) SP was performed as described previously. (Shedlock D J, Shen H. Science 2003; 300:337-9.) After 1-week in vitro culture with peptides, the cultured cells were stained with PE-labeled tetramer of the HLA-A*24:02/CDCA1-A24$_{56-64}$ complex (MBL, Nagoya, Japan), and FITC-labeled anti-human CD8 mAb (BioLegend).

Assessment of CDCA1-LP Specific CD4+ T-Cell Responses in HNC Patients Immunized with CDCA1-A24 (56-64) SP The PBMCs from the heparinized blood of HNC patients were isolated by means of Ficoll-Conray density gradient centrifugation. Fresh PBMCs from HNC patients or healthy donors were cultured with a mixture of CDCA1 (39-64)-LP and CDCA1 (55-78)-LP (10 micro g/mL each) in a final volume of 2 ml AIM-V supplemented with 5% human decomplemented plasma at 37 degrees C. ($2\times10^6$/well, 24-well plates); IL-2 and IL-7 were added on day 0 and day 2. After 1 week of cell culture, the number of antigen-specific IFN-gamma producing T-cells was counted by ELISPOT assay. This study was conducted in a laboratory that operates under exploratory research principles, and was performed using investigative protocols. The inventors acknowledge the recommendations of the Minimal Information About T-cell Assay (MIATA) reporting framework for human T-cell assays (Britten C M et al., Immunity 2012; 37:1-2.).

Tetramer Assay for Induced TAAs-Specific CTLs

After the PBMCs from a HLA-A2 and DR4-positive healthy donor-HD1 from whom CDCA1 (55-78)-specific Th cell clones were generated, were plated at concentration of $3\times10^6$/well in 24-well plates, mixed SPs alone (CDCA1-A2 (65-73)+CDCA1-A2 (351-359), 20 micro g/ml respectively), mixed SPs+CDCA1 (55-78) LP (20 micro g/ml), mixed SPs+Th clone ($5\times10^5$/well), or mixed SPs+CDCA1 (55-78) LP+Th clone were added to the cell culture in final volume of 2 ml. After the culture for 7 days, these peptides and hr IL-2 (20 U/ml) were added, then hr IL-15 (5 ng/ml) was added on day 9. On day 11 of the culture, the cells were harvested, stained with a PE-labeled tetramer of the HLA-A*02:01/CDCA1-A2 (65-73) peptide complex or HLA-A*02:01/CDCA1-A2 (351-359) peptide complex (MBL, Nagoya, Japan) in combination with a FITC-labeled anti-human CD8 mAb (clone T8, Beckman Coulter, Brea, Calif.), and analyzed by flow cytometry. PBMC from another donor from whom CDCA1 (55-78)-specific Th cell clones were tested based on the procedure described above.

Statistical Analysis

Two-tailed Student's t-test (bar graphs), Fisher's exact test, or nonparametric Mann-Whitney U test (scatter-dot graph) was used to evaluate the statistical significance of differences in ELISPOT data. P values less than 0.05 were considered to be statistically significant. Statistical analysis was performed with a commercial statistical software package (StatView 5.0, Abacus Concepts, Calabasas, Calif.).

Results

Prediction and Selection of Potential Promiscuous HLA Class II-Binding Peptides Containing CTL Epitopes of CDCA1

To identify the potential promiscuous HLA-class II binding Th cell epitopes of CDCA1, the present inventors first examined the amino acid sequence of CDCA1 using a computer algorithm (Wang P, et al. BMC Bioinformatics; 11: 568., Wang P, et al. PLoS Comput. Biol. 2008; 4: e1000048.). Interestingly, the inventors found one region (CDCA1 (39-78)) of CDCA1 protein sequence predicted as a potent promiscuous HLA class II-binding peptide by the computer algorithm was very proximal to the CTL epitopes (FIG. 1). Therefore, the inventors selected and synthesized two candidate LP (CDCA1 (39-64) and CDCA1 (55-78)) that have overlapping high consensus percentile ranks for multiple HLA-class II molecules HLA-DR4, HLA-DR15 and HLA-DP2 (DPB1*02:01), and include natural 9-mer peptides recognized by HLA-A2- or -A24-restricted CTLs (FIG. 1A and Table 2) for subsequent analyses.

TABLE 2

Algorithm scores of long peptides derived from CDCA1.

| Amino acid residues position | Algorithm score | | |
|---|---|---|---|
| | HLA-DR4 (DRB1*04:05) | ILA-DR15 (DRB1*15:02) | HLA-DP2 (DPB1*02:01) |
| 39-53 | 7.0 | 1.7 | 29.5 |
| 40-54 | 6.9 | 1.7 | 13.0 |
| 41-55 | 2.7 | 0.5 | 10.2 |
| 42-56 | 2.6 | 0.5 | 10.2 |
| 43-57 | 2.2 | 0.5 | 10.2 |
| 44-58 | 2.3 | 0.5 | 10.2 |
| 45-59 | 2.3 | 0.5 | 10.2 |
| 46-60 | 3.8 | 0.5 | 10.2 |

TABLE 2-continued

Algorithm scores of long peptides derived from CDCA1.

| Amino acid residues position | Algorithm score | | |
|---|---|---|---|
| | HLA-DR4 (DRB1*04:05) | ILA-DR15 (DRB1*15:02) | HLA-DP2 (DPB1*02:01) |
| 47-61 | 3.0 | 0.5 | 10.2 |
| 48-62 | 6.0 | 0.5 | 11.1 |
| 49-63 | 6.2 | 0.5 | 10.2 |
| 50-64 | 8.2 | 0.5 | 4.5 |
| 51-65 | 8.2 | 0.5 | 4.1 |
| 52-66 | 13.8 | 0.5 | 4.2 |
| 53-67 | 14.0 | 0.5 | 3.8 |
| 54-68 | 24.4 | 1.1 | 4.5 |
| 55-69 | 8.9 | 1.0 | 6.0 |
| 56-70 | 8.9 | 1.0 | 8.1 |
| 57-71 | 8.9 | 1.0 | 11.1 |
| 58-72 | 0.1 | 1.0 | 11.4 |
| 59-73 | 0.06 | 1.0 | 10.4 |
| 60-74 | 0.04 | 1.0 | 12.6 |
| 61-75 | 0.03 | 1.0 | 14.7 |
| 62-76 | 0.06 | 1.4 | 35.4 |
| 63-77 | 0.1 | 1.4 | 30.9 |
| 64-78 | 0.4 | 1.4 | 35.3 |

Peptide-binding algorithm scores for indicated HLA-class II genotypes are indicated for each 15 amino acid sequence of CDCA1 peptide (39-78).

Figure 2A:
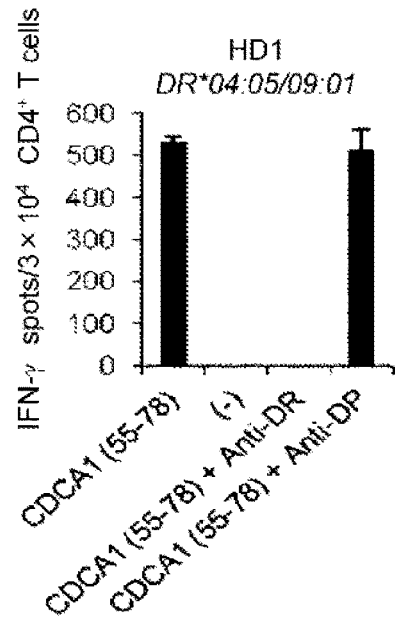
FIG. 2A.
Figure 2A:
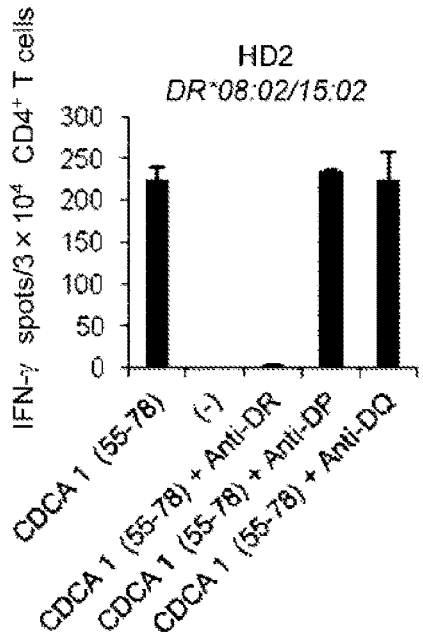
Figure 2A:
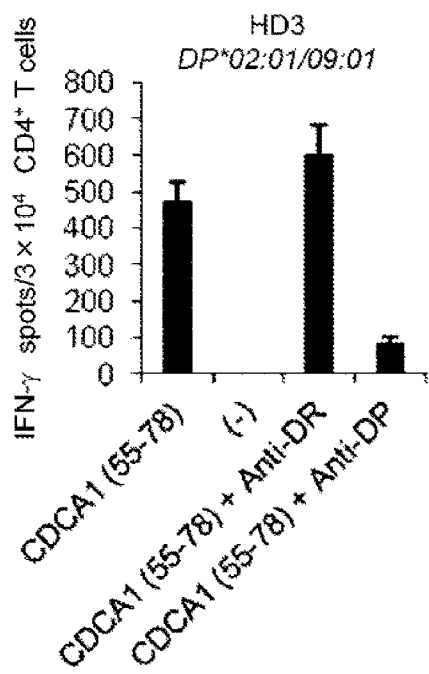

Identification of CDCA1-Derived and Promiscuous HLA Class II-Binding Th Cell Epitopes Naturally Including CTL Epitopes The present inventors assessed whether these two selected synthetic LPs were able to generate CDCA1-specific Th cells. CD4+ T cells of PBMCs from five healthy donors were stimulated at weekly intervals with autologous DCs and PBMCs pulsed with CDCA1 (55-78) peptide. After at least three times stimulations, CDCA1 (55-78)-specific responses of the cultured CD4+ Th cells were examined by IFN-gamma ELISPOT assays. In three HLA-DR4-positive healthy donors, the generated Th cell lines produced a significant amount of IFN-gamma in response to CDCA1 (55-78) (FIGS. 2A and B). To elucidate HLA-restriction of the Th cell lines, the mAb against HLA-DR or HLA-DP was used. The IFN-gamma production of Th cell lines against CDCA1 (55-78) were significantly reduced when HLA-DR-specific mAb was added, whereas HLA-DP-specific mAb showed no effect (FIGS. 2A and B).

Figure 3A:
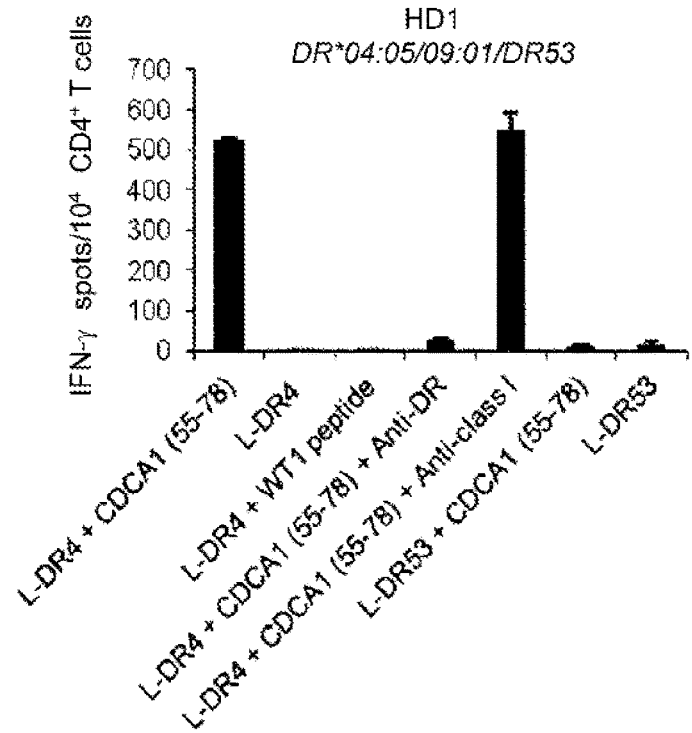
FIG. 3A.
Figure 3A:
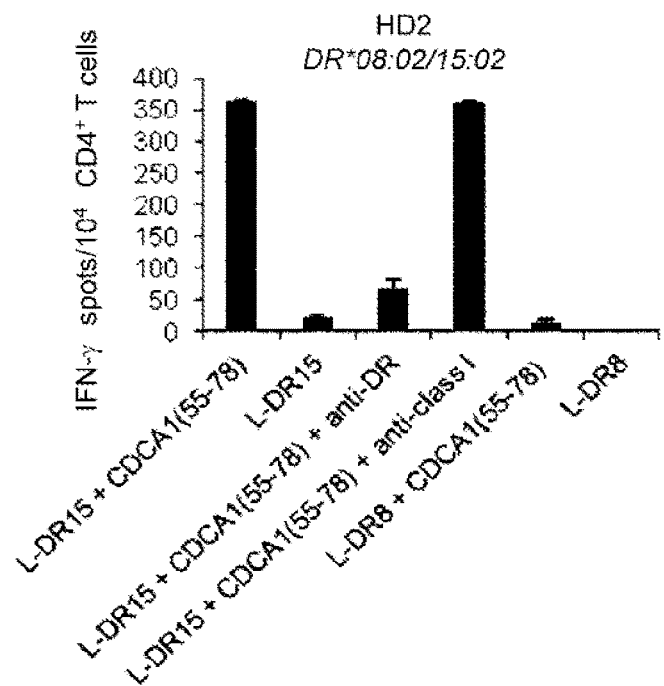
Figure 3B:
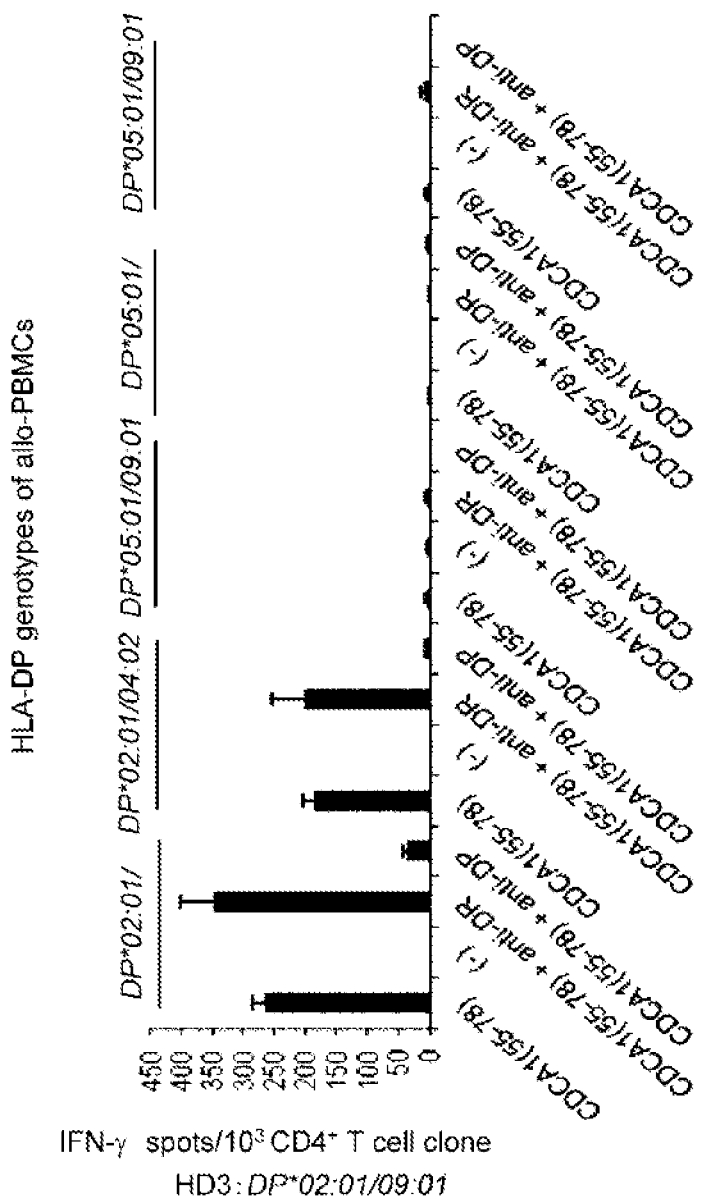
FIG. 3B.
Figure 3C:
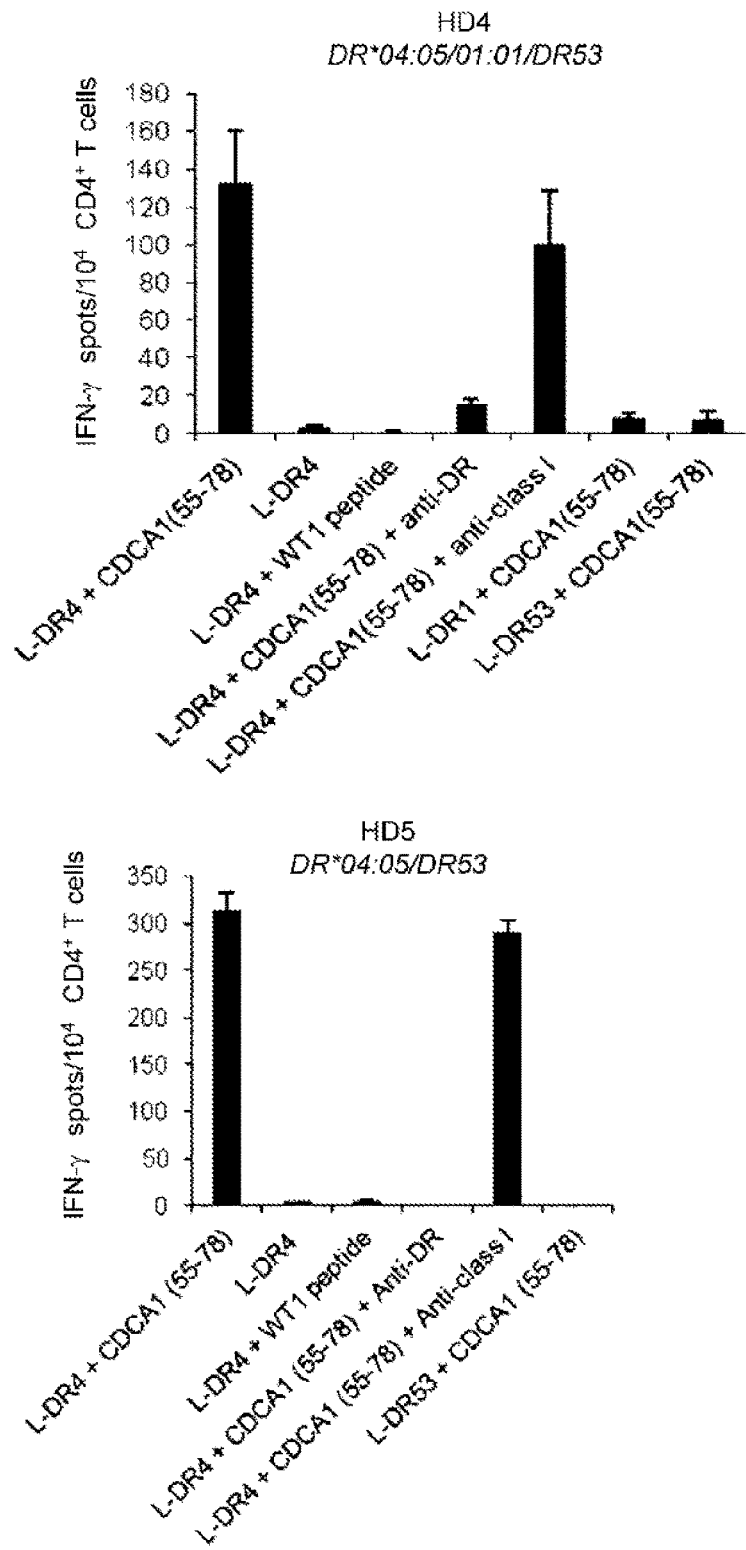
FIG. 3C.

To further analyze the HLA-restriction, the reactivity of Th cells against peptide-pulsed L-DR4, L-DR53 or L-DR1 cells was tested. Bulk Th cell lines generated from three DR4-positive healthy donors specifically recognized L-DR4 cells pulsed with CDCA1 (55-78), but not L-DR4 cells, an irrelevant peptide (WT1-peptide)-pulsed L-DR4 cells, CDCA1 (55-78) peptide-pulsed L-DR53 cells or CDCA1 (55-78)-pulsed L-DR1 cells. The IFN-gamma production of Th cell lines against CDCA1 (55-78)-pulsed L-DR0405 cells were significantly inhibited by addition of anti-HLA-DR mAb (L243), but not the anti-HLA-class I mAb (W6/32) (FIGS. 3A, B and C). These results clearly indicated that CDCA1 (55-78) was presented by HLA-DR4 in these Th cell lines.

To investigate whether CDCA1 (55-78) can bind other HLA class II molecules and induce Th cell responses, CD4+ T cells from HLA-DR4-negative two healthy donors were stimulated with CDCA1 (55-78)-pulsed autologous DCs and PBMCs. The Th cell line generated from an HLA-DR15-positive donor-HD2 specifically produced a significant amount of IFN-gamma in response to CDCA1 (55-78)-pulsed PBMCs and L-DR15 cells, but not CDCA1 (55-78)-pulsed L-DR8 cells. The IFN-gamma production of Th cell line against CDCA1 (55-78)-pulsed PBMCs or L-DR15 cells were significantly inhibited by addition of anti-HLA-DR mAb, but not the HLA-DP-, HLA-DQ- or HLA-class I-specific mAbs (FIG. 2A and FIG. 3A, B). These results clearly indicate that CDCA1 (55-78) was presented by HLA-DR15 in this T cell line.

The Th cell line generated from an HLA-DP2-positive donor-HD3 by stimulations with CDCA1 (55-78) also specifically produced a significant amount of IFN-gamma in response to CDCA1 (55-78) and this response was significantly inhibited by addition of anti-HLA-DP mAb, but not the HLA-DR-specific mAb (FIG. 2A). Because the inventors didn't have L cells transduced with HLA-DP2 and HLA-DR9 genes, allogeneic PBMCs from five different donors as APCs were used to determine shared restriction HLA-DP molecules. CDCA1 (55-78)-specific clone was obtained by limiting dilution of this DP-restricted bulk CD4+ Th cell line from the donor-HD3. Consequently, the CDCA1 (55-78)-specific clone showed specific response to CDCA1 (55-78) peptide only in the presence of DP2-expressing allogeneic PBMCs in IFN-gamma ELISPOT assays, and the IFN-gamma production was significantly inhibited by addition of anti-HLA-DP mAb, but not the HLA-DR-specific mAb. These results suggest that the DP-restricted Th cell line derived from the donor-HD3 is restricted by HLA-DP2 (FIG. 3A, B).

Thus, the CDCA1 (55-78) has capability of binding to HLA-DR4, HLA-DR15 and HLA-DP2 suggesting that CDCA1 (55-78) is the Th cell epitope presented by promiscuous and frequent HLA class II molecules in the Japanese population.

Figure 3D:
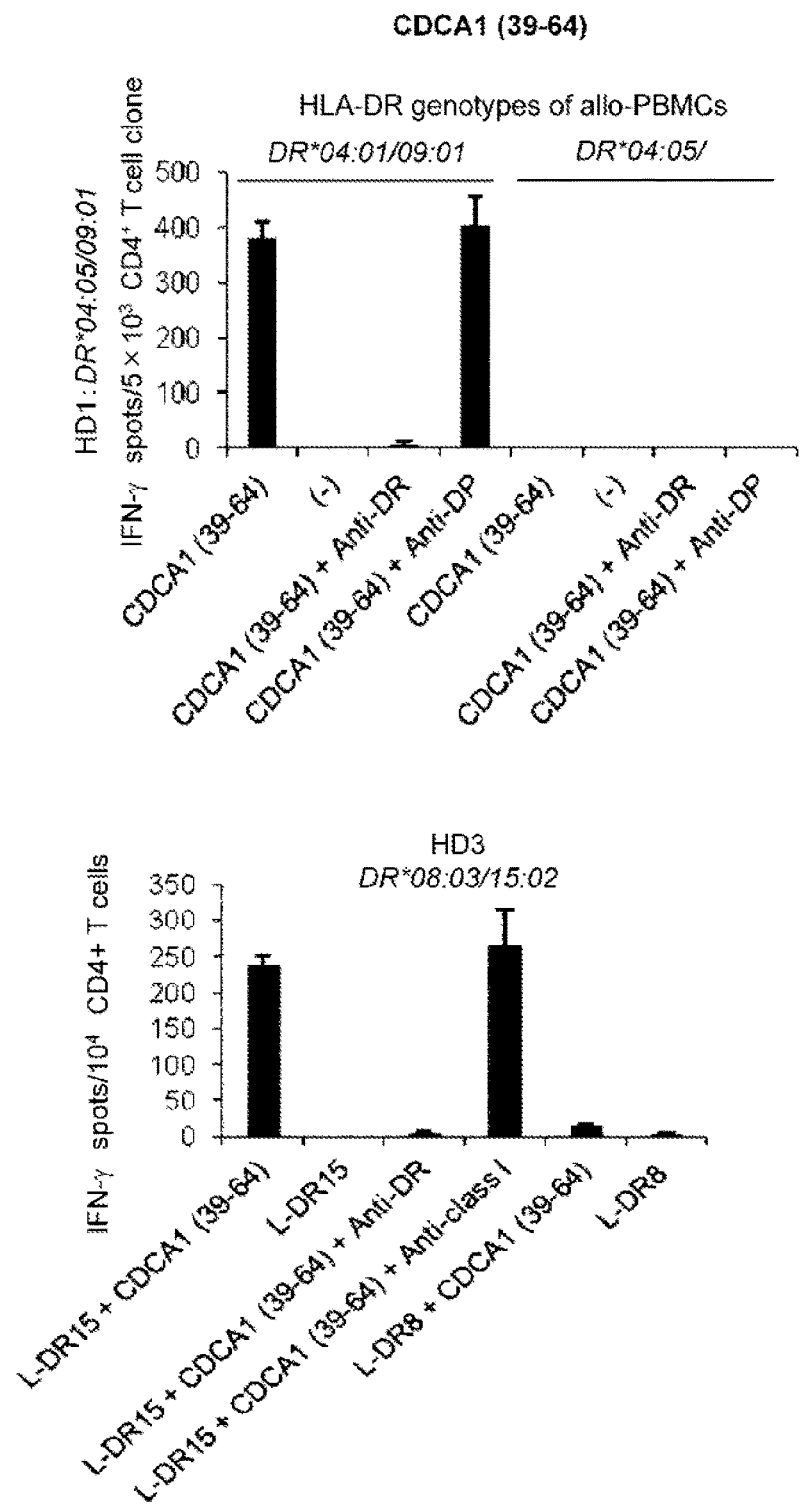
FIG. 3D.
Figure 4A:
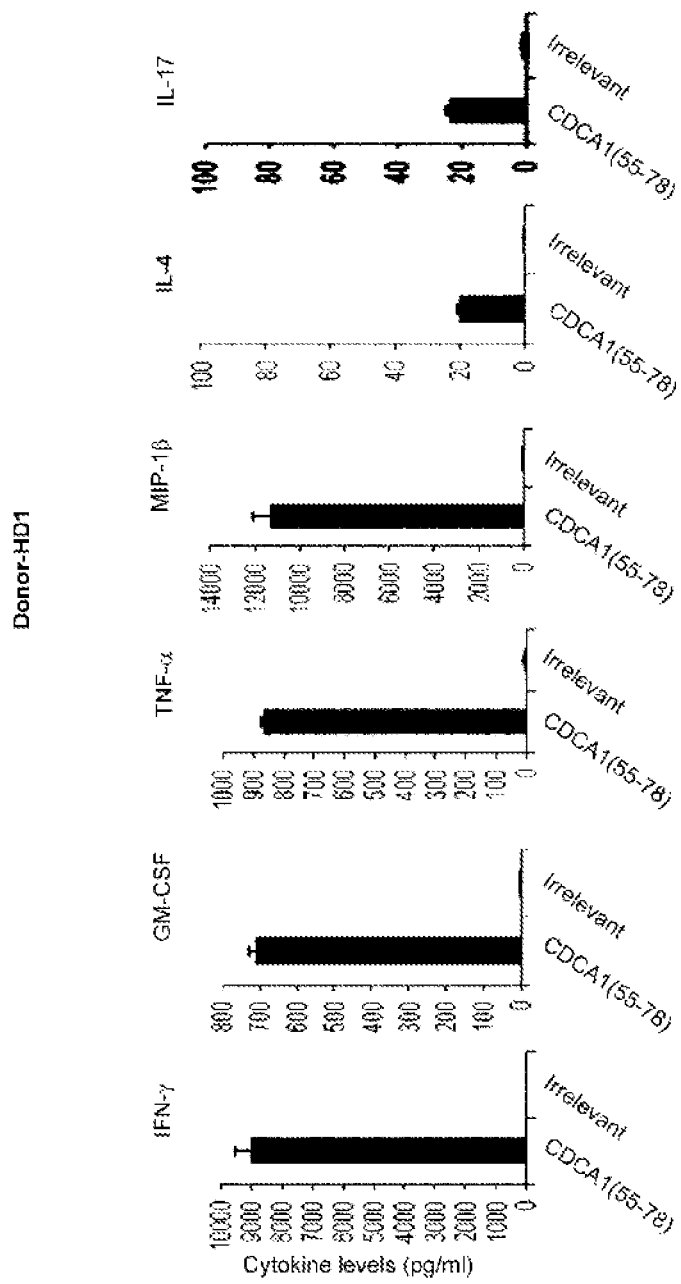
FIG. 4A.
Figure 4B:
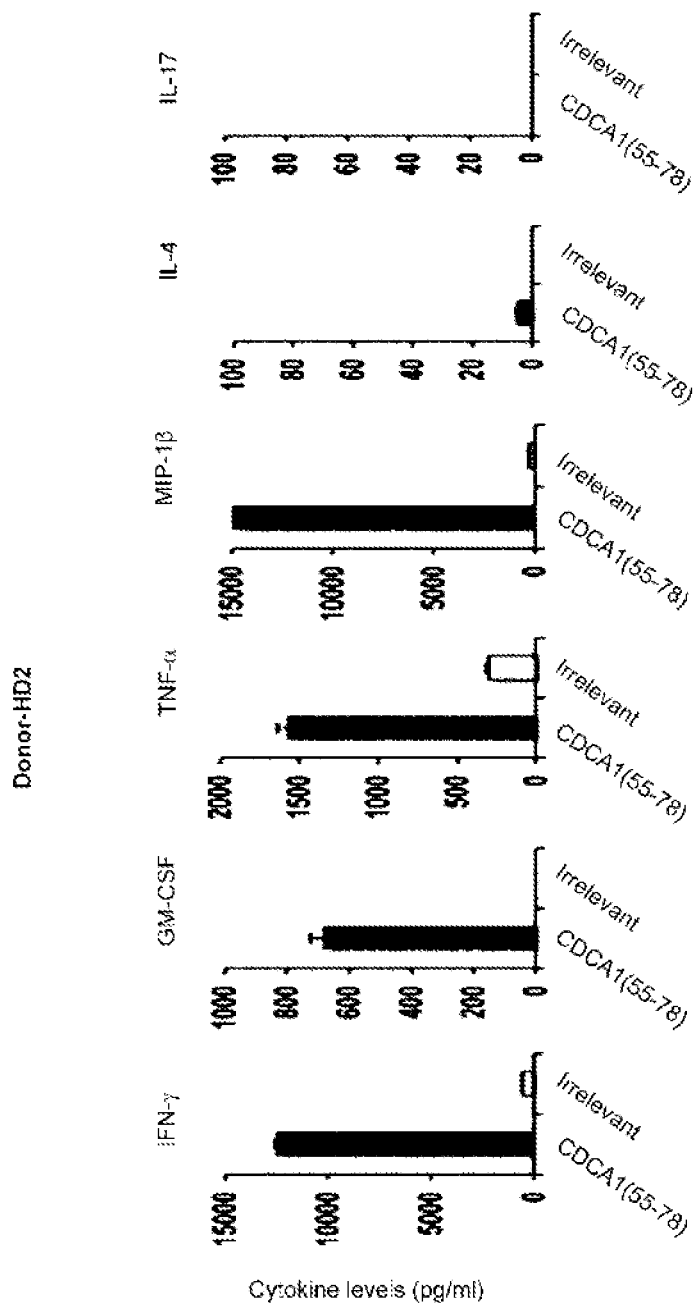
FIG. 4B.
Figure 4C:
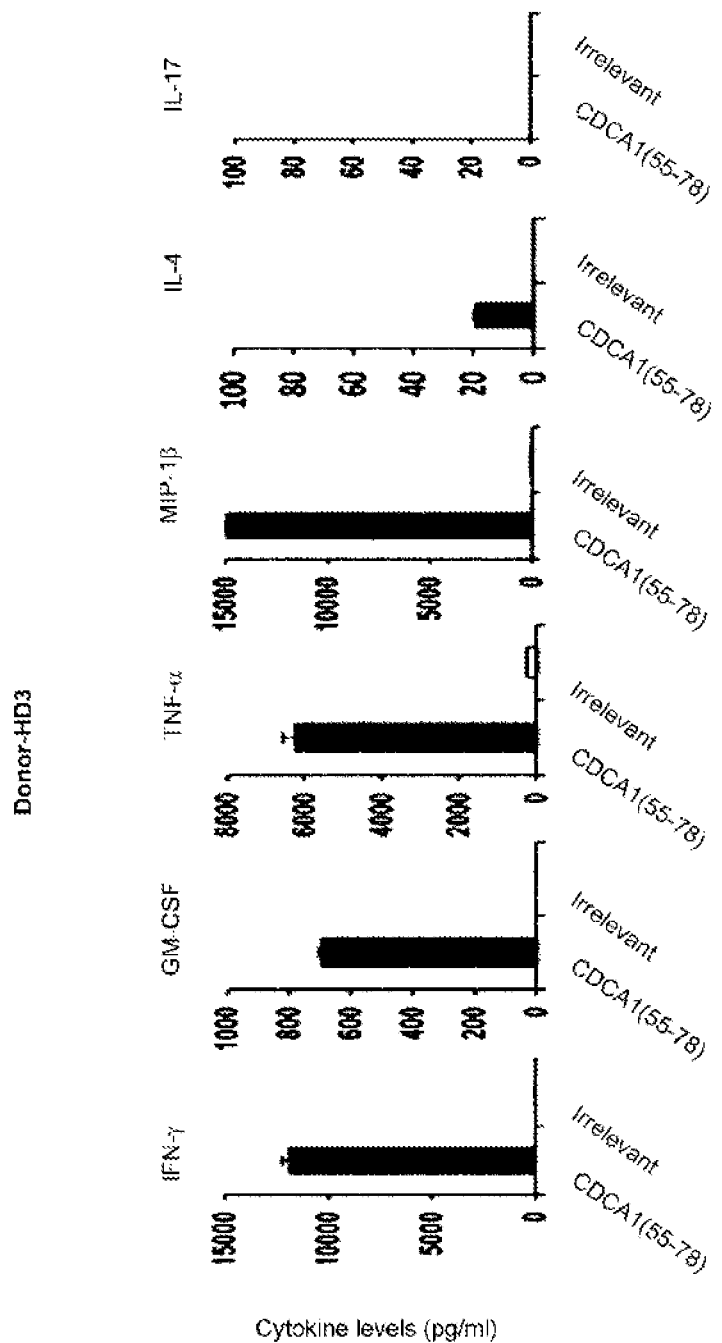
FIG. 4C.
Figure 4D:
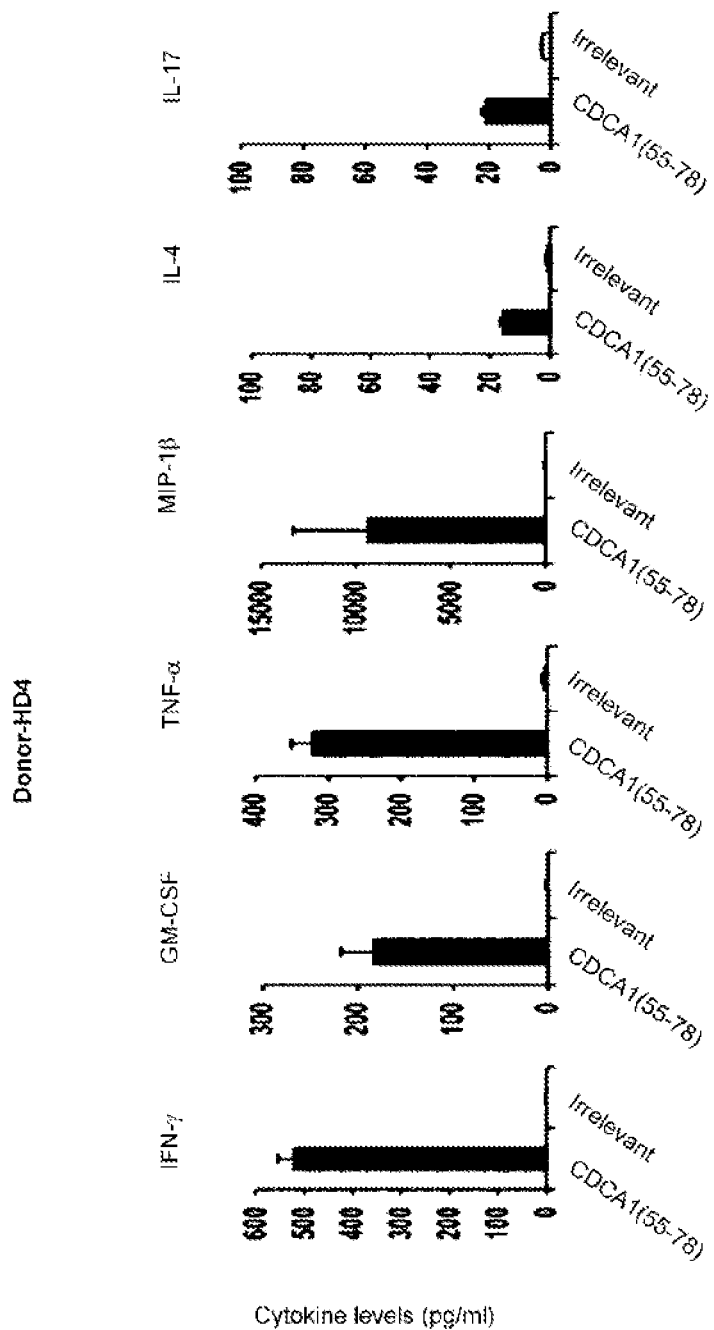
FIG. 4D.
Figure 4E:
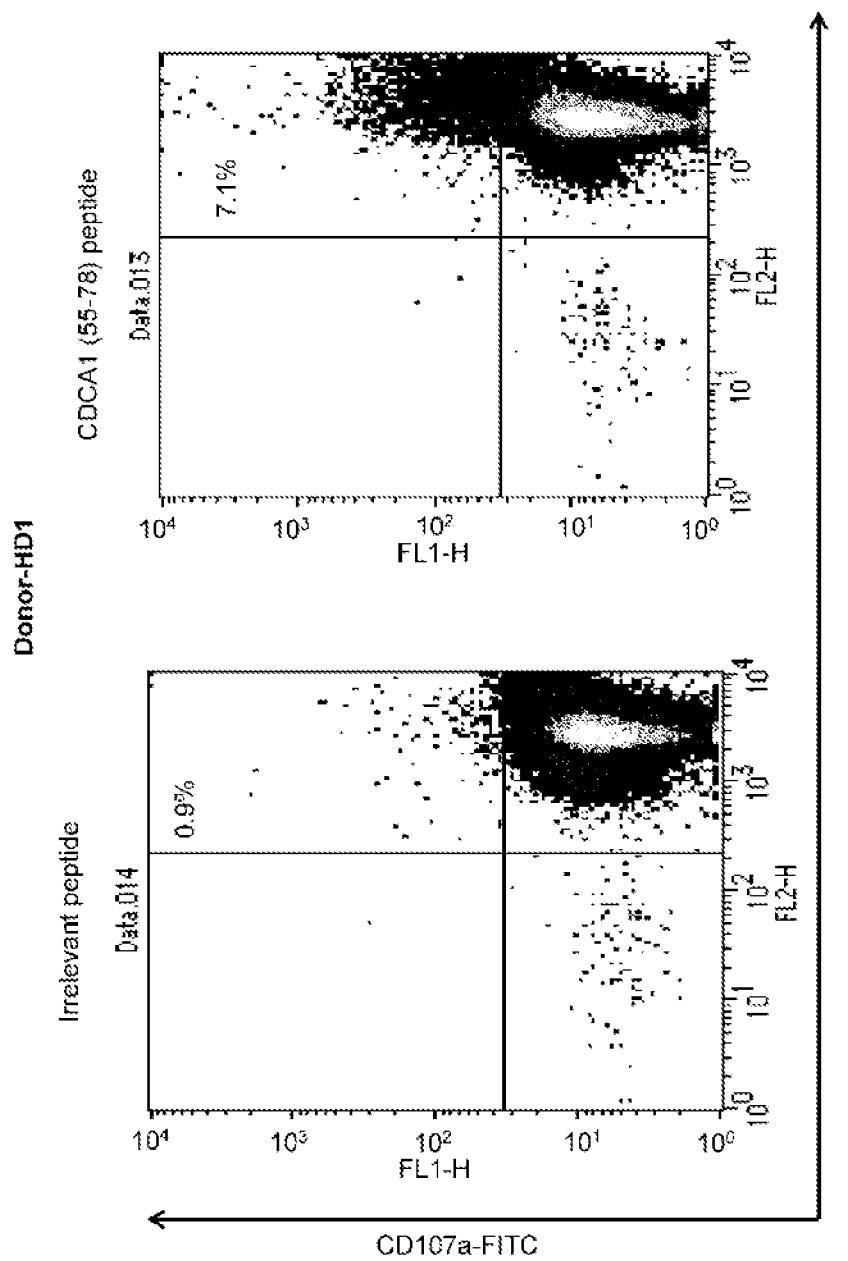
FIG. 4E.
Figure 4F:
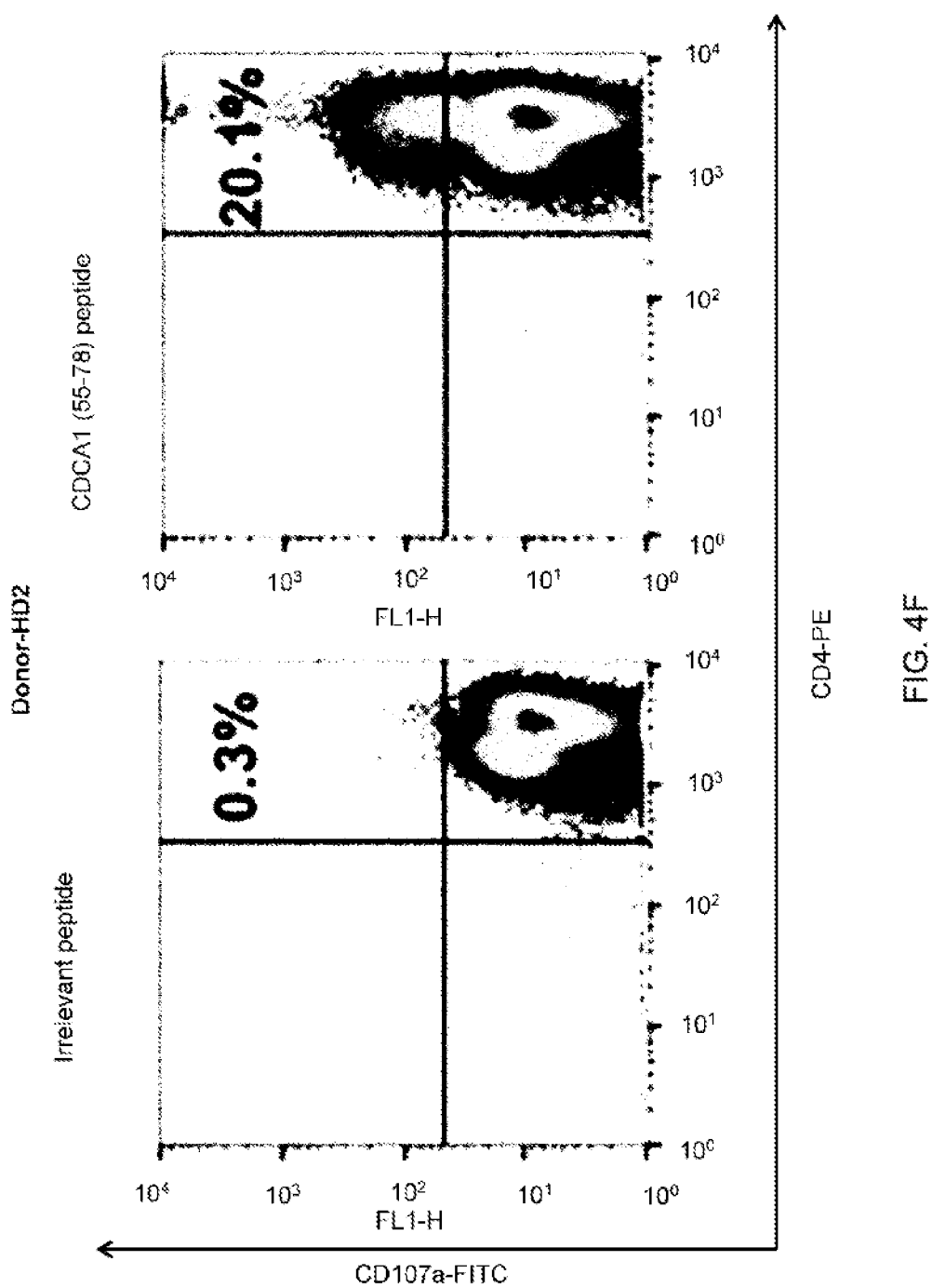
FIG. 4F.
Figure 4G:
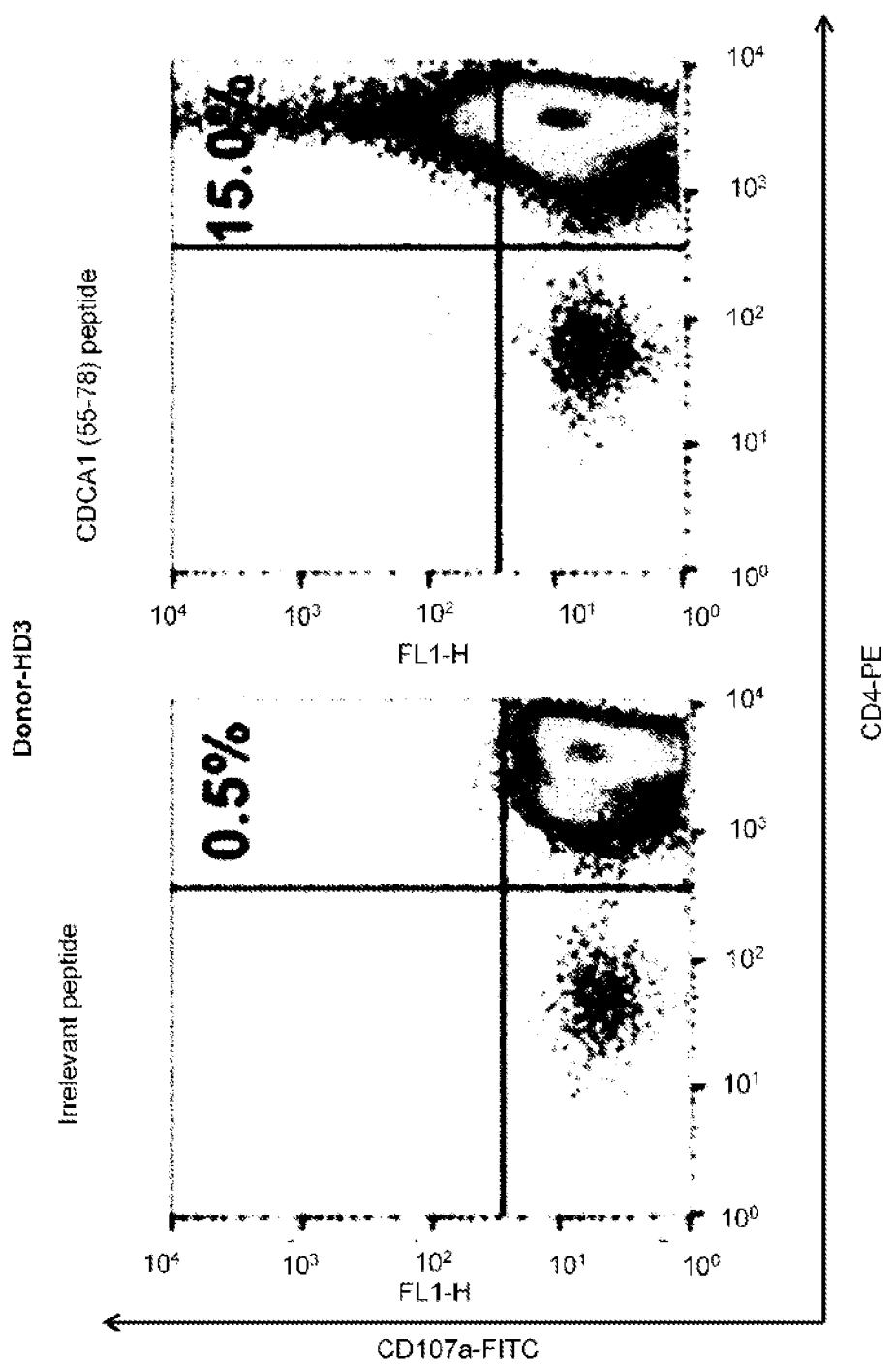
FIG. 4G.
Figure 4H:
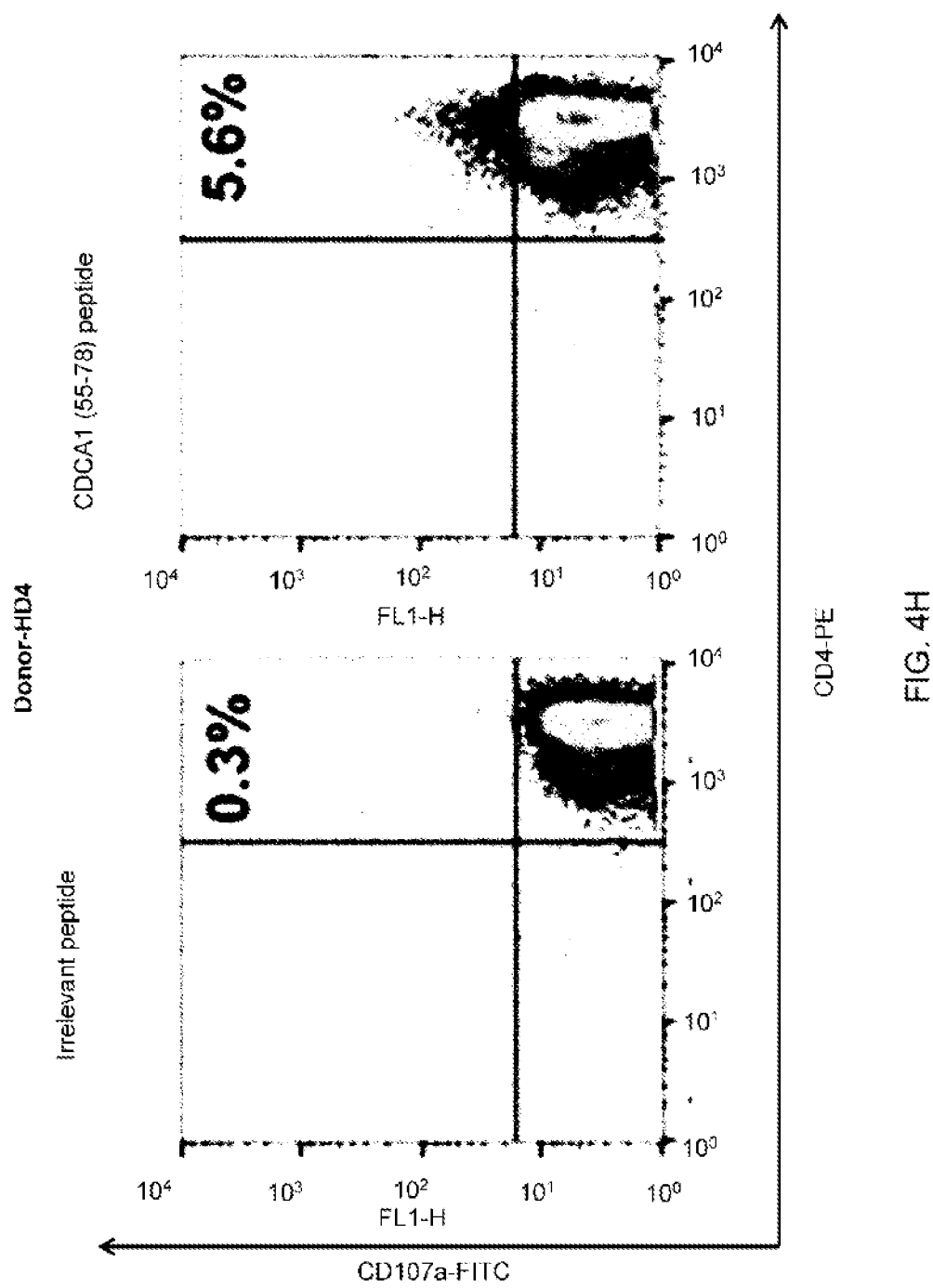
FIG. 4H.

Next, the present inventors assessed whether another peptide, CDCA1 (39-64) was able to generate specific Th1 cell. CD4+ T cells of PBMCs from two healthy donors were stimulated at weekly intervals with autologous DCs and PBMCs pulsed with CDCA1 (39-64). CDCA1 (39-64)-specific responses of the cultured CD4+ Th cells were examined in IFN-gamma ELISPOT assays. In an HLA-DR4-, HLA-DR9, HLA-DR53-positive healthy donor-HD1, the generated Th cell lines produced a significant amount of IFN-gamma in response to CDCA1 (39-64) (FIG. 2C) and this response was significantly reduced when HLA-DR-specific mAb was added, whereas HLA-DP-specific mAb showed no effect. To further analyze the HLA-restriction, the reactivity of Th cells against peptide-pulsed L-DR4 and L-DR53 was tested, but this DR-restricted bulk CD4+ Th cells generated from this donor didn't recognize CDCA1 (39-64)-pulsed L-DR4 and L-DR53 cells (data not shown). Therefore, the present inventors considered that this CD4+ Th cell line was HLA-DR9-restricted Th cells. To confirm this, a CDCA1 (39-64)-specific clone was obtained by limiting dilution of this DR-restricted bulk CD4+ Th cell line. Consequently, the Th clone showed specific response to CDCA1 (39-64) only in the presence of DR9-expressing allogeneic PBMCs in IFN-gamma ELISPOT assays and the IFN-gamma production was significantly inhibited by addition of anti-HLA-DR mAb, but not anti-HLA-DP mAb. These results indicated that this Th clone was restricted by DR9 (FIG. 3D).

To investigate whether CDCA1 (39-64) can bind another HLA class II molecule and induce Th cell responses, CD4+ T cell from an HLA-DR9-negative healthy donor was stimulated with CDCA1 (39-64)-pulsed autologous DC and PBMC. The generated Th cell by stimulations with CDCA1 (39-64) specifically produced a significant amount of IFN-gamma in response to CDCA1 (39-64)-pulsed PBMC and L-DR15 cells, but not CDCA1 (39-64) peptide-pulsed L-DR8 cells. This IFN-gamma production of Th cell line was significantly inhibited by addition of anti-HLA-DR mAb, but not anti-HLA-DP, anti-HLA-DQ or anti-HLA-class I mAb (FIG. 2C and FIG. 3D). These results indicated that this Th cell was restricted by HLA-DR15.

Taken together, these results presented here clearly demonstrate that two overlapping peptides, CDCA1 (39-64) and CDCA1 (55-78), have capability to stimulate HLA-DR4, HLA-DR9, HLA-DR15 and HLA-DP2-restricted Th cells, suggesting that these peptides can be presented to Th cells by promiscuous HLA class II molecules and would be available for cancer immunotherapy of many patients.

To confirm the capability of CDCA1 (39-64) and CDCA1 (55-78) to stimulate HLA-DR4, HLA-DR9, HLA-DR15 and HLA-DP2-restricted Th cells, the present investigators performed experiment using irrelevant peptide as a control for HLA class II molecule-restricted Th cell induction.

Figure 8A:
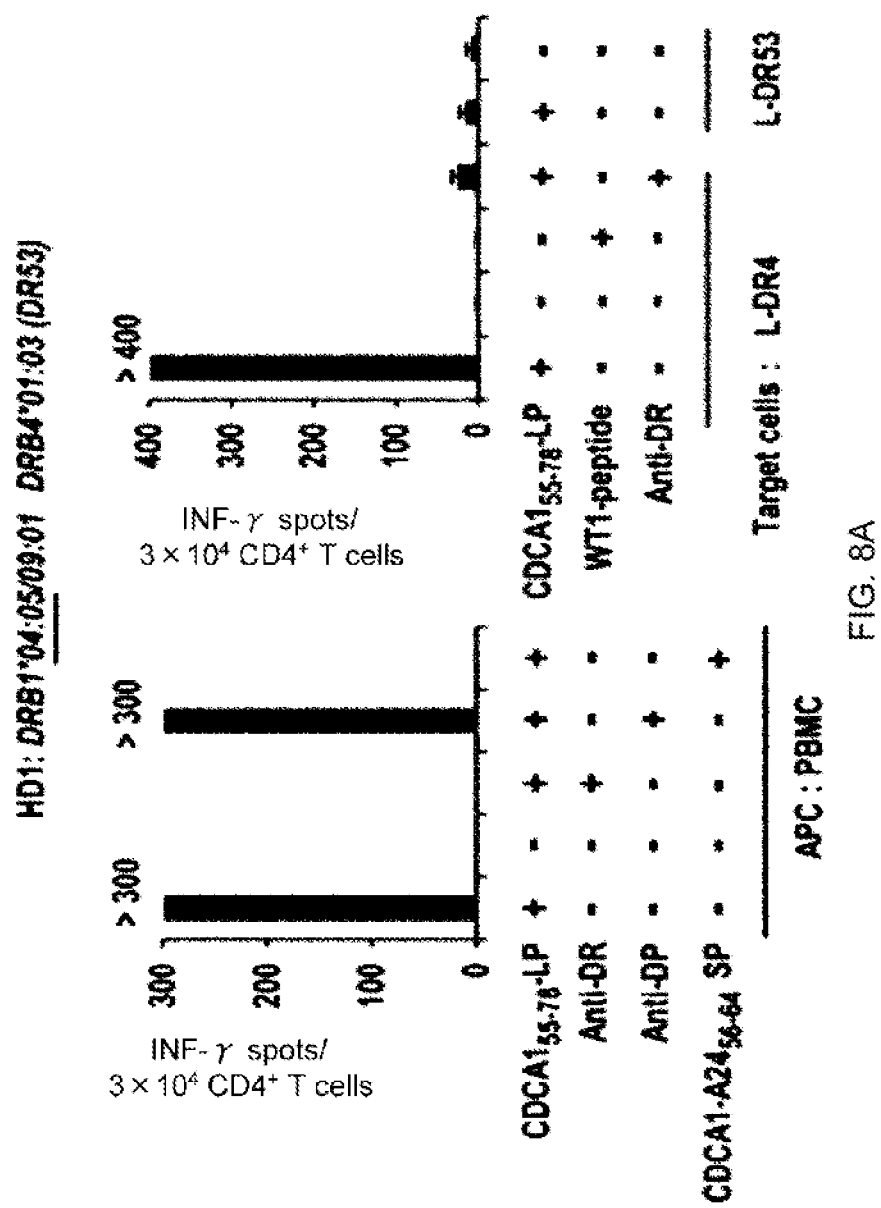
FIG. 8A.

CD4$^+$ T-cells isolated from PBMCs of healthy donors were stimulated at weekly intervals with autologous DCs and PBMCs pulsed with CDCA1 (55-78)-LP. After at least 3 rounds of stimulation, CDCA1 (55-78)-LP-specific responses of cultured CD4$^+$ T-cells were examined by IFN-gamma ELISPOT assays. In an HLA-DR4-positive healthy donor (HD1), the generated Th cells produced a significant amount of IFN-gamma in response to CDCA1 (55-78)-LP-pulsed PBMCs in an HLA-DR-dependent manner. The bulk Th cells specifically recognized L-DR4 cells pulsed with CDCA1 (55-78)-LP in an HLA-DR-dependent manner, but not irrelevant peptide-pulsed L-DR4 cells or CDCA1 (55-78)-LP-pulsed L-DR53 cells (FIG. 8A). The similar results were obtained from other two DR4$^+$ donors (Table 1; HD4 and HD5).

These results suggest that CDCA1 (55-78)-LP encompasses an HLA-DR4-restricted Th cell epitope.

Figure 8B:
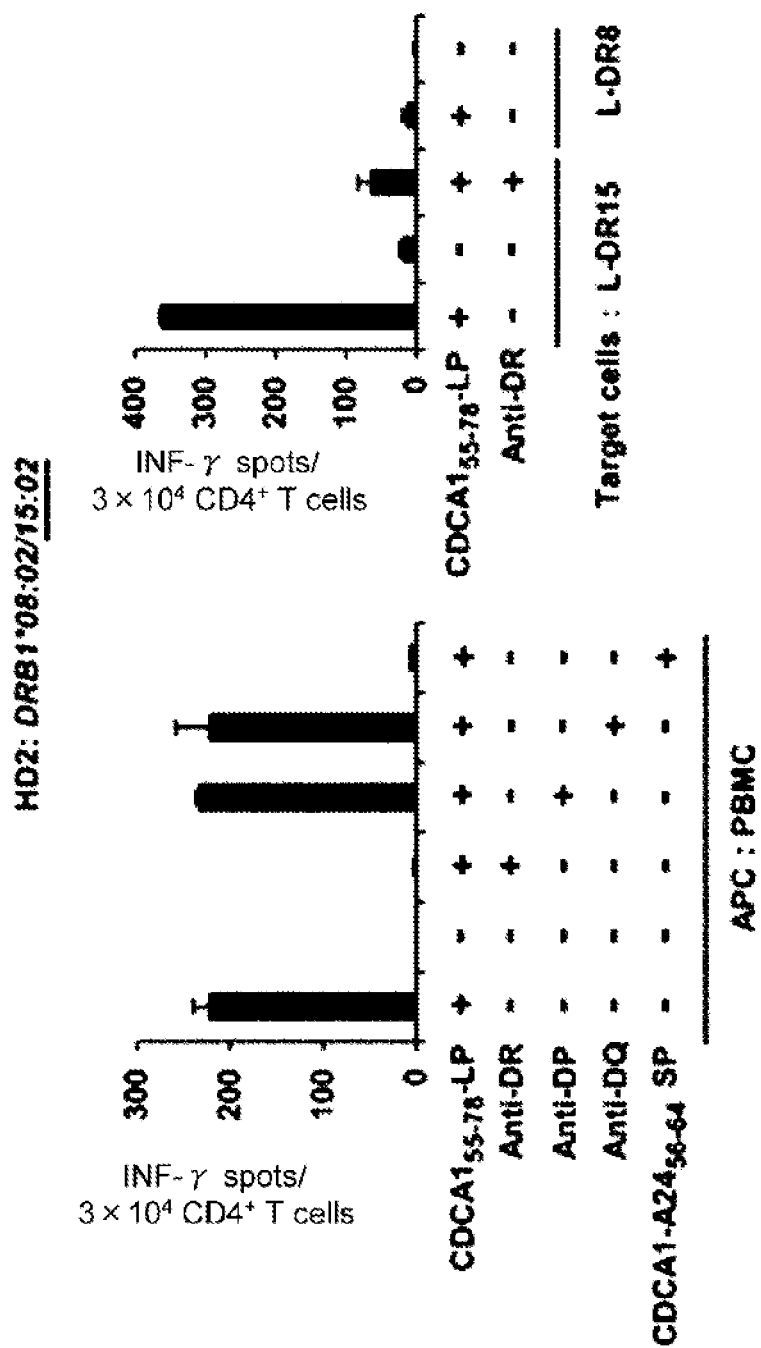
FIG. 8B.

To investigate whether CDCA1 (55-78)-LP induces responses in Th cells restricted by other HLA class II molecules, CD4$^+$ T-cells from HLA-DR4-negative healthy donors were tested. The inventors confirmed that CDCA1 (55-78)-LP generates HLA-DR15-restricted Th cells (FIG. 8B). CDCA1 (55-78)-LP also generates HLA-DP2-restricted Th cells (FIG. 8C). L-cells transduced with HLA-DP2 were unavailable; therefore, a CDCA1 (55-78)-LP-reactive Th cell clone (Th-clone) was established and used allogeneic PBMCs from 5 different donors as APCs to determine restriction by shared HLA-DP molecules. Thus, CDCA1 (55-78)-LP binds to HLA-DR4, HLA-DR15, and HLA-DP2, which suggest that CDCA1 (55-78)-LP encompasses Th cell epitopes presented by frequent HLA class II molecules in the Japanese/Pacific-Asian populations (Saito S et al., Tissue Antigens 2000; 56:522-9., Mack S J et al., Tissue Antigens 2000; 55:383-400).

Figure 8D:
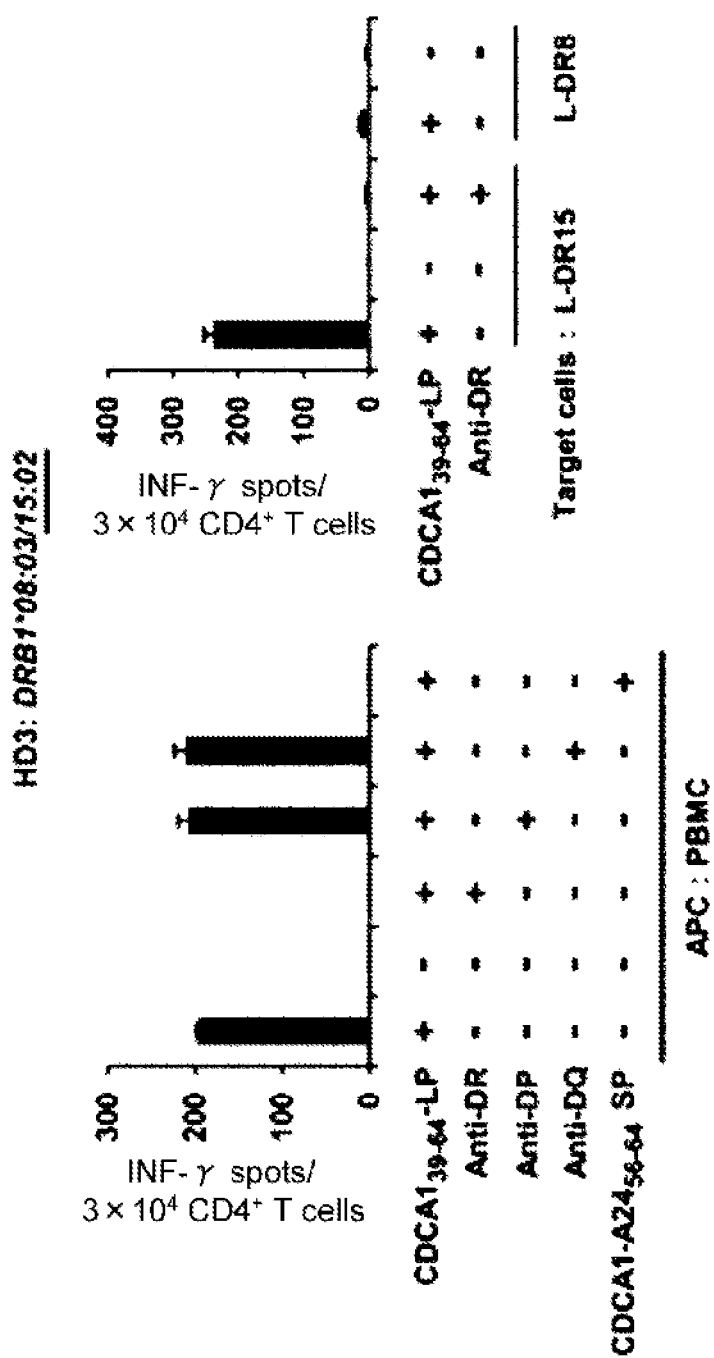
FIG. 8D.
Figure 8E:
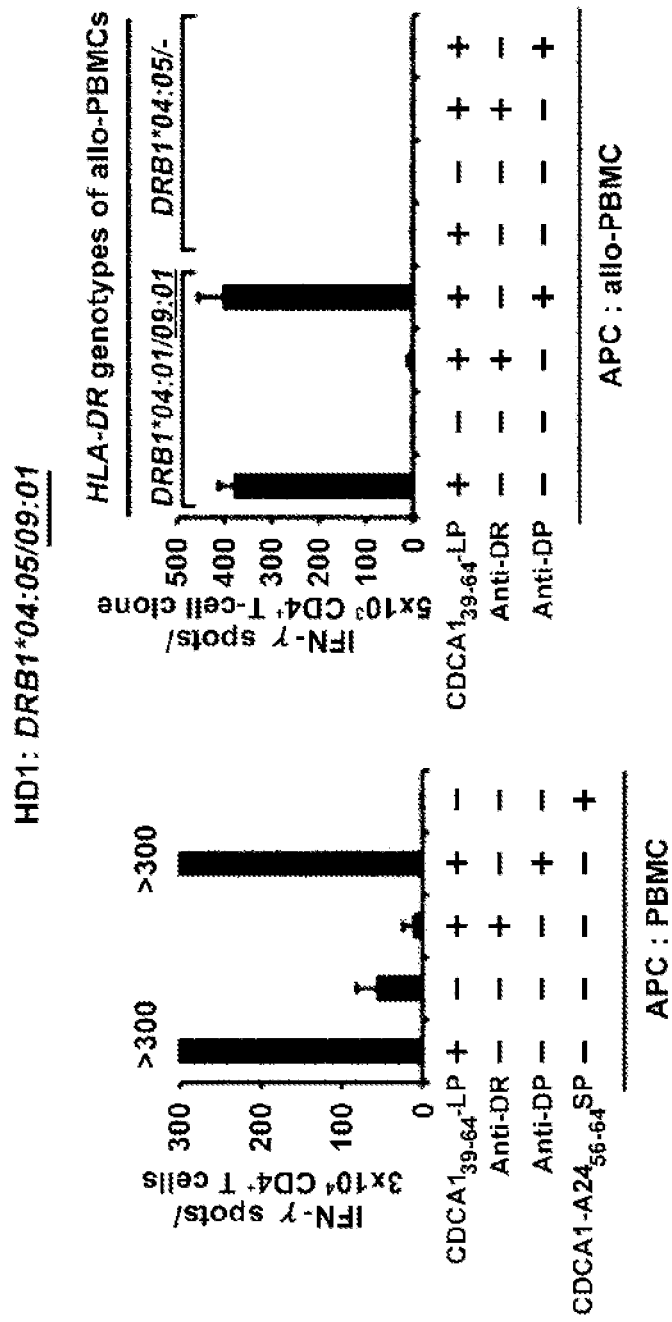
FIG. 8E.

Next, the inventors assessed and confirmed that CDCA1 (39-64)-LP can generate HLA-DR9 and HLA-DR15-restricted Th cells using the method described above (FIGS. 8D and E). Taken together, these results clearly demonstrate these overlapping-LPs can stimulate HLA-DR4, -DR9, -DR15, and -DP2-restricted Th cells. In this study, CDCA1-LP-specific Th cells generated from healthy donors did not respond to the CDCA1-A24 (56-64) SP embedded in CDCA1-LPs (FIG. 8A, B, D, E).

These results also showed that CDCA1 (39-64) and CDCA1 (55-78) have ability to induce HLA-DR4, HLA-DR9, HLA-DR15 and HLA-DP2-restricted Th cells.

CDCA1 (55-78) Peptide Stimulates Th1-Type CD4$^+$ T Cells.

To further characterize CDCA1 peptide-induced Th cells, the present inventors measured several cytokines in response to the stimulation of CDCA1 (55-78)-specific bulk CD4$^+$ Th cell line with cognate peptide by Bio-Plex system. CDCA1 (55-78)-specific bulk HTL line from the donors produced a large amount of IFN-gamma, GM-CSF, TNF-alpha and MIP-1beta, but less IL-4 and IL-7 by the restimulation with cognate peptide-pulsed L-DR0405 indicating Th1 polarized characteristics (FIG. 4A-D). Interestingly, the cytotoxicity marker CD107a could also be detected on CDCA1 (55-78)-specific bulk Th cell line stimulated with cognate peptide (FIG. 4E-H). Thus, CDCA1 (55-78) peptide-specific Th1 cells were dominantly activated in this culture condition.

CDCA1 (55-78) and CDCA1 (39-64) are Naturally Processed Epitopes.

The present inventors proceeded to assess whether autologous DC would be able to take up and process the CDCA1 protein to stimulate CDCA1-peptide-specific Th1 cell clones. The CDCA1 (55-78) LP-loaded mature DCs were prepared and used as APCs in IFN-gamma ELISPOT assays. As shown in FIG. 5A, an HLA-DR4-restricted CDCA1 (55-78)-reactive Th cell clone efficiently recognized DC loaded with CDCA1 protein and specifically produced IFN-gamma, but did not recognize control protein-loaded DC or protein-unloaded DC. In addition, the capacity of this Th cell clone to recognize naturally processed CDCA1 antigen presented by DC was effectively blocked by anti-HLA-DR antibodies, but not by control anti-HLA-class I antibodies confirming that the epitope was presented via HLA-DR4 molecules. A similar analysis was performed using an HLA-DP2-restricted and CDCA1 (55-78)-reactive Th cell clone. This Th cell clone efficiently recognized CDCA1 protein-loaded DC and produced IFN-gamma, but did not recognize control protein-loaded DC, suggesting that the HLA-DP2-restricted Th cell epitope was also naturally processed from CDCA1 protein in DC (FIG. 5B).

The HLA-DR9-restricted CDCA1 (39-64)-reactive Th cell clone responded to CDCA1 protein-loaded DC, but not control protein-loaded DC. In addition, this response of Th cell was effectively blocked by anti-HLA-DR antibodies, but not by control anti-HLA-class I antibodies confirming that the epitope was presented via HLA-DR9 molecules.

In summary, the overall results indicate that the Th cell epitopes, CDCA1 (55-78) and CDCA1 (39-64) are naturally processed by DC from CDCA1-protein and presented by HLA-class II molecules on the cell surface of DC.

The CDCA1 (55-78) LP induces an efficient cross-priming of naive CDCA1-A2 (65-73) SP-specific CD8$^+$ T cells in vitro and in vivo.

Figure 6A:
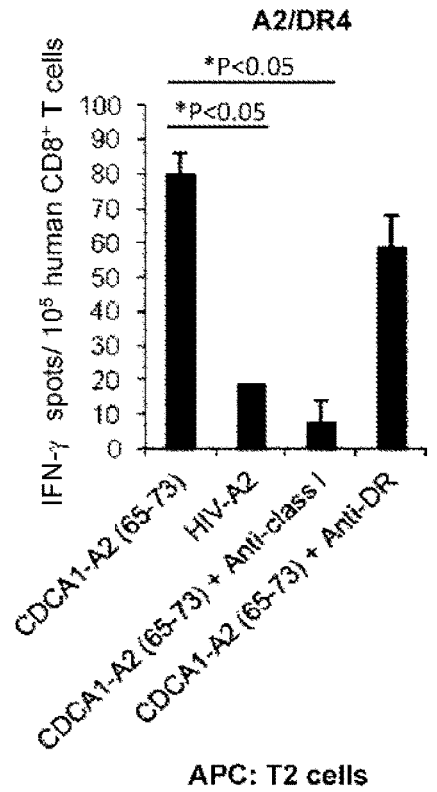
FIGS. 6A-6B.

The present inventors assessed whether the CDCA1 (55-78) LP could induce CDCA1-A2 (65-73) SP-specific CTLs by cross-presentation of the LP by DC in vitro. To confirm this, the inventors attempted to generate CDCA1-A2 (65-73) SP-specific CTLs from peripheral blood CD8$^+$ T cells derived from two HLA-A2-positive donors by stimulation with the CDCA1 (55-78) LP-loaded DC. After three times stimulations with the LP-loaded DC, the frequency of CD8$^+$ T cells specific to the CDCA1-A2 (65-73) SP in the resulting CTL lines was examined by IFN-gamma ELISPOT assay. As shown in FIG. 6A, the CTLs generated by stimulation with the CDCA1 (55-78) LP-loaded DC specifically produced IFN-gamma in response to re-stimulation with T2 cells pulsed with the CDCA1-A2 (65-73) SP, but not with T2 cells pulsed with the irrelevant peptide. The IFN-gamma production was significantly inhibited by addition of anti-HLA-class I mAb, but not the anti-HLA-DR mAb, thus indicating that the present inventors successfully stimulated CDCA1-A2 (65-73) SP-specific CD8$^+$ T cells through the cross-presentation of LP by DC in vitro.

Figure 6B:
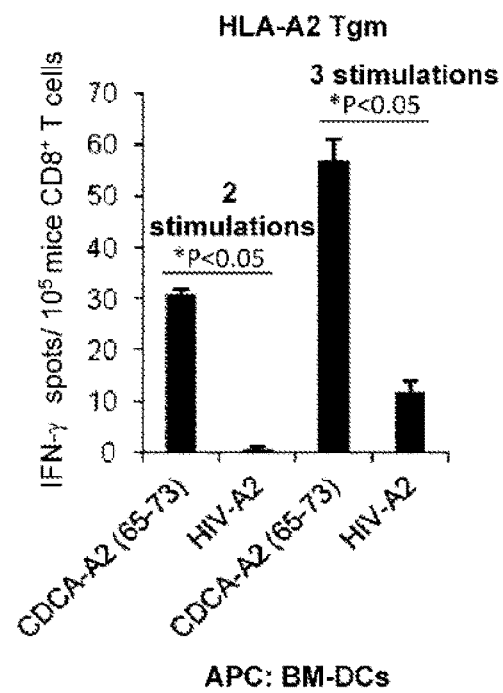

Next, the capacity of the CDCA1 (55-78) LP to stimulate CDCA1-A2 (65-73) SP-specific cells was examined in vivo. HLA-A2 Tgm were immunized twice or three times at the base of the tail with CDCA1 (55-78) LP emulsified in IFA at 7-day intervals. Seven days after the second or third vaccinations with CDCA1 (55-78) LP, the number of IFN-gamma-secreting CD8+ T cells in inguinal LN was determined by an ex vivo ELISPOT assay. As shown in FIG. 6B, the CTLs generated by twice immunizations of HLA-A2 Tgm with CDCA1 (55-78) LP produced IFN-gamma specifically in response to re-stimulation with BM-DC pulsed with the CDCA1-A2 (65-73) SP, but not with BM-DC pulsed with the irrelevant HIV-A2 peptide. In addition, the number of specifically IFN-gamma producing T cells was increased after the third vaccinations.

Taken together, these results indicated that CDCA1 (55-78) LP induced a significant proportion of IFN-gamma-producing CDCA1-A2 (65-73) SP-specific CTL after cross-presentation by both human DC in vitro and BM-DC in vivo in HLA-A2 Tgm.

Figure 7A:
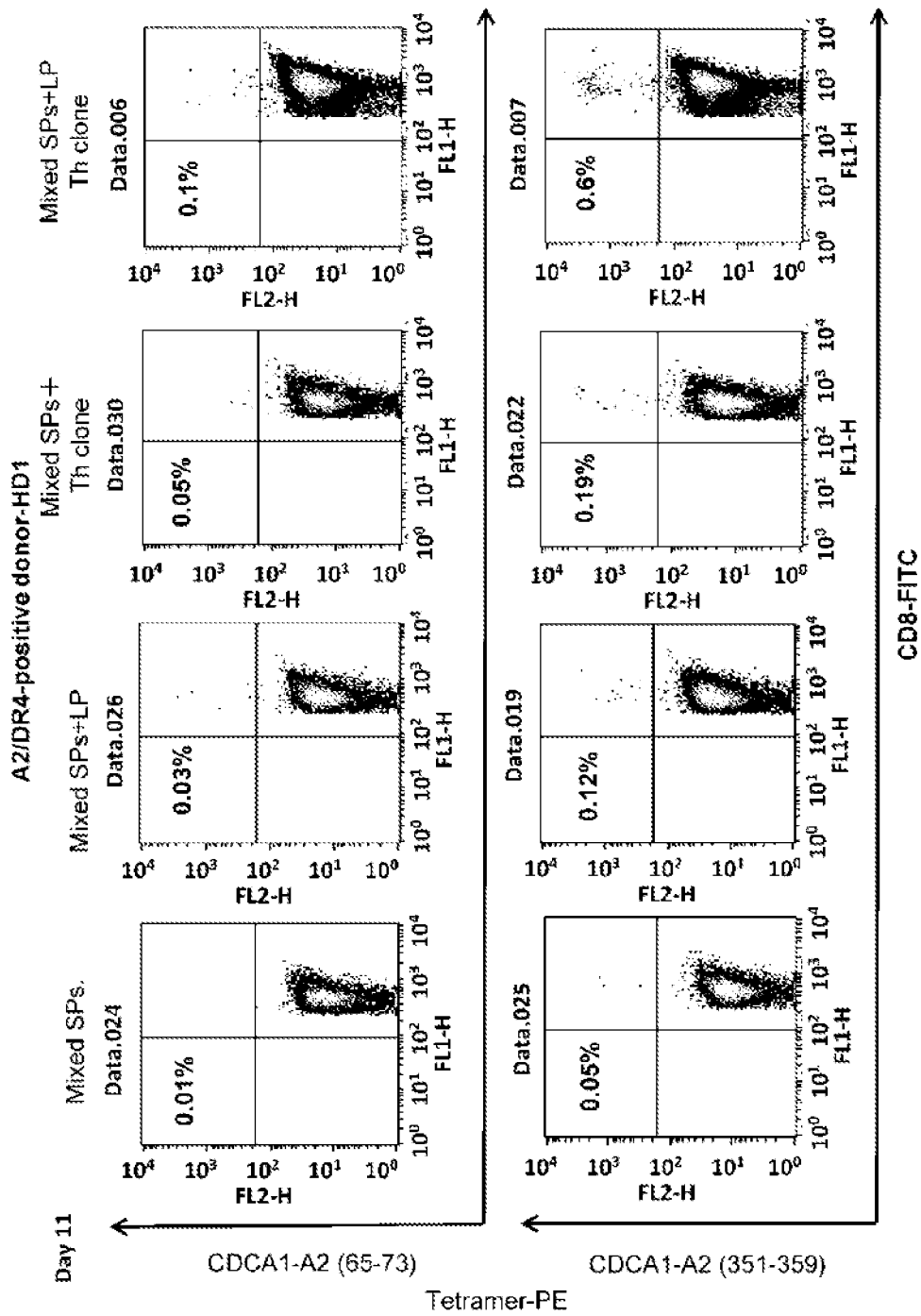
FIG. 7A presents the enhancement of induction of CDCA1-A2 (65-73), CDCA1-A2 (351-359) or CDCA1-A24 (56-64)-specific CTLs by stimulation with the CDCA1 (55-78) LP and CDCA1 (55-78) LP-specific CD4+ Th cell clones.
Figure 7B:
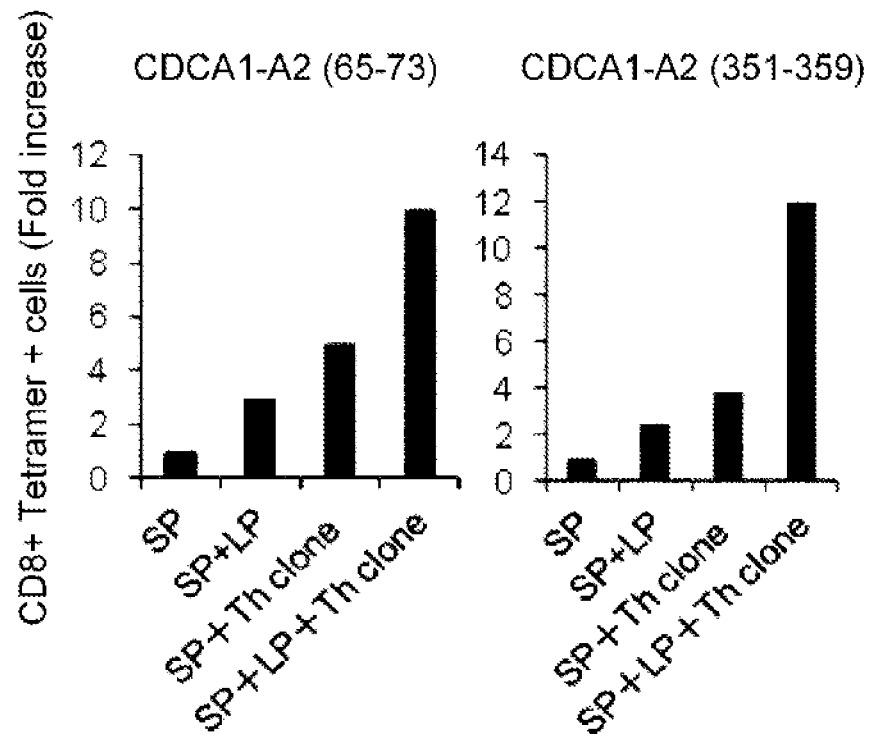
FIG. 7B.

Enhancement of Induction of CDCA1-Specific and HLA-Restricted CTLs by CDCA1 (55-78) LP Next, the present inventors tested whether the CDCA1 (55-78) LP could enhance the induction of CDCA1-specific and HLA-A2-restricted CTLs. When the PBMCs from an HLA-A2-positive and DR4-positive donor were stimulated with a mixture of CDCA1-A2 (65-73) SP and CDCA1-A2 (351-359) SP alone, the frequencies of these two SPs-specific tetramer+ cells were 0.01% and 0.05% of CD8+ T cells respectively (FIG. 7A). When the PBMCs were co-stimulated with both SPs and CDCA1 (55-78) LP, the frequencies of these SPs-specific tetramer-positive cells increased to 0.03% and 0.12% respectively (3-folds and 2.4-folds increase respectively in the frequencies compared with those stimulated with SPs alone) (FIGS. 7A and B). The absolute numbers of tetramer+ cells were also significantly increased by only adding CDCA1 (55-78) compared with those stimulated with SPs alone (data not shown). When the PBMCs were co-stimulated with both of these two SPs and CDCA1 (55-78)-specific Th clone, the frequencies of SPs-specific tetramer+ cells increased to 0.05% and 0.19% respectively (5-folds and 3.8-folds increase respectively). Furthermore, when the PBMCs were co-stimulated with SPs, CDCA1 (55-78) and CDCA1 (55-78)-specific Th clone, the frequencies of SPs-specific tetramer+ cells significantly increased to 0.1% and 0.6% respectively (10-folds and 12-folds increase respectively). As for tetramer+ cell frequencies, addition of CDCA1 (55-78) helper peptide or Th clone into the culture induced slight increase in the frequencies, respectively, whereas addition of both of them (CDCA1 (55-78)+Th clone) remarkable increased the frequencies of specific CTLs. These results were reproducibly observed when the present inventors used a different CDCA1 (55-78)-specific Th clone (data not shown).

Figure 7C:
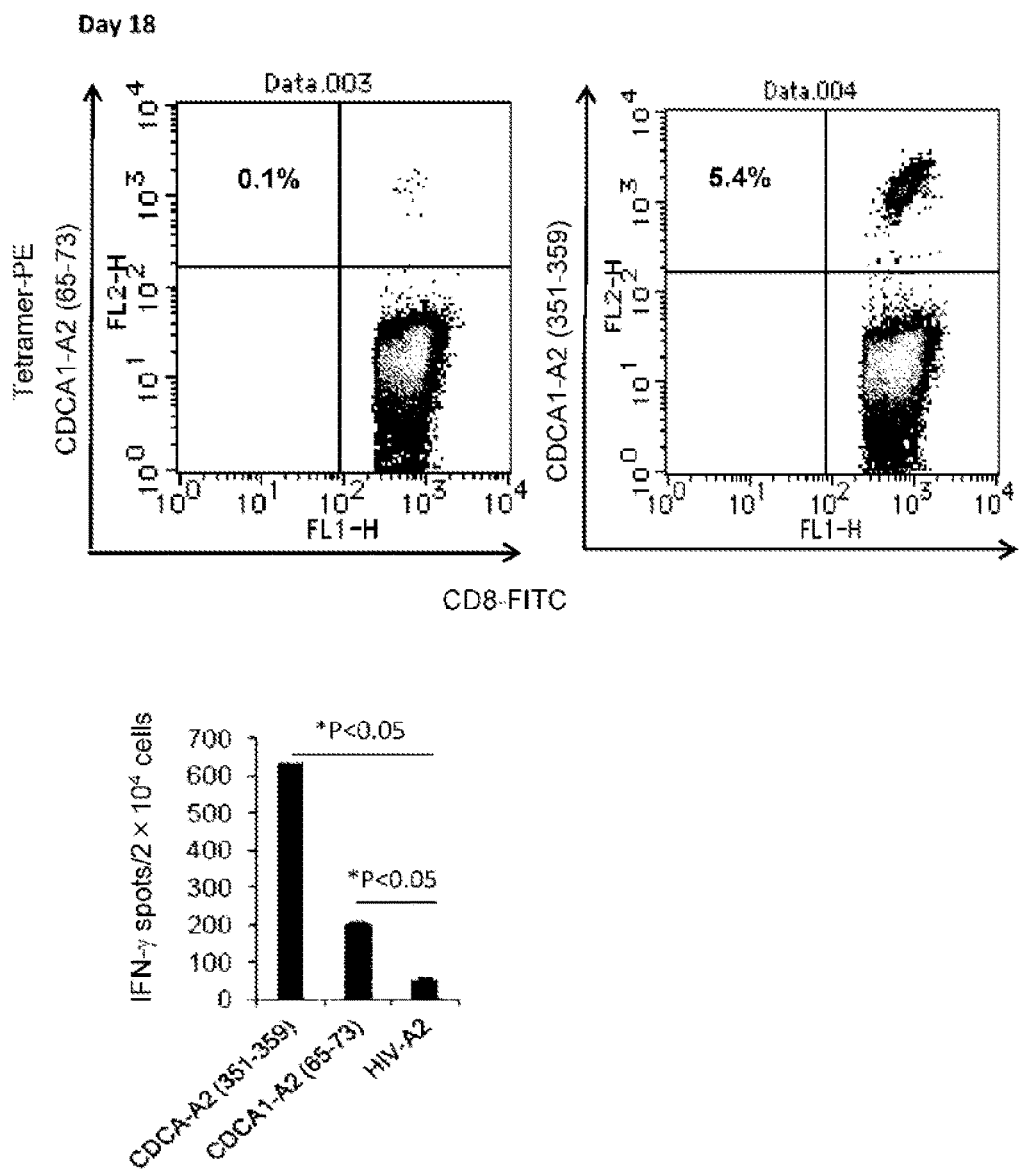
FIG. 7C.
Figure 7D:
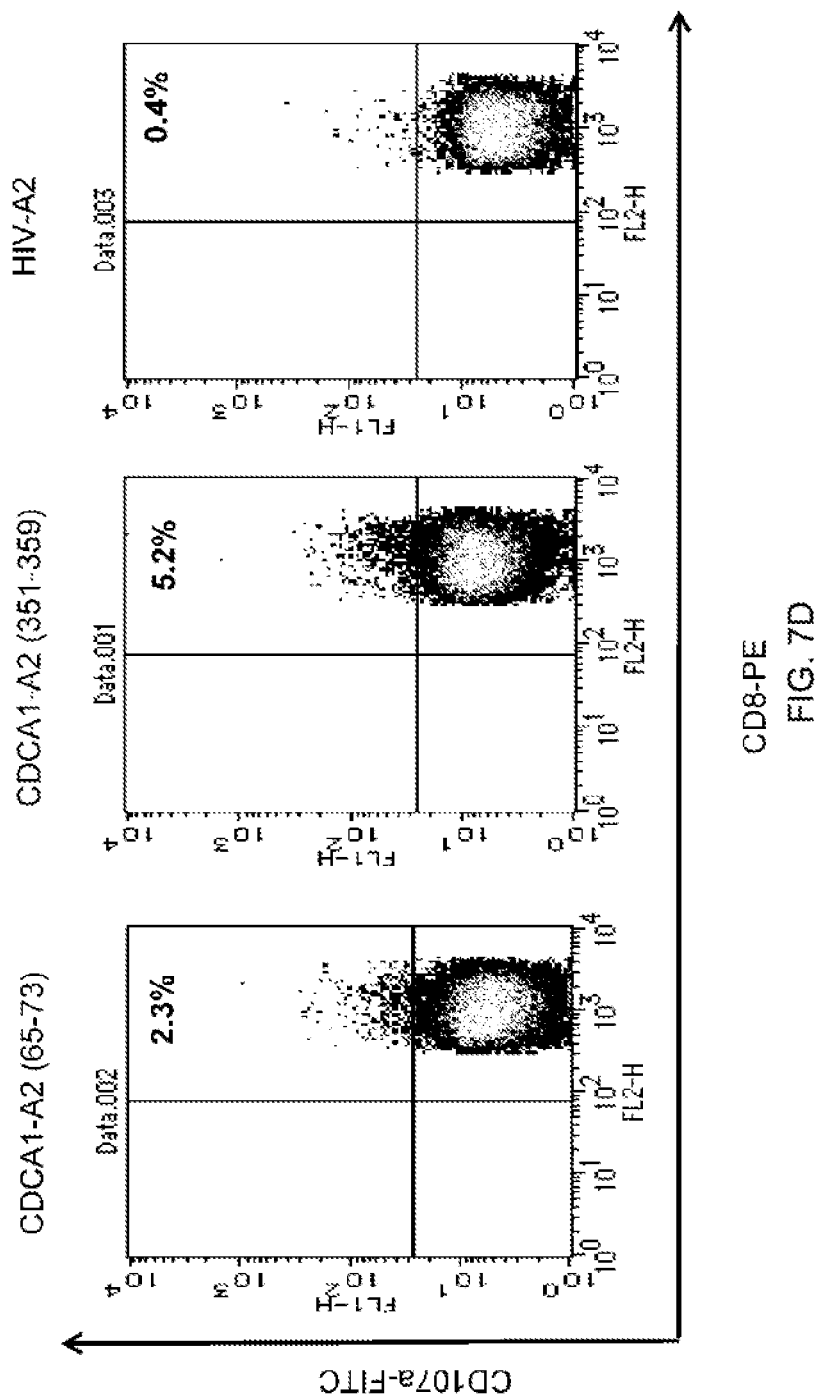
FIG. 7D.

The successfully induced CDCA1-specific CTL line by stimulation with the mixture of SPs, CDCA1 (55-78) LP and CDCA1 (55-78)-specific Th clone was restimulated with SPs and CDCA1 (55-78) LP (third stimulation) on day 14, and CDCA1-specific and HLA-A2-restricted CTLs were expanded. The frequencies of tetramer+ cells significantly increased to 0.1% and 5.4% respectively, especially in CDCA1-A2 (351-359)-specific tetramer+ cells (FIG. 7C, D). Importantly, both peptide-specific IFN-gamma production and the cytotoxicity marker CD107a could be detected on this CDCA1-specific CTL line stimulated with cognate peptides (FIG. 7C, D).

These results clearly demonstrate that CD4+ T cells activated by the stimulation with CDCA1 (55-78) Th cell epitope peptide in the culture or a CDCA1 (55-78)-specific Th clone could enhance the induction of both CDCA1-A2 (65-73) SP and CDCA1-A2 (351-359) SP-specific CTLs, and that the enhancement was at maximum in the presence of both CDCA1 (55-78) LP and Th cell clone.

Figure 7E:
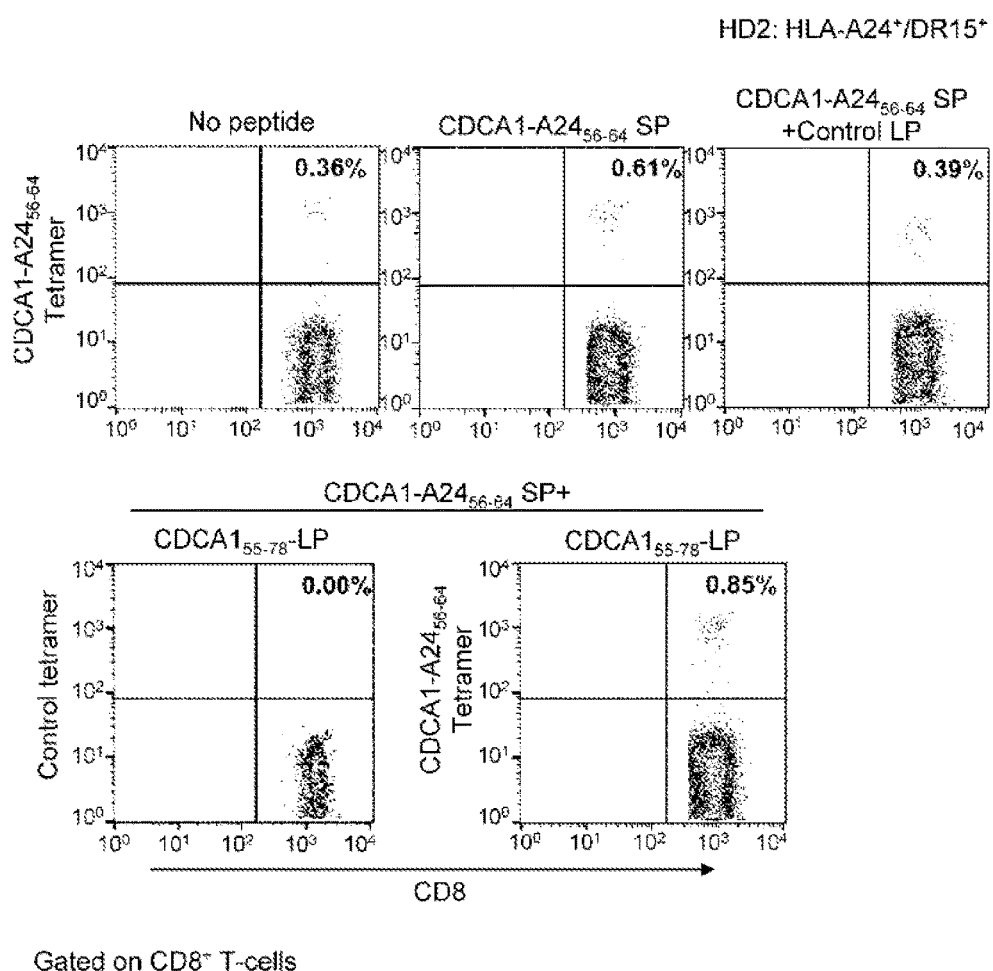
FIG. 7E.
Figure 7E:
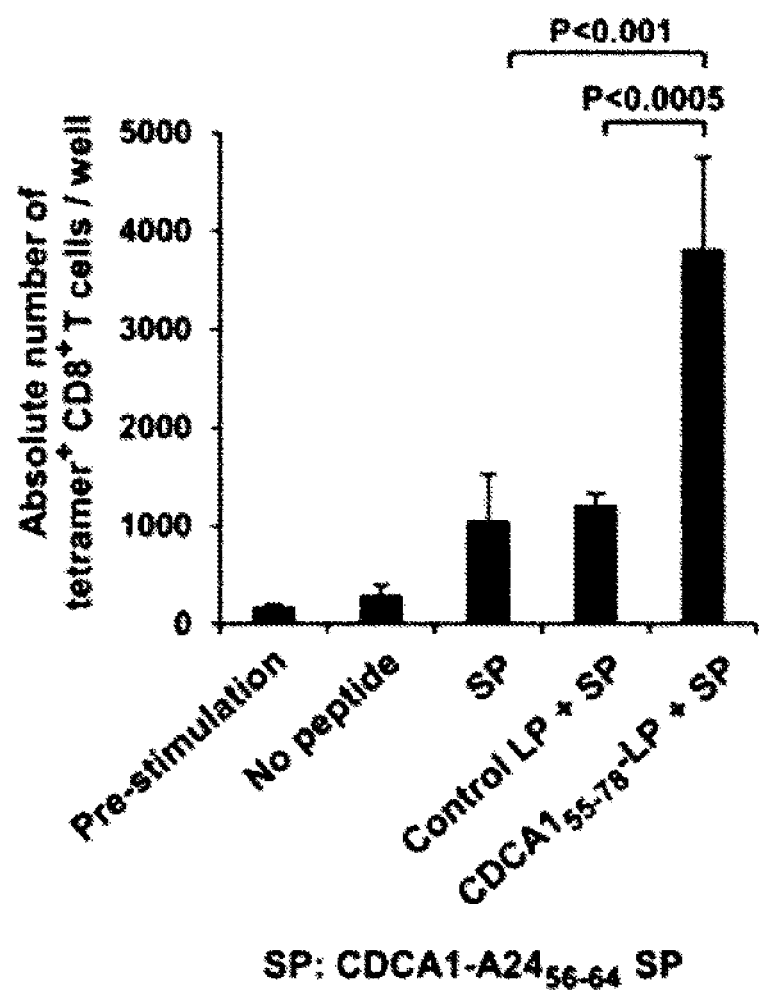

The synergistic effect on induction of CDCA1-A24-specific CTLs were also tested in HLA-A24+/DR15+ HD2 using CDCA1-A24 (56-64)-specific tetramer. CDCA1 (55-78)-LP-specific bulk CD4+ T-cells and CDCA1-A24 (56-64) SP-specific bulk CD8+ T-cells were cultured with autologous DCs in the presence of CDCA1-A24 (56-64) SP alone (SP), CDCA1-A24 (56-64) SP+Control LP (Control LP+SP), or CDCA1-A24 (56-64) SP+CDCA1 (55-78)-LP (CDCA1 (55-78)-LP+SP) without any cytokine. After 1-week in vitro culture with peptides, the cultured cells were stained with tetramer of the HLA-A24 (A*24:02)/CDCA1-A24 (56-64) complex and anti-human CD8 mAb as described in the Materials and Methods section. As shown FIG. 7E, the addition of CDCA1-A24 (56-64) SP+CDCA1 (55-78)-LP (CDCA1 (55-78)-LP+SP) significantly increased the absolute number of CDCA1-A24 (56-64) SP-specific CD8+ T-cells compared with the addition of SP alone or Control LP+SP. These results suggest that activated CDCA1-specific Th cells may be able to enhance induction of CDCA1-A24-specific CTLs.

Taken together, these results clearly demonstrated that CDCA1 (55-78) LP and activated CDCA1-specific CD4+ Tcells by stimulation with CDCA1 (55-78) LP can enhance an induction of CDCA-1 specific and HLA-restricted CTL individually or cooperatively.

CDCA1-LPs Induce Efficient Expansion of CDCA1-A24 (56-64) SP-Specific CTLs.

Figure 9A:
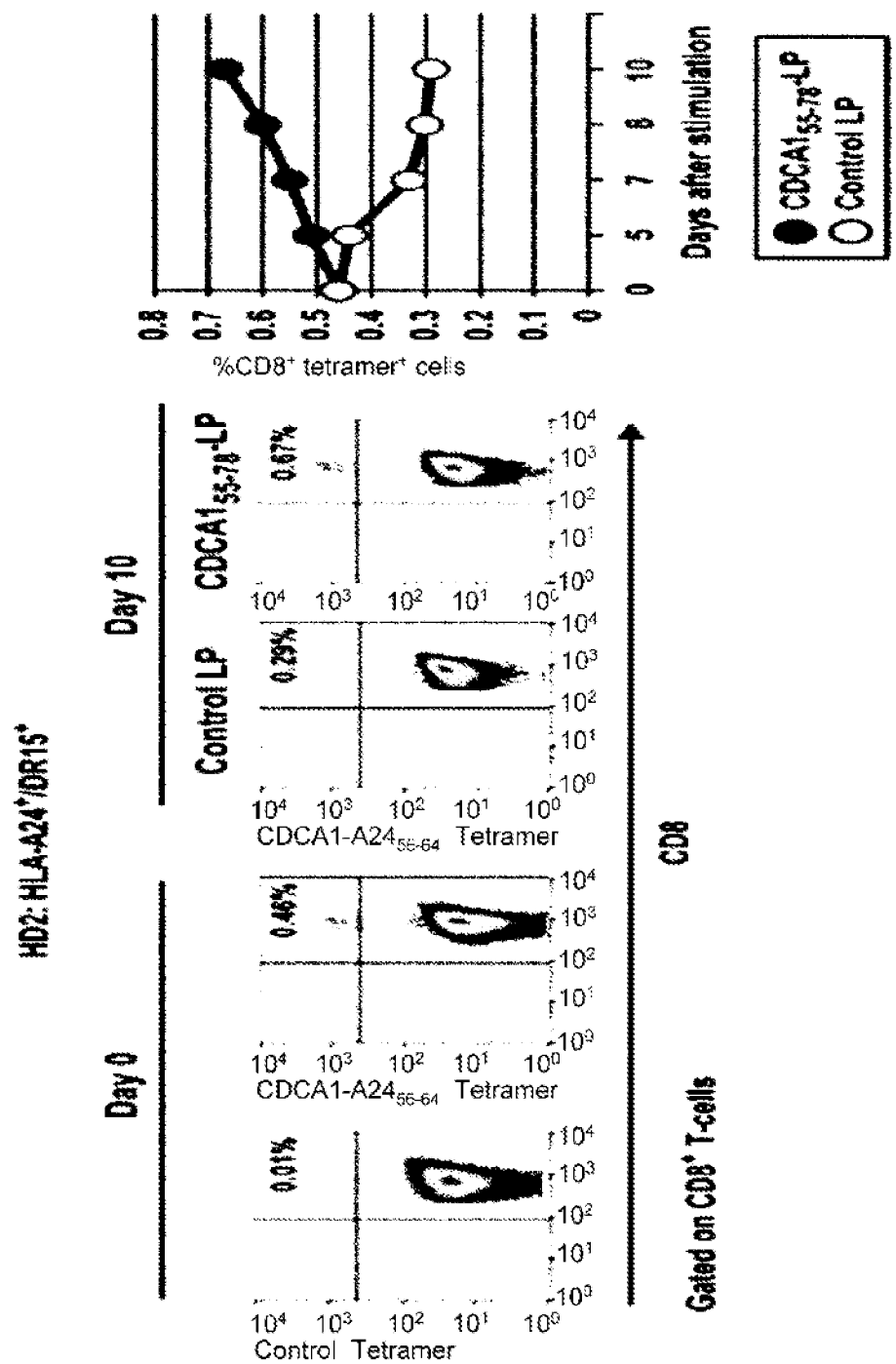
FIG. 9A.
Figure 9B:
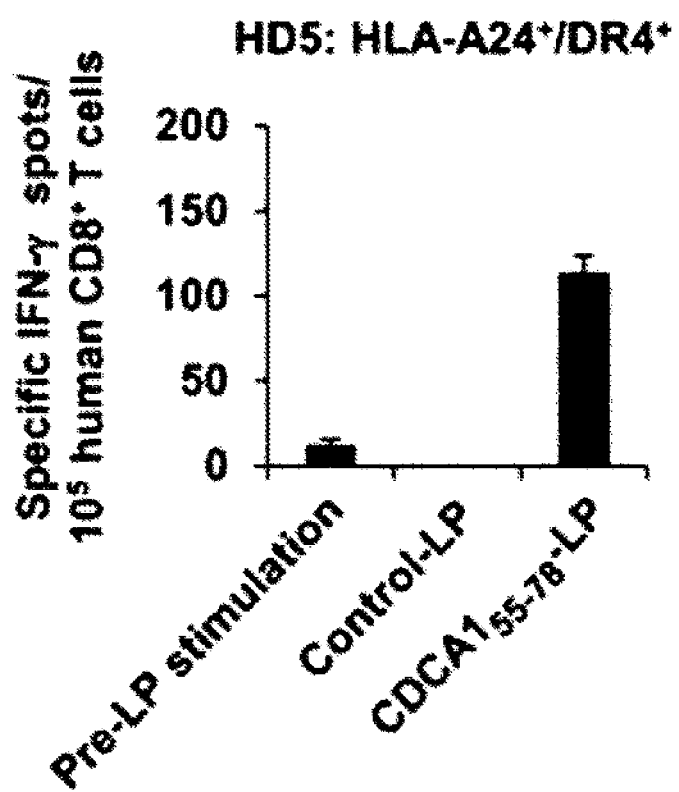
FIG. 9B.

Next, a possibility that the CDCA1-LPs can induce expansion of CDCA1-specific bulk CTLs was assessed. CDCA1-A24 (56-64) SP-specific bulk CTLs generated from purified CD8+ T-cells of HD2 (HLA-A24+/DR15+) were cultured for 1 week with CDCA1 (55-78) LP-pulsed autologous DCs. As shown in FIG. 9A, the population of CDCA1-A24 (56-64)-tetramer+ CD8+ cells was expanded by stimulation with CDCA1 (55-78) LP-pulsed DCs, but decreased when bulk CTLs were stimulated with control-LP-pulsed DCs. A similar result was obtained from HLA-A24+/DR4+ HD5 in IFN-gamma ELISPOT assay (FIG. 9B). Detailed method of this experiment is provided in Materials and Methods.

Figure 9C:
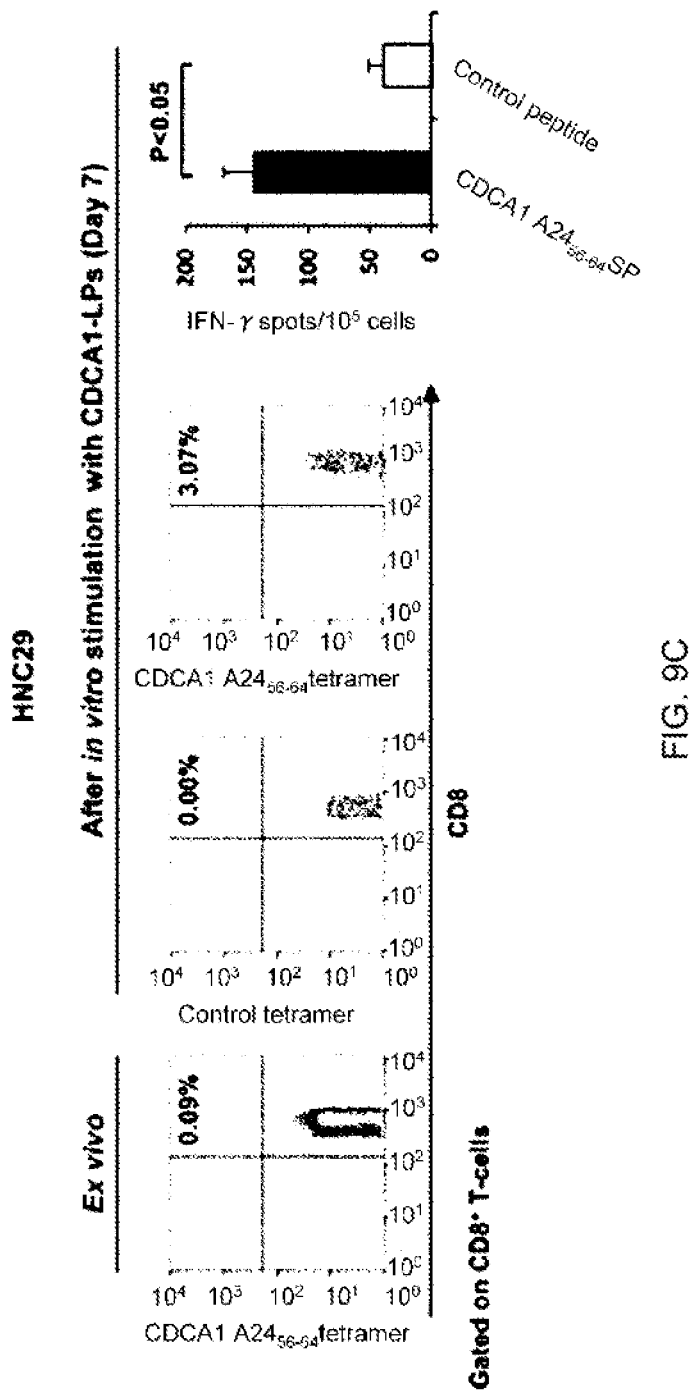
FIG. 9C.
Figure 9D:
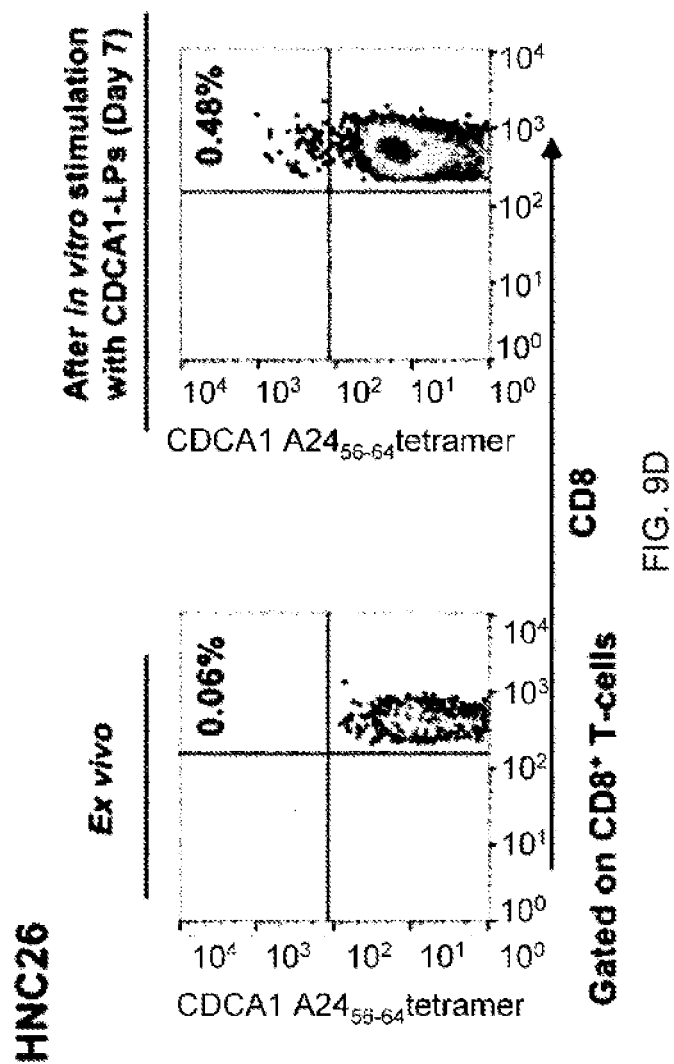
FIGS. 9D-9G.
Figure 9E:
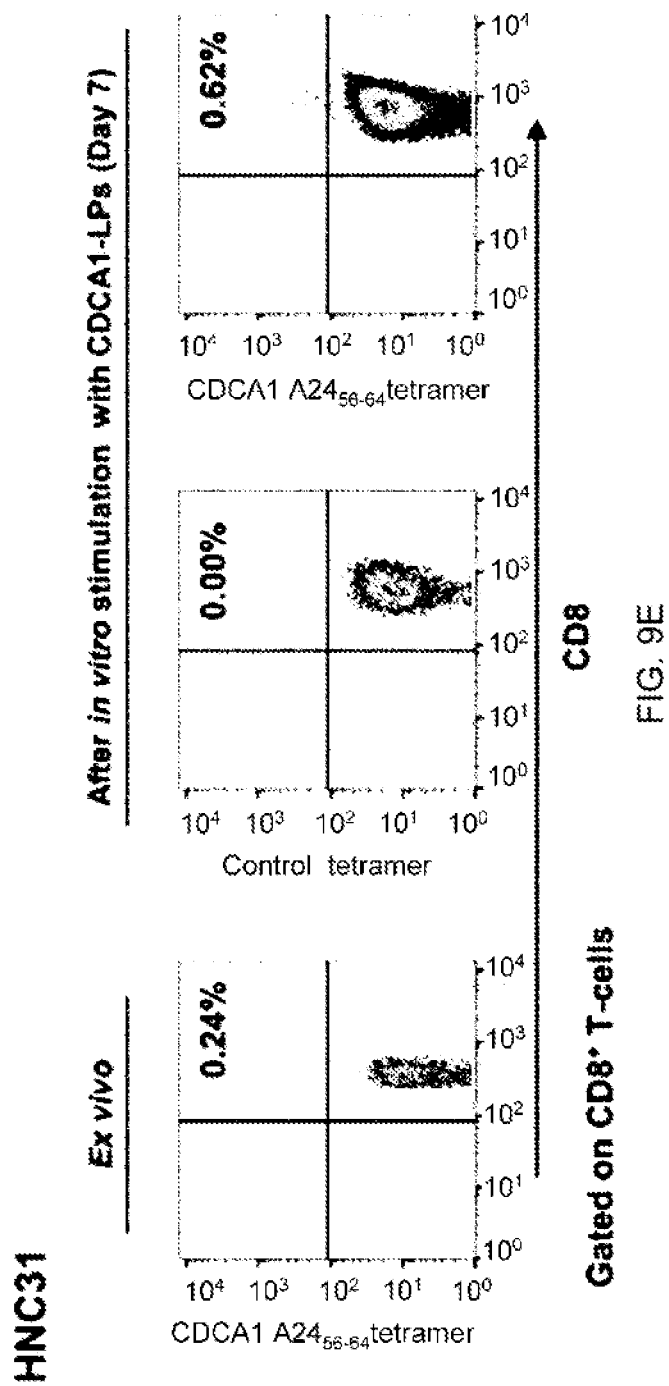
Figure 9F:
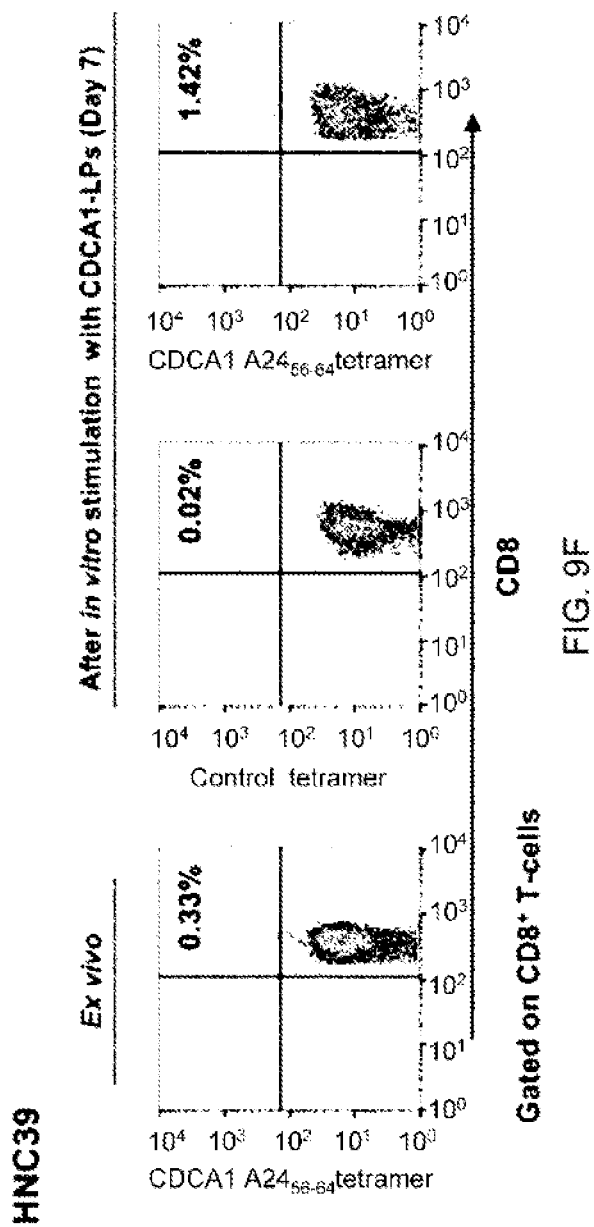
Figure 9G:
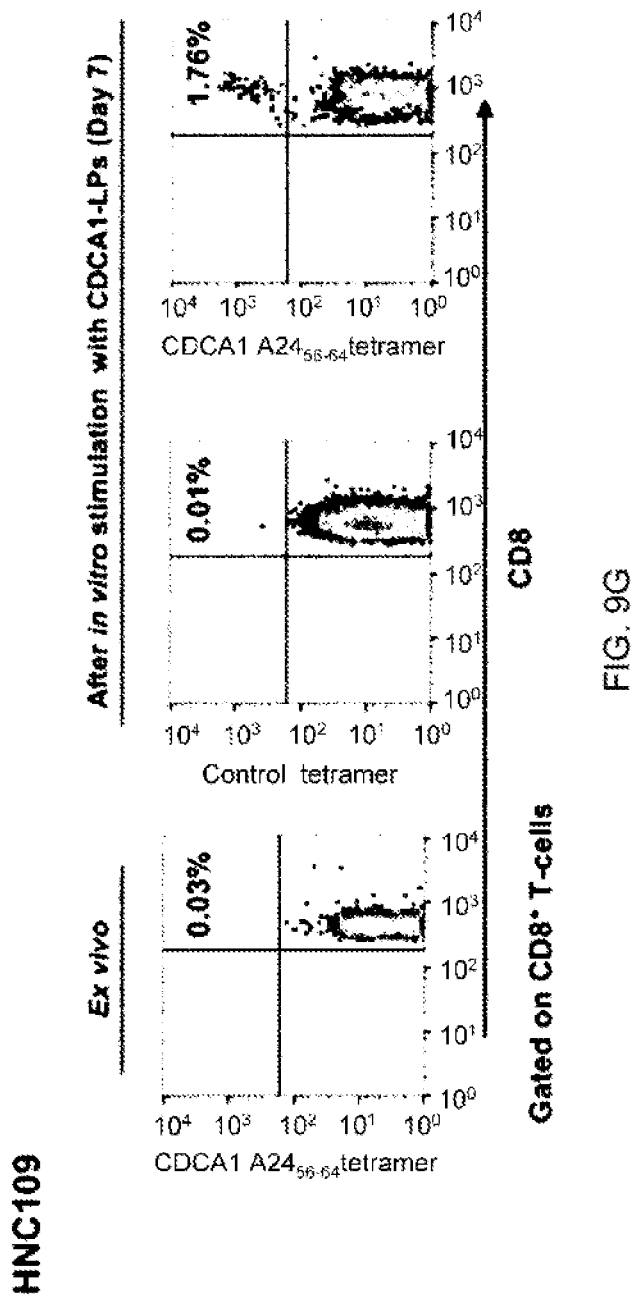

The present inventors also tested whether CDCA1-LPs could induce in vitro expansion of CDCA1-A24 (56-64) SP-specific CTLs in the PBMCs of HNC patients vaccinated with CDCA1-A24 (56-64) SP. PBMCs from vaccinated HNC patients were cultured with a mixture of CDCA1 (55-78) LP and CDCA1 (39-64) LP. When fresh PBMCs isolated from HNC29 were stained with a CDCA1-A24 (56-64)-specific tetramer before in vitro culture (ex vivo), the frequency of tetramer+ cells was only 0.09% of CD8+ T-cells. Interestingly, tetramer+ CD8+ T-cell in PBMCs from HNC29 were significantly expanded by 1-week in vitro stimulation of PBMCs with a mixture of CDCA1 (55-78) LP and CDCA1 (39-64) LP. The frequency of CDCA1-A24 (56-64) SP-specific CTLs increased to 3.07% of CD8+ T-cells (FIG. 9C; Day 7). CDCA1-A24 (56-64) SP-specific IFN-gamma production of T-cells was also detected when the cultured cells were stimulated with CDCA1-A24 (56-64) SP (FIG. 9C; bar graph, Day 7). The similar results were also obtained in HNC26, 31, 39, and 109 (FIG. 9D-G). These results suggest expansion of CDCA1-A24 (56-64) SP-specific CTLs might be induced by cross-presentation of CDCA1-LPs by DCs.

Figure 10A:
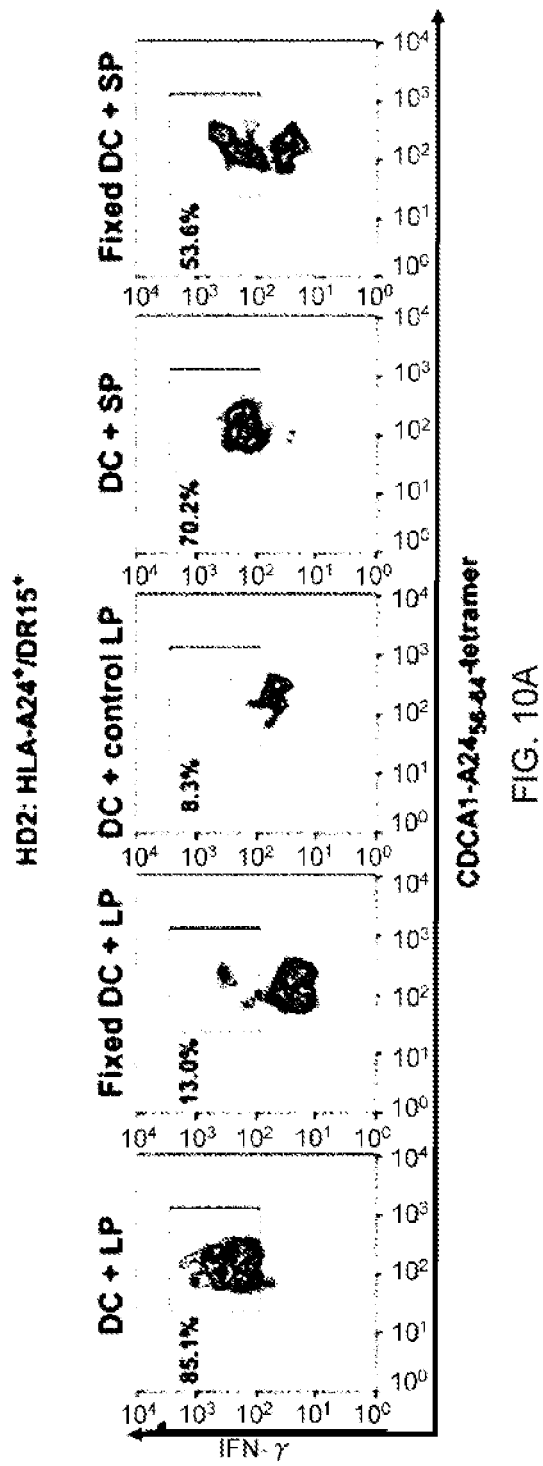
FIG. 10A.
Figure 10B:
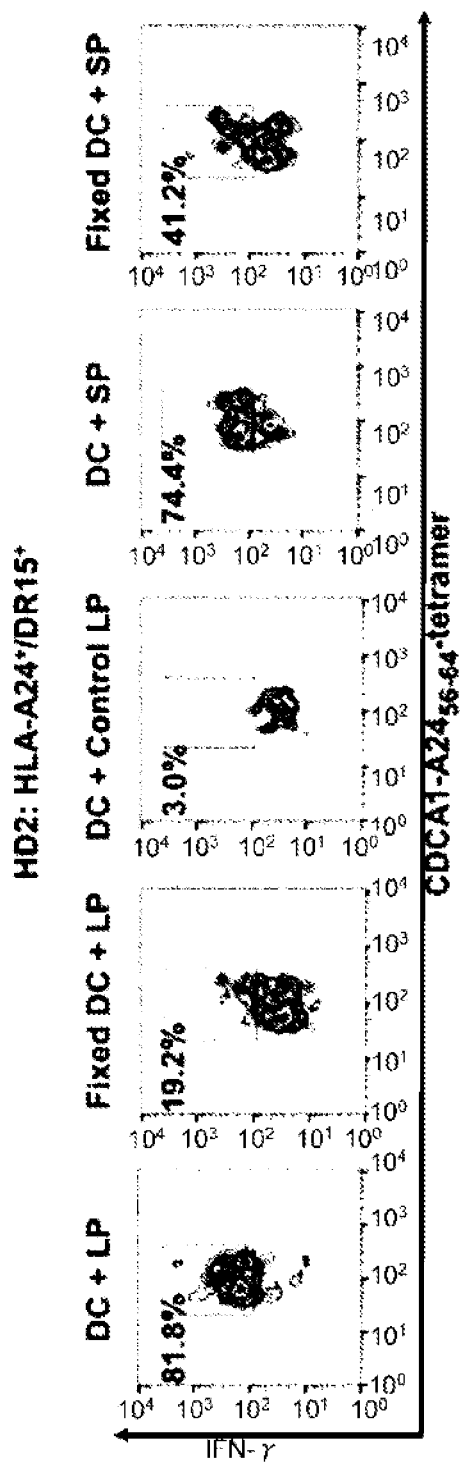
FIG. 10B.

Cross-Presentation of CDCA1-LPs Efficiently Primes CDCA1-Specific CD8+ T-Cells In Vitro and In Vivo The cross-presentation of CDCA1-LPs by DCs was evaluated in the context of the IFN-gamma response of CDCA1-A24 (56-64)-specific tetramer+CD8+ T-cells. Fixed DCs, unable to cross present but able to present CDCA1-A24 (56-64) SP as efficiently as live DCs (FIG. 10A, Fixed DC+SP), were used to exclude or evaluate the contribution of exogenous presentation of LP degradation products in the T-cell response. CDCA1 (55-78) LP (FIG. 10A) and CDCA1 (39-64) LP (FIG. 10B) induced a significant proportion of IFN-gamma secreting tetramer+ CD8+ T-cells only when they were cross presented by unfixed DCs (DC+LP). CDCA1-LP-pulsed fixed DCs could not stimulate CDCA1-A24 (56-64)-specific CTLs, similar to irrelevant LP-pulsed unfixed DCs (Fixed DC+LP and DC+irrelevant LP).

To investigate the cross-priming of CDCA1-specific CTLs, the inventors examined whether CDCA1 (55-78) LP could prime CDCA1-A24-specific CTLs. CDCA1-LP-pulsed fixed DCs could not stimulate CDCA1-A24 (56-64)-specific CTLs, similar to irrelevant LP-pulsed unfixed DCs (Fixed DC+LP and DC+irrelevant LP). CDCA1 (55-78)-LP-loaded DCs also could prime CDCA1-A24 (56-64) SP-specific CTLs and CDCA1-A2 (65-73) SP-specific CTLs in an HLA-A24+/A2+/DR4+ donor (HD5; FIG. 6C)

Figure 6E:
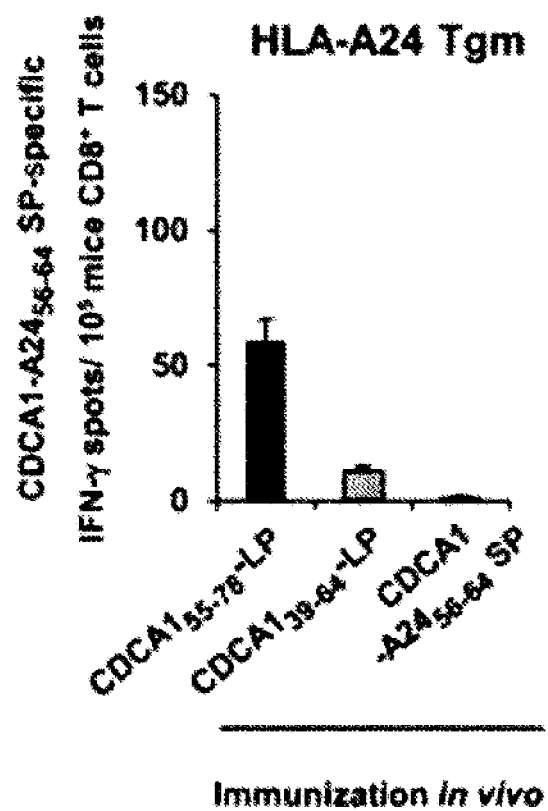
FIG. 6E.

The CD8+ T-cells of HLA-A24 Tgm vaccinated with CDCA1 (55-78) LP also produced IFN-gamma specifically in response to stimulation with BM-DCs and C1R-A2402 cells pulsed with the CDCA1-A24 (56-64) SP (FIG. 6D, left panel). A similar result was obtained when HLA-A24 Tgm were vaccinated with CDCA1 (39-64) LP (FIG. 6D, right panel). HLA-A24 Tgm were immunized with twice the amount of CDCA1-LPs, because the number of CDCA1-A24 (56-64) SP-specific spots of HLA-A24 Tgm was lower than that of HLA-A2 Tgm. Furthermore, vaccination with CDCA1-LPs was superior to CDCA1-A24 (56-64) SP in induction of SP-specific CTLs (FIG. 6E). These results demonstrate that after uptake of CDCA1-LPs, APCs can cross-prime CDCA1-specific CTLs in vitro and in vivo.

Presence of CDCA1-Specific Th Cells in HNC Patients Vaccinated with CDCA1-A24 (56-64) SP In context of cancer immunotherapy, there is strong evidence suggesting that vaccines using restricted epitopes can result in broad CD8+ T-cell responses to antigens not present in the vaccine (Corbiere V, et al. Cancer Res 2011; 71:1253-62., Ribas A, et al. Trends Immunol 2003; 24:58-61., Hunder N N, et al. N. Engl. J. Med. 2008; 358:2698-703.). Thus, the present inventors considered that CDCA1-specific Th cell responses may be efficiently induced by vaccination with a CDCA1-derived CTL-epitope peptide. To detect CDCA1-specific Th cell responses in patients, PBMCs isolated from 16 HNC patients vaccinated with CDCA1-A24 (56-64) and 7 HNC patients before vaccination were collected. The donor characteristics are summarized in the table of FIG. 11F. After 1-week of in vitro stimulation of PBMCs with CDCA1-LPs, the frequency of individual CDCA1-LPs-specific T-cells was detected by IFN-gamma ELISPOT assay (FIG. 11A). PBMCs isolated from 10 healthy volunteers were used as controls. Responses were considered positive when the number of IFN-gamma-secreting cells was at least 2-fold above the negative control.

Figure 11C:
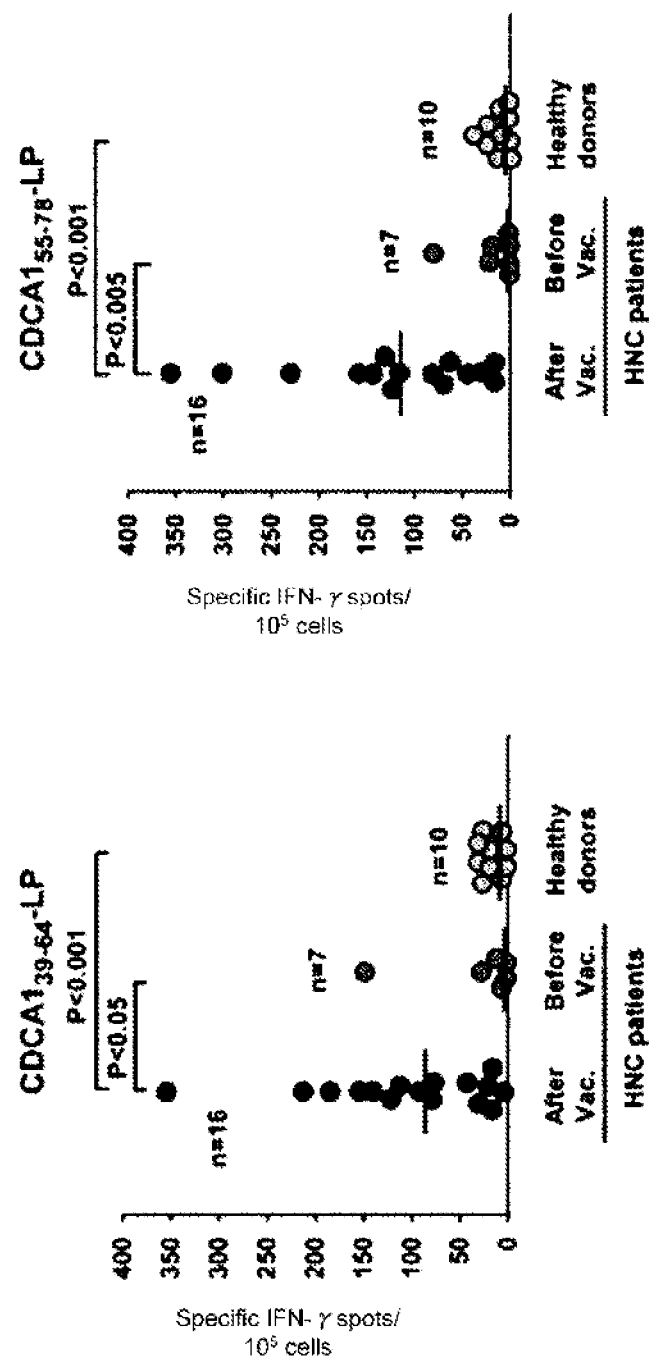
FIG. 11C.
Figure 11D:
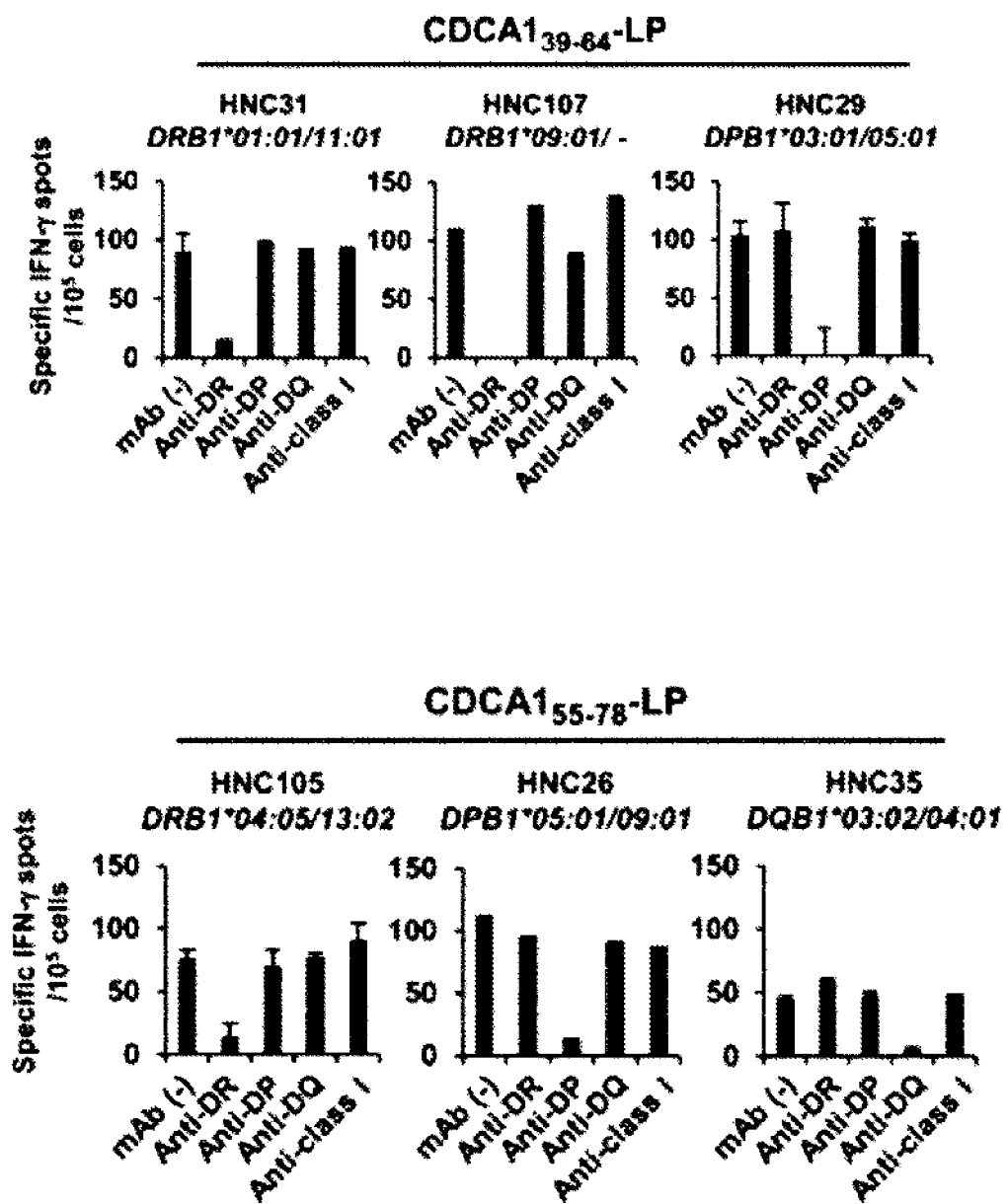
FIG. 11D.
Figure 11E:
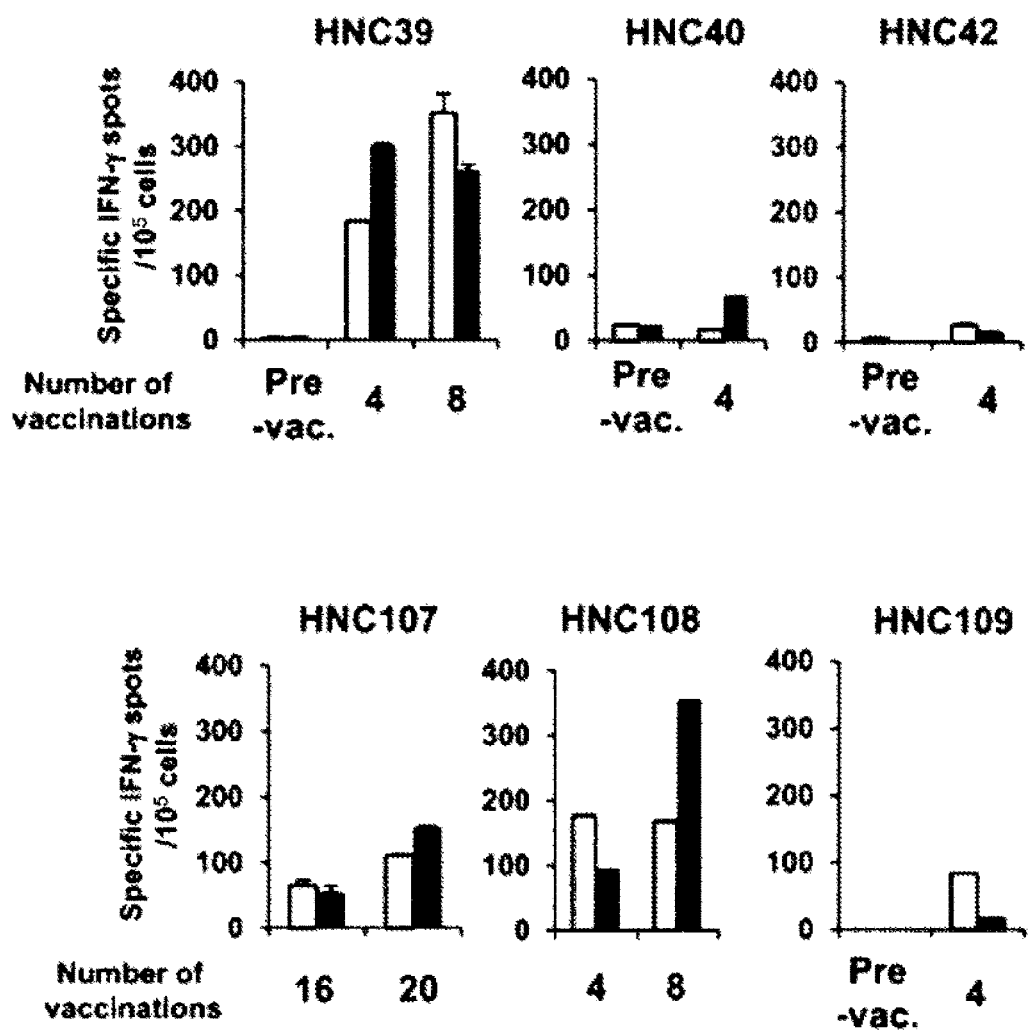
FIG. 11E.

Significant frequency of CDCA1-LP-specific immune responses were observed in HNC patients (CDCA1 (39-64) LP, 14 of 19, 74%; CDCA1 (55-78) LP, 13 of 19, 68%; FIGS. 11B and F), but no specific IFN-gamma responses to CDCA1-LPs were detected in the 10 healthy donors. In a few patients before vaccination, CDCA1-LP-specific Th cell responses were detectable (CDCA1 (39-64) LP, 2 of 7, 29%; CDCA1 (55-78) LP, 2 of 7, 29%; FIG. 11F). On the other hands, in many HNC patients after vaccination with CDCA1-A24 (56-64) SP, CDCA1-LP-specific Th cell responses were detected (CDCA1 (39-64) LP, 12 of 16, 75%; CDCA1 (55-78) LP, 12 of 16, 75%; FIG. 11F). The number of CDCA1-LP-specific IFN-gamma-producing cells in patients after vaccination was significantly larger than in patients before vaccination and healthy donors (FIG. 11C). IFN-gamma production by T-cells was significantly inhibited by addition of anti-HLA-class II mAb, but not by anti-HLA-class I mAb (FIG. 11D). These results indicate that CDCA1-LPs-specific IFN-gamma production was derived from CDCA1-LPs-specific CD4+ T-cells. Interestingly, specific response to CDCA1-LPs were induced or augmented by repeated vaccinations in some HNC patients (FIG. 11E). These observations suggest APCs collected and processed a CDCA1 antigen derived from tumor cells killed by vaccine-induced CTLs and then activated CDCA1-specific Th cells in vivo.

Discussion

It is considered that the most attractive vaccine compounds are synthetic LPs corresponding to the sequence of TAAs that can induce therapeutic CD4+ and CD8+ responses (Melief C J and van der Burg S H. Nat. Rev. Cancer 2008; 8: 351-60, Kenter G G, Welters M J, et al. N. Engl. J. Med. 2009; 361: 1838-47.). Following the injection of these LPs, the patient's DCs will take up the LPs, process them and present all possible CTL-epitopes and Th-epitopes in various HLA class I and HLA class II, respectively. Thus, the inventors considered that an ideal peptide vaccine for cancer immunotherapy should be a single polypeptide that can induce both CTL and Th1 cell restricted by the most commonly found HLA.

In this study, the present inventors identified CDCA1-derived LPs including CTL-epitopes recognized by promiscuous HLA-class II-restricted Th1 cells.

In conclusion, the present inventors first identified CDCA1-derived helper peptides including CTL-epitopes, which not only become a good tool for propagating and activating CDCA1-specific Th1 cell but also CDCA1-specific CTLs by cross-presentation. These findings would contribute to a clinical trial of CDCA1-peptide-based immunotherapy against various types of cancers in the future.

INDUSTRIAL APPLICABILITY

The present invention describes Th1 cell epitope peptides derived from CDCA1 that can induce potent anti-tumor immune responses and thus have applicability to a wide array of cancer types. Such peptides warrant further development as peptide vaccines against cancer, especially against cancers expressing CDCA1. The peptides of the present invention can induce the Th1 cell response and thus cytokines secreted by Th1 cells can help or activate any immune cells responsible for cellular immunity in an antigen independent manner. Therefore, immunotherapeutic strategy provided by the present invention can be applied to any diseases including cancers, as long as the disease can be improved via immune responses mediated by MHC class II molecules. In particular, Th1 cells of the present invention can improve immunological responses raised by CTLs. Therefore, the peptide of the present invention would be beneficial to enhance CTL response against diseases including cancers in a subject.

Moreover, in preferred embodiments, the peptides of the present invention can also induce CTLs against CDCA1 expressing cells, as well as Th1 cells. Such peptide of the present invention can be also useful for the treatment of diseases associated with CDCA1, e.g. cancers, more particularly, breast cancer, bladder cancer, esophageal cancer, small cell lung cancer (SCLC), non-small cell lung cancer (NSCLC) and head-and-neck cancer (HNC).

While the present invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. An isolated peptide consisting of 15-30 amino acids, wherein said peptide comprises
    an amino acid sequence having more than 9 contiguous amino acids from the amino acid sequence of SEQ ID NO: 2
    in which one or two amino acids are substituted, and/or added
    wherein said peptide has ability to induce T helper type 1 (Th1) cells.

2. The isolated peptide of claim 1, wherein the peptide or fragment thereof has abilities to bind at least two kinds of WIC class II molecules.

3. The isolated peptide of claim 2, wherein the MEW class II molecules are selected from the group consisting of HLA-DR4, HLA-DR9, HLA-DR15 and HLA-DP2.

4. The isolated peptide of claim 1, wherein said peptide comprises an amino acid sequence of a peptide having CDCA1-specific cytotoxic T lymphocyte (CTL) inducibility.

5. The isolated peptide of claim 4, wherein said peptide comprises:
    an amino acid sequence of SEQ ID NO: 2
    in which one or two amino acids are substituted, and/or added.

6. A composition comprising one or more peptide(s) having the ability to induce Th1 cells, the peptide(s) consisting of 15-30 amino acids, wherein said peptide(s) comprise an amino acid sequence selected from the group consisting of:
    (a) an amino acid sequence having more than 9 contiguous amino acids from the amino acid sequence of SEQ ID NO: 2; and
    (b) an amino acid sequence in which one or two amino acids are substituted and/or added in the amino acid sequence of SEQ ID NO: 2,
    in combination with an adjuvant in an amount effective to enhance an immune response.

7. The composition of claim 6, wherein said composition further comprises one or more peptides having CTL inducibility.

8. A method for inducing an APC having an ability to induce a Th1 cell, said method comprising a step of contacting an APC with the peptide of claim 1 in vitro, ex vivo or in vivo.

9. A method for inducing an APC having an ability to induce a CTL, said method comprising a step of contacting an APC with the peptide of claim 1 in vitro, ex vivo or in vivo.

10. A method for inducing a Th1 cell, said method comprising a step of
co-culturing a CD4-positive T cell with an APC that presents on its surface a complex of an MHC class II molecule and the peptide of claim 1.

11. A method for inducing a CTL, said method comprising the step selected from the group consisting of:
(a) co-culturing both of a CD4-positive T cell and a CD8-positive T cell with APCs contacted with the peptide of claim 4; and
(b) co-culturing a CD8-positive T cell with an APC contacted with the peptide of claim 4.

12. A method for enhancing an immune response mediated by an MHC class II molecule, wherein the method comprises a step of administering to a subject one or more peptide(s) of claim 1.

13. A method of inducing an immune response against cancer in a subject in need thereof, said method comprising the step of administering to the subject a composition comprising one or more peptide(s) of claim 1.

14. The isolated peptide of claim 5, consisting of the amino acid sequence of SEQ ID NO:2 in which one or two amino acids are substituted and/or added.

15. The composition of claim 6, wherein the peptide consists of the amino acid sequence of SEQ ID NO:2.

\* \* \* \* \*